US012702311B2

(12) United States Patent
Valdez

(10) Patent No.: US 12,702,311 B2
(45) Date of Patent: Aug. 11, 2026

(54) BLOOD-VESSEL-ANCHORED CARDIAC SENSOR

(71) Applicant: Edwards Lifesciences Corporation, Irvine, CA (US)

(72) Inventor: Michael G. Valdez, Riverside, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 894 days.

(21) Appl. No.: 17/676,015

(22) Filed: Feb. 18, 2022

(65) Prior Publication Data

US 2022/0233084 A1 Jul. 28, 2022

Related U.S. Application Data

(63) Continuation of application No. PCT/US2020/045975, filed on Aug. 12, 2020.

(Continued)

(51) Int. Cl.

*A61B 5/145* (2006.01)
*A61B 5/00* (2006.01)

(Continued)

(52) U.S. Cl.

CPC ........ *A61B 5/02152* (2013.01); *A61B 5/6851* (2013.01); *A61B 5/686* (2013.01);

(Continued)

(58) Field of Classification Search

CPC ..... A61B 5/0215-02152; A61B 5/6851-6865; A61B 5/686;

(Continued)

(56) References Cited

U.S. PATENT DOCUMENTS 5,199,428 A 4/1993 Obel et al.
5,411,551 A * 5/1995 Winston .................... A61F 2/92 600/347

(Continued)

FOREIGN PATENT DOCUMENTS

CN 101271029 A 9/2008
CN 105193529 A 12/2015

(Continued)

OTHER PUBLICATIONS

Boston Scientific, https://web.archive.org/web/20171225100836/https://www.bostonscientific.com/en-EU/products/stents-vascular/innova-self-expanding-stent-system.html#, Innova "Triaxial Shaft", Dec. 25, 2017, accessed Jun. 2, 2025. (Year: 2017).*

(Continued)

*Primary Examiner* — Matthew Kremer
*Assistant Examiner* — Aaron Merriam
(74) *Attorney, Agent, or Firm* — Chang and Hale LLP

(57) ABSTRACT

A method of sensing a physiological parameter involves advancing a delivery catheter to a right atrium of a heart of a patient via a transcatheter access path, advancing the delivery catheter through an interatrial septum wall into a left atrium of the heart, deploying a distal anchor of a sensor implant device from the delivery catheter, anchoring the distal anchor of the sensor implant device to a first pulmonary vein, withdrawing the delivery catheter away from the first pulmonary vein, thereby exposing at least a portion of a sensor module of the sensor implant device in the left atrium, deploying a proximal anchor of the sensor implant device from the delivery system, anchoring the proximal anchor of the sensor implant device to a second pulmonary vein, and withdrawing the delivery catheter from the heart.

39 Claims, 31 Drawing Sheets

Related U.S. Application Data

(60) Provisional application No. 62/890,537, filed on Aug. 22, 2019.

(51) Int. Cl.
*A61B 5/0215* (2006.01)
*A61B 5/07* (2006.01)
*A61F 2/82* (2013.01)

(52) U.S. Cl.
CPC .......... *A61B 5/6869* (2013.01); *A61B 5/6876* (2013.01); *A61B 2562/0247* (2013.01)

(58) Field of Classification Search
CPC ................ A61B 5/6869; A61B 5/6876; A61B 2562/0247; A61B 2560/063–066; A61B 5/145–14503; A61B 5/6882; A61B 5/061; A61F 2/82–86; A61F 2002/821–828
See application file for complete search history.

(56) References Cited

U.S. PATENT DOCUMENTS 6,053,873 A * 4/2000 Govari ................. A61B 5/0031 600/468
6,309,350 B1 10/2001 Vantassel et al.
6,331,163 B1 12/2001 Kaplan
6,783,499 B2 8/2004 Schwartz
7,137,953 B2 11/2006 Eigler et al.
7,340,288 B1 3/2008 Karicherla et al.
7,389,142 B2 6/2008 Holmstroem
7,452,334 B2 11/2008 Gianchandani et al.
7,572,228 B2 8/2009 Wolinsky et al.
8,057,399 B2 11/2011 Greenland et al.
8,175,668 B1 5/2012 Nabutovsky et al.
8,308,794 B2 11/2012 Martinson et al.
8,401,643 B2 3/2013 Griswold et al.
8,475,372 B2 7/2013 Schell et al.
8,929,982 B2 1/2015 Holmstrom et al.
9,662,021 B2 5/2017 Chow et al.
9,999,528 B2 6/2018 Kim et al.
10,098,551 B2 10/2018 Doan et al.
10,238,339 B2 3/2019 Dlugach et al.
10,806,352 B2 10/2020 Sweeney et al.
11,039,924 B2 6/2021 Yaron
2002/0045921 A1* 4/2002 Wolinsky ............. A61N 1/3787 607/61
2002/0151816 A1 10/2002 Rich et al.
2003/0055345 A1* 3/2003 Eigler .................. A61B 5/0215 600/486
2003/0065375 A1* 4/2003 Eskuri ....................... A61F 2/95 623/1.11
2005/0065589 A1 3/2005 Schneider et al.
2005/0267478 A1 12/2005 Corradi et al.
2005/0288722 A1 12/2005 Eigler et al.
2006/0020324 A1 1/2006 Schmid et al.
2006/0079740 A1* 4/2006 Silver .................. A61B 5/6882 600/353
2006/0161171 A1 7/2006 Schwartz
2007/0021665 A1 1/2007 Hettrick et al.
2007/0129637 A1* 6/2007 Wolinsky ........... A61B 5/02152 600/549
2008/0051863 A1 2/2008 Schneider et al.
2008/0082005 A1 4/2008 Stern et al.
2009/0024042 A1 1/2009 Nunez et al.
2009/0248105 A1 10/2009 Keilman et al.
2010/0179449 A1 7/2010 Chow et al.
2011/0288436 A1 11/2011 Stone
2012/0022507 A1 1/2012 Najafi et al.
2012/0029598 A1 2/2012 Zhao
2012/0116489 A1 5/2012 Khairkhahan et al.
2012/0197349 A1 8/2012 Griswold et al.
2012/0239142 A1 9/2012 Liu et al.
2012/0259217 A1 10/2012 Gerrans et al.
2012/0265296 A1 10/2012 McNamara et al.
2013/0046152 A1 2/2013 Najafi et al.
2013/0165967 A1 6/2013 Amin et al.
2013/0281774 A1 10/2013 Honaryar et al.
2013/0338763 A1 12/2013 Rowe et al.
2014/0107722 A1 4/2014 Kaiser et al.
2014/0155768 A1 6/2014 Orion et al.
2014/0213916 A1* 7/2014 Doan ................... A61B 5/0215 600/488
2014/0214149 A1 7/2014 Kuraguntla et al.
2014/0288480 A1* 9/2014 Zimmerman ........... A61F 2/848 606/108
2015/0025612 A1 1/2015 Haasl et al.
2015/0112383 A1 4/2015 Sherman et al.
2015/0157268 A1 6/2015 Winshtein et al.
2015/0351648 A1 12/2015 Harvey et al.
2016/0045165 A1 2/2016 Braido et al.
2016/0045316 A1 2/2016 Braido et al.
2016/0157868 A1 6/2016 Tillman et al.
2016/0256141 A1 9/2016 Mendez et al.
2016/0338823 A1 11/2016 Akingba
2017/0095163 A1 4/2017 Bitzer et al.
2017/0319067 A1 11/2017 Najafi
2018/0071542 A1 3/2018 Nyberg et al.
2018/0098772 A1 4/2018 Goldshtein et al.
2018/0140206 A1* 5/2018 Bitzer ................ A61N 1/37512
2018/0140444 A1 5/2018 Neuss et al.
2018/0168460 A1 6/2018 Morris et al.
2018/0303426 A1 10/2018 Royer et al.
2019/0083801 A1 3/2019 Yang et al.
2019/0343388 A1 11/2019 Bahmanyar et al.
2020/0054867 A1 2/2020 Schwartz et al.
2020/0094048 A1 3/2020 Regnier et al.
2020/0155014 A1 5/2020 Arthur et al.
2020/0196944 A1 6/2020 Minor et al.
2020/0289257 A1 9/2020 Marquez et al.
2021/0000581 A9 1/2021 Eigler et al.
2021/0121130 A1 4/2021 Nagy et al.
2021/0177277 A1 6/2021 Cros et al.

FOREIGN PATENT DOCUMENTS

EP 2338420 A1 6/2011
WO 2007058872 A2 5/2007
WO WO-2007057739 A1 5/2007
WO WO-2012031204 A2 3/2012
WO WO-2016178171 A1 11/2016
WO WO-2018213320 A1 11/2018
WO WO-2020123338 A1 6/2020
WO WO-2020163112 A1 8/2020
WO WO-2021015929 A1 1/2021
WO WO-2021050589 A1 3/2021
WO WO-2021113449 A1 6/2021
WO WO-2022046425 A1 3/2022
WO WO-2022046473 A1 3/2022
WO WO-2022051716 A1 3/2022
WO WO-2023177824 A1 9/2023

OTHER PUBLICATIONS

Abraham W.T., et al., "V-LAP Left Atrial Monitoring system for Patients with Chronic sysTOlic and Diastolic Congestive Heart FailuRe First-in-Human," Journal of Cardial Failure, Churchill Livingstone, Naperville, IL, US, Aug. 1, 2019, vol. 25, No. 8S, pp. S74-S75 (2 Pages).

Chow E.Y., et al., "Toward an Implantable Wireless Cardiac Monitoring Platform Integrated with an FDA-Approved Cardiovascular Stent," Journal of Interventional Cardiology, 2009, vol. 22, No. 5, pp. 479-487, Wiley Periodicals, Inc., Hoboken, New Jersey.

Hur T., et al., "Improving Structural Strength and Stability of Parylene-based Capacitive Micro Pressure Sensor Using Corrugated Sidewall", MEMS 2019, Jan. 2019, pp. 727-730. I XP093213755, Retrieved from the Internet: URL:https://ieeexplore.IEEE.org/stampPDF/getPDF.jsp?tp=&arnumber=8870736&ref=aHROCHM6Ly9zY2hvbGFyLmdvb2dsZSSjb20v figures 1-6.

Kim A., et al., "An Implantable Pressure Sensing System With Electromechanical Interrogation Scheme," IEEE Transactions on

(56) References Cited

OTHER PUBLICATIONS

Biomedical Engineering, IEEE, USA, Jul. 1, 2014, vol. 61(7), pp. 2209-2217, DOI: 10.1109/TBME.2014.2318023, ISSN 0018-9294, XP011551241, (Jun. 16, 2014).
NEEMA p. K., et al., "Left Atrial Pressure Waveform: Does It Show Mitral Insufficiency," Journal of Cardiothoracic and Vascular Anesthesia, Diagnostic Dilemmas, Elsevier, Amsterdam, NL, Apr. 2008, vol. 22, No. 2, pp. 318-320, Mar. 28, 2008.
Nitter-Hauge S., et al., "Clinical and Hemodynamic Results After Combined Aortic and Mitral Valve Replacement With the Lillehei-Kaster Pivoting Disc Valve," Experimental and Laboratory Reports, American Heart Journal, May 1, 1979, vol. 97, No. 5, pp. 599-607.
O'rourke R.A., et al., "Mitral Valve Regurgitation, "Current Problems in Cardiology, May 1, 1984, vol. 9, No. 3, pp. 1-52.
Snyder R.W.S., et al., "Predictive Value of Prominent Pulmonary Arterial Wedge V Waves in Assessing the Presence and Severity of Mitral Regurgitation," Valvular Heart Disease, The American Journal of Cardiology, Mar. 15, 1994, vol. 73, No. 8, pp. 568-570.
Tice F.D., et al., "Transesophageal Echocardiographic Assessment of Reversal of Systolic Pulmonary Venous Flow in Mitral Stenosis," The American Journal of Cardiology, Jan. 1, 1995, vol. 75, No. 1, pp. 58-60.

* cited by examiner

200
WITHDRAW AND MOVE DELIVERY CATHETER TO 2ND PULMONARY VEIN
210
DEPLOY 2ND ANCHOR IN 2ND PULMONARY VEIN
212
122
23
131
105
18
116
2
5
3
106
124
133
100
110
119
118
121

BLOOD-VESSEL-ANCHORED CARDIAC SENSOR

RELATED APPLICATION

This application is a continuation application of PCI International Patent Application Serial No. PCT/US2020/0415975, filed Aug. 12, 2020 and entitled BLOOD-VESSEL-ANCHORED CARDIAC SENSOR, which claims priority based on United States Provisional Patent Application Ser. No. 62/890,537, filed on Aug. 22, 2019 and entitled PULMONARY-VEIN-ANCHORED CARDIAC SENSOR, the complete disclosures of both of which are hereby incorporated by reference herein in their entireties.

BACKGROUND

Field

The present disclosure generally relates to the field of medical devices and procedures.

Description of Related Art

Certain physiological parameters associated with chambers of the heart, such as fluid pressure and blood flow, can have an impact on patient health prospects. In particular, high cardiac fluid pressure can lead to heart failure, embolism formation, and/or other complications in some patients. Therefore, information relating to physiological conditions, such as pressure, in one or more chambers of the heart can be beneficial.

SUMMARY

Described herein are one or more methods and/or devices to facilitate monitoring of physiological parameter(s) associated with the left atrium using one or more sensor implant devices implanted in or to one or more pulmonary veins and/or associated anatomy/tissue.

In some implementations, the present disclosure relates to a method of sensing a physiological parameter. The method comprises advancing a delivery catheter to a right atrium of a heart of a patient via a transcatheter access path, advancing the delivery catheter through an interatrial septum wall into a left atrium of the heart, deploying a distal anchor of a sensor implant device from the delivery catheter, anchoring the distal anchor of the sensor implant device to a first pulmonary vein, withdrawing the delivery catheter away from the first pulmonary vein, thereby exposing at least a portion of a sensor module of the sensor implant device in the left atrium, deploying a proximal anchor of the sensor implant device from the delivery system, anchoring the proximal anchor of the sensor implant device to a second pulmonary vein, and withdrawing the delivery catheter from the heart.

The method may further comprise sensing a physiological parameter associated with the left atrium using a sensor element of the sensor module. For example, the physiological parameter can be left atrial blood pressure.

In some embodiments, the sensor implant device comprises a first arm portion that physically couples the sensor module to the distal anchor and a second arm portion that physically couples the sensor module to the proximal anchor. For example, the first and second arm portions may be part of a unitary arm structure coupled between the distal anchor device and the proximal anchor device.

In some embodiments, the sensor module includes an arm engagement feature configured to attach the sensor module to the arm structure.

In some embodiments, the sensor module includes a guide wire lumen configured to have a guide wire disposed therein. For example, the method may further comprise advancing the delivery catheter along a pre-positioned guide wire.

In some embodiments, the sensor module comprises a housing and a sensor element disposed at least partially within the housing. For example, the sensor element may be disposed at least partially within the housing such that a transducer surface of the sensor element is at least partially exposed to blood in the left atrium when the sensor implant device is disposed within the left atrium.

In some embodiments, the transducer surface is a pressure transducer diaphragm.

In some implementations, anchoring the distal anchor of the sensor implant device to the first pulmonary vein involves expanding a stent anchor within a conduit of the first pulmonary vein.

In some implementations, the present disclosure relates to a sensor implant device comprising a sensor module including a housing and a sensor element, a first stent anchor coupled to the sensor module via a first arm structure portion, and a second stent anchor coupled to the sensor module via a second arm structure portion.

Each of the first and second stent anchors may be self-expanding.

In some embodiments, the sensor element is configured to generate a signal indicative of a physiological parameter. For example, the physiological parameter can be fluid pressure.

The first and second arm structure portions can be part of a unitary bridge structure coupled between the first stent anchor and the second stent anchor. For example, the sensor module can include an engagement feature configured to engage with the bridge structure.

In some embodiments, the engagement feature is associated with an underside of a housing of the sensor module.

The sensor module can include a channel feature configured to receive therein a guide wire.

In some embodiments, the sensor element comprises a transducer surface that is at least partially exposed external to the housing. For example, the transducer surface can be associated with a pressure transducer diaphragm.

In some implementations, the present disclosure relates to a delivery system comprising an outer shaft, a sensor implant device disposed at least partially within the outer shaft.

The sensor implant device comprises a first anchor device, a second stent anchor device, and a sensor module physically coupled to the first anchor device and the second anchor device.

The delivery system further comprises a distal inner shaft disposed at least partially within the outer shaft and configured to axially abut the first anchor device within the outer shaft.

In some embodiments, the first anchor device is disposed without the distal inner shaft and distal to the inner shaft and the sensor module is disposed at least partially within the distal inner shaft.

The delivery system can further comprise a proximal inner shaft disposed at least partially within the distal inner shaft and configured to axially abut the sensor module within the distal inner shaft. For example, in some implementations, the second anchor device is disposed at least partially within the proximal inner shaft, the proximal inner shaft has a diameter that is less than a diameter of the distal inner shaft, the second anchor is disposed within the proximal inner shaft in an at least partially compressed configuration, and the second anchor in the at least partially compressed configuration has a diameter that is less than a diameter of the first anchor as configured and disposed within the outer shaft.

The second anchor can be coupled to the sensor module via an arm portion that is bent such that an end portion of the second anchor is distally oriented within the proximal inner shaft.

The delivery system can further comprise a pusher device disposed at least partially within the proximal inner shaft and configured to axially abut the second anchor device within the proximal inner shaft. For example, the pusher device can include a central lumen configured to receive a guidewire therein.

In some implementations, the present disclosure relates to a sensor implant device comprising a stent anchor, a first arm structure connected to the stent anchor and extending axially beyond an axial end of the stent anchor, and a sensor device secured to the first arm structure.

The stent anchor may be dimensioned to anchor within any of a pulmonary vein, a coronary sinus, and/or at least one of a superior vena cava or an inferior vena cava in an expanded deployment configuration.

The first arm structure may have a shape memory characteristics that cause the first arm structure to deflect radially outward with respect to an axis of the stent anchor when the sensor implant device is deployed.

The sensor implant device may further comprise a second arm structure connected to the stent anchor and secured to the sensor device. For example, the first arm structure and the second arm structure may be connected to opposite circumferential portions of the stent anchor, and/or the first arm structure and the second arm structure may be configured to hold the sensor device over a central axis of the stent anchor.

In some implementations, the present disclosure relates to a sensor implant device comprising a stent anchor and a sensor device secured to an inner diameter of the stent anchor.

In some embodiments, the sensor device comprises a housing that is configured to be engaged with one or more cells of a lattice structure of the stent anchor.

The sensor device can be secured to the stent anchor at an axial end of the stent anchor.

In some implementations, the present disclosure relates to a method of implanting a sensor implant device. The method comprises advancing a delivery system into to a first vena cava of a patient via a transcatheter access path, advancing the delivery system through at least a portion of a right atrium of the patient and into a second vena cava of the patient, deploying a distal anchor of a sensor implant device from the delivery system, anchoring the distal anchor of the sensor implant device within the second vena cava, withdrawing the delivery system through the at least a portion of the right atrium, thereby exposing at least a portion of a sensor device of the sensor implant device and a first support arm portion coupling the sensor device to the distal anchor in the right atrium, deploying a proximal anchor of the sensor implant device from the delivery system within the first vena cava, anchoring the proximal anchor of the sensor implant device to within the first vena cava, and withdrawing the delivery system from the patient.

The sensor device can be coupled to the proximal anchor via a second support arm portion.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIGS. 12-1, 12-2, 12-3, and 12-4 show a flow diagram illustrating a process for implanting a sensor implant device in accordance with one or more embodiments.

FIGS. 13-1, 13-2, 13-3, and 13-4 provide cross-sectional images of cardiac anatomy and certain devices/systems corresponding to operations of the process of FIGS. 12-1, 12-2, 12-3, and 12-4 according to one or more embodiments.

FIGS. 14-1, 14-2, 14-3, and 14-4 provide side views of a sensor implant device in various configurations corresponding to the operations of the process of FIGS. 12-1, 12-2, 12-3, and 12-4 according to one or more embodiments.

DETAILED DESCRIPTION

The headings provided herein are for convenience only and do not necessarily affect the scope or meaning of the claimed inventive subject matter. The present disclosure relates to systems, devices, and methods for implanting and utilizing sensor implant devices configured to be implanted in the heart, such as at least partially within the left atrium and/or anchored to one or more pulmonary veins in fluid communication therewith.

Although certain preferred embodiments and examples are disclosed below, inventive subject matter extends beyond the specifically disclosed embodiments to other alternative embodiments and/or uses, and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The following includes a general description of human cardiac anatomy that is relevant to certain inventive features and embodiments disclosed herein and is included to provide context for certain aspects of the present disclosure. In humans and other vertebrate animals, the heart generally comprises a muscular organ having four pumping chambers, wherein the flow of blood between the pumping chambers is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to associated blood vessels (e.g., pulmonary, aorta, etc.).

Figure 1:
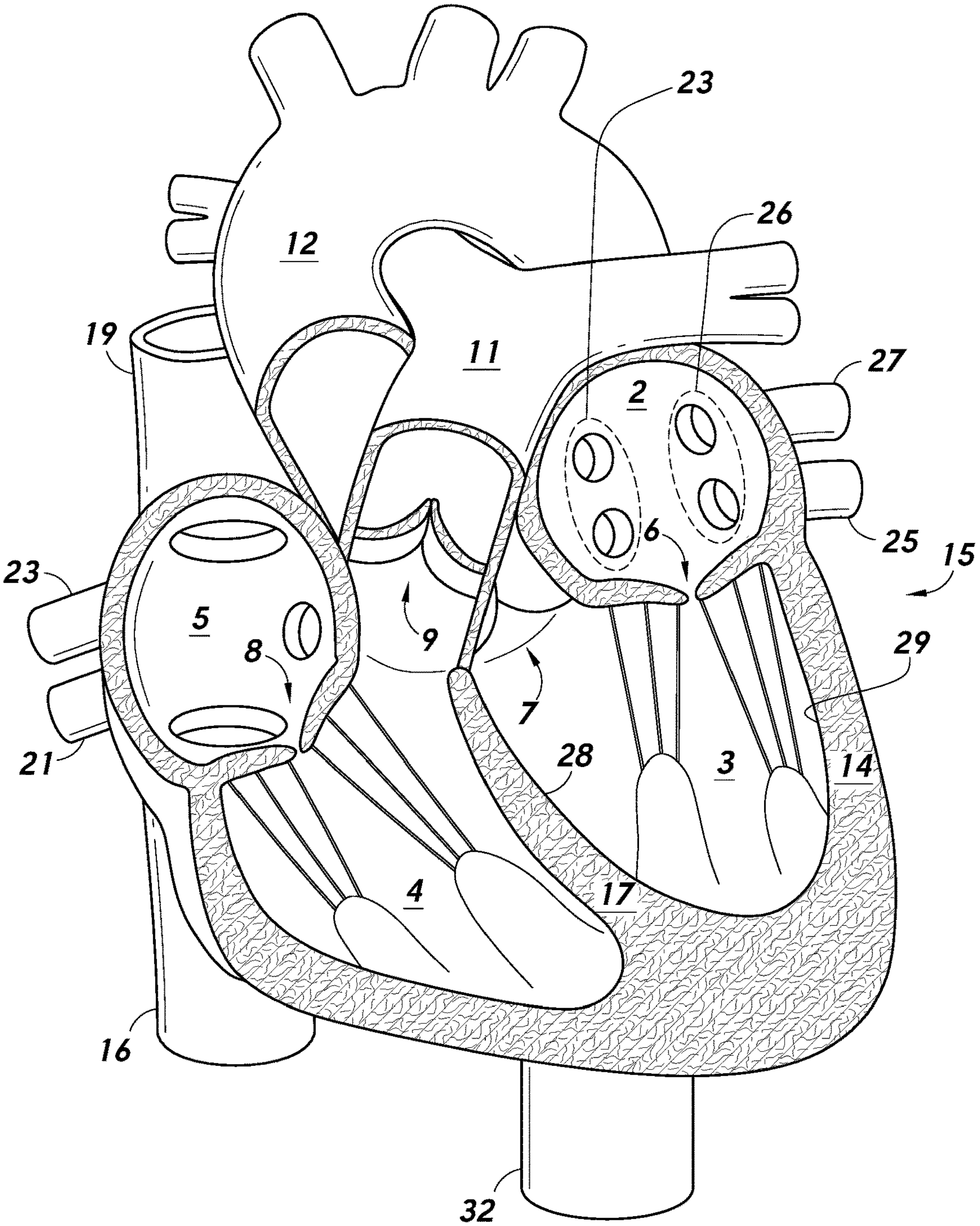
FIG. 1 shows a cross-sectional view of an example human heart.
Figure 2:
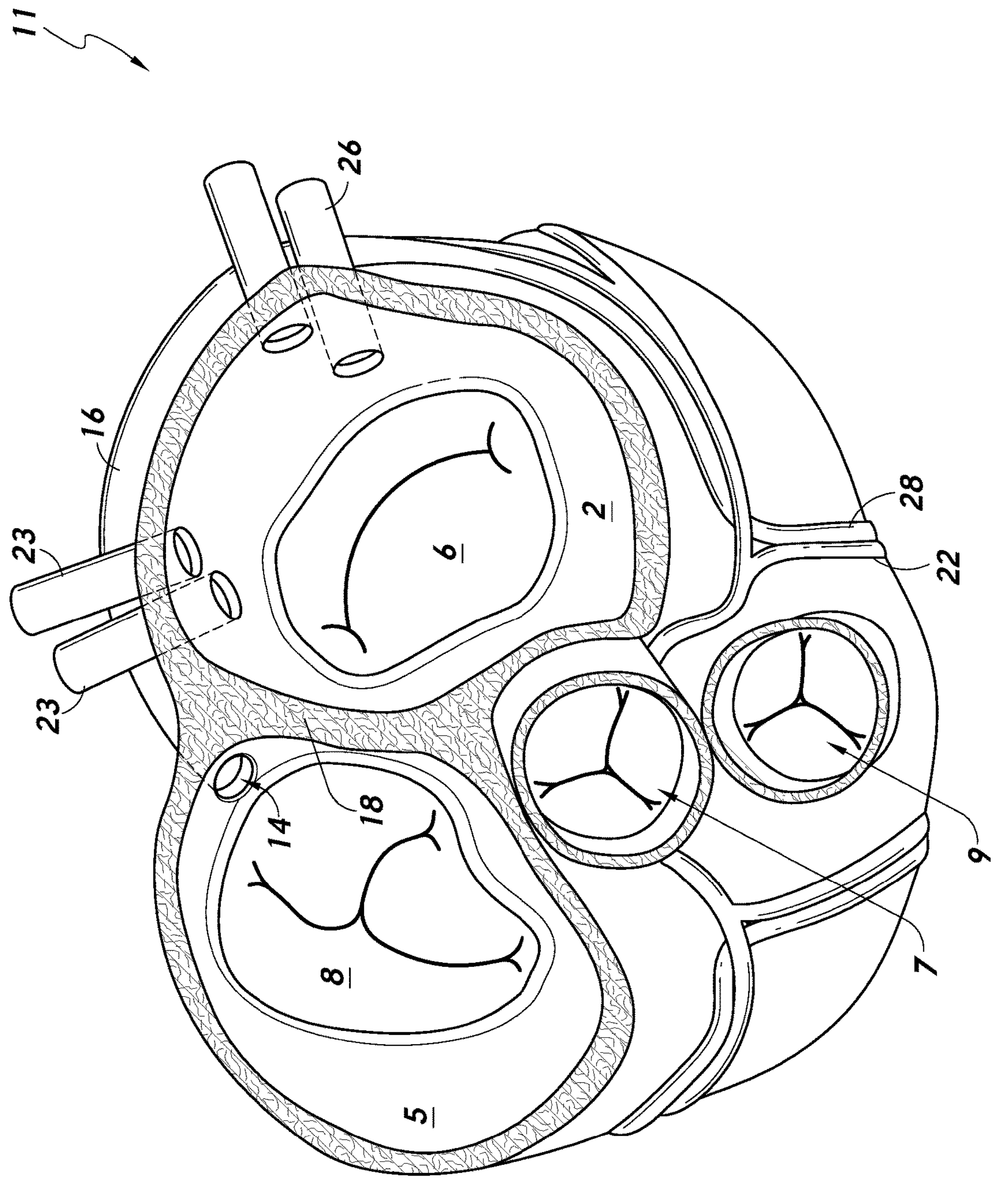
FIG. 2 shows a top-down atrial cross-sectional view of a human heart.

FIGS. 1 and 2 illustrate vertical and horizontal cross-sectional views, respectively, of an example heart 1 having various features/anatomy relevant to certain aspects of the present inventive disclosure. The heart 1 includes four chambers, namely the left ventricle 3, the left atrium 2, the right ventricle 4, and the right atrium 5. A wall of muscle, referred to as the septum, separates the left-side chambers from the right-side chambers. In particular, an atrial septum wall portion 18 (referred to herein as the "atrial septum," "interatrial septum," or "septum") separates the left atrium 2 from the right atrium 5, whereas a ventricular septum wall portion 17 (referred to herein as the "ventricular septum," "interventricular septum," or "septum") separates the left ventricle 3 from the right ventricle 4. The inferior tip 19 of the heart 1 is referred to as the apex and is generally located on the midclavicular line, in the fifth intercostal space. The apex can be considered part of the greater apical region 39 identified in the drawings.

The left ventricle 3 is the primary pumping chamber of the heart 1. A healthy left ventricle is generally conical or apical in shape, in that it is longer (along a longitudinal axis extending in a direction from the aortic valve 7 (not shown in FIG. 1) to the apex) than it is wide (along a transverse axis extending between opposing walls 28, 29 at the widest point of the left ventricle) and descends from a base 15 with a decreasing cross-sectional diameter and/or circumference to the point or apex. Generally, the apical region 39 of the heart is a bottom region of the heart that is within the left and/or right ventricular region(s) but is distal to the mitral 6 and tricuspid 8 valves and disposed toward the tip 19 of the heart.

The pumping of blood from the left ventricle 3 is accomplished by a squeezing motion and a twisting or torsional motion. The squeezing motion occurs between the lateral wall 14 of the left ventricle 3 and the septum 17. The twisting motion is a result of heart muscle fibers that extend in a circular or spiral direction around the heart. When these fibers contract, they produce a gradient of angular displacements of the myocardium from the apex to the base 15 about the longitudinal axis of the heart. The resultant force vectors extend at angles from about 30-60 degrees to the flow of blood through the aortic valve 7. The contraction of the heart is manifested as a counterclockwise rotation of the apex relative to the base 15 when viewed from the apex. The contractions of the heart, in connection with the filling volumes of the left atrium 2 and ventricle 3, respectively, can result in relatively high fluid pressures in the left side of the heart at least during certain phase(s) of the cardiac cycle, the results of which are discussed in detail below.

The four valves of the heart aid the circulation of blood in the heart. The tricuspid valve 8 separates the right atrium 5 from the right ventricle 4. The tricuspid valve 8 generally has three cusps or leaflets and advantageously closes during ventricular contraction (i.e., systole) and opens during ventricular expansion (i.e., diastole), The pulmonary valve 9 separates the right ventricle 4 from the pulmonary artery 11 and generally is configured to open during systole so that blood may be pumped toward the lungs from the right ventricle 4, and close during diastole to prevent blood from leaking back into the right ventricle 4 from the pulmonary artery. The pulmonary valve 9 generally has three cusps/leaflets. The mitral valve 6 generally has two cusps/leaflets and separates the left atrium 2 from the left ventricle 3. The mitral valve 6 may generally be configured to open during diastole so that blood in the left atrium 2 can flow into the left ventricle 3, and close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

The atrioventricular (i.e., mitral and tricuspid) heart valves are generally associated with a sub-valvular apparatus (not shown), including a collection of chordae tendineae and papillary muscles securing the leaflets of the respective valves to promote and/or facilitate proper coaptation of the valve leaflets and prevent prolapse thereof. The papillary muscles, for example, may generally comprise finger-like projections from the ventricle wall. Surrounding the ventricles (3, 4) are a number of arteries 22 that supply oxygenated blood to the heart muscle and a number of veins 28 that return the blood from the heart muscle to the right atrium 5 via the coronary sinus 16 (see FIG. 2). The coronary sinus 16 is a relatively large vein that extends generally around the upper portion of the left ventricle 3 and provides a return conduit for blood returning to the right atrium 5. The coronary sinus 16 terminates at the coronary ostium 14, through which the blood enters the right atrium.

The primary roles of the left atrium 2 are to act as a holding chamber for blood returning from the lungs (not shown) and to act as a pump to transport blood to other areas of the heart. The left atrium 2 receives oxygenated blood from the lungs via the pulmonary veins 23, 26. The oxygenated blood that is collected from the pulmonary veins 23, 26 in the left atrium 2 enters the left ventricle 3 through the mitral valve 6. In some patients, the walls of the left atrium 2 are slightly thicker than the walls of the right atrium 5. Deoxygenated blood enters the right atrium 5 through the inferior 29 and superior 19 venae cavae. The right side of the heart then pumps this deoxygenated blood into the pulmonary arteries around the lungs. There, fresh oxygen enters the blood stream, and the blood moves to the left side of the heart via a network of pulmonary veins ultimately terminating at the left atrium 2, as shown.

The ostia 23, 26 of the pulmonary veins are generally located at or near posterior left atrial wall of the left atrium 2. The right pulmonary veins 21, 23 carry blood from the right lung to the left atrium, where it is distributed to the rest of the circulatory system as described in detail herein. The right pulmonary veins include the right inferior pulmonary vein 21 and the right superior pulmonary vein 23, as shown. Meanwhile, the left pulmonary veins 25, 27 generally include the left inferior pulmonary vein 25 and the left superior pulmonary vein 27. The left pulmonary veins generally carry blood from the left lung into the left atrium 2, where it continues to flow to the rest the body, Heart Failure As referenced above, certain physiological conditions or parameters associated with the cardiac anatomy can impact the health of a patient. For example, congestive heart failure is a condition associated with the relatively slow movement of blood through the heart and/or body, which causes the fluid pressure in one or more chambers of the heart to increase. As a result, the heart does not pump sufficient oxygen to meet the body's needs. The various chambers of the heart may respond to pressure increases by stretching to hold more blood to pump through the body or by becoming relatively stiff and/or thickened. The walls of the heart can eventually weaken and become unable to pump as efficiently. In some cases, the kidneys may respond to cardiac inefficiency by causing the body to retain fluid. Fluid buildup in arms, legs, ankles, feet, lungs, and/or other organs can cause the body to become congested, which is referred to as congestive heart failure. Acute decompensated congestive heart failure is a leading cause of morbidity and mortality, and therefore treatment and/or prevention of congestive heart failure is a significant concern in medical care.

The treatment and/or prevention of heart failure (e.g., congestive heart failure) can advantageously involve the monitoring of pressure in one or more chambers or regions of the heart or other anatomy, such as monitoring of left atrial pressure. As described above, pressure buildup in one or more chambers or areas of the heart can be associated with congestive heart failure. However, without direct or indirect monitorings of cardiac pressure (e.g., left atrial pressure, it can be difficult to infer, determine, or predict the presence or occurrence of congestive heart failure. For example, treatments or approaches not involving direct or indirect pressure monitoring may involve measuring or observing other present physiological conditions of the patient, such as measuring body weight, thoracic impedance, right heart catheterization, or the like.

In some solutions, pulmonary capillary wedge pressure can be measured as a surrogate of left atrial pressure. For example, a pressure sensor may be disposed or implanted in the pulmonary artery, and readings associated therewith may be used as a surrogate for left atrial pressure. However, with respect to catheter-based pressure measurement in the pulmonary artery or certain other chambers or regions of the heart, use of invasive catheters may be required to maintain such pressure sensors, which may be uncomfortable or difficult to implement. Furthermore, certain lung-related conditions may affect pressure readings in the pulmonary artery, such that the correlation between pulmonary artery pressure and left atrial pressure may be undesirably attenuated. As an alternative to pulmonary artery pressure measurement, pressure measurements in the right ventricle outflow tract may relate to left atrial pressure as well. However, the correlation between such pressure readings and left atrial pressure may not be sufficiently strong to be utilized in congestive heart failure diagnostics, prevention, and/or treatment.

Additional solutions may be implemented for deriving or inferring left atrial pressure. For example, the E/A ratio, which is a marker of the function of the left ventricle of the heart representing the ratio of peak velocity blood flow from gravity in early diastole (the E wave) to peak velocity flow in late diastole caused by atrial contraction (the A wave), can be used as a surrogate for measuring left atrial pressure. The E/A ratio may be determined using echocardiography or other imaging technology; generally, abnormalities in the DA ratio may suggest that the left ventricle cannot fill with blood properly in the period between contractions, which may lead to symptoms of heart failure, as explained above. However, E/A ratio determination generally does not provide absolute pressure measurement values.

Various methods for identifying and/or treating congestive heart failure involve the observation of worsening congestive heart failure symptoms and/or changes in body weight. However, such signs may appear relatively late and/or be relatively unreliable. For example, daily body-weight measurements may vary significantly (e.g., up to 9% or more) and may be unreliable in signaling heart-related complications. Furthermore, treatments guided by monitoring signs, symptoms, weight, and/or other biomarkers have not been shown to substantially improve clinical outcomes. In addition, for patients that have been discharged, such treatments may necessitate remote telemedicine systems.

The present disclosure provides systems, devices, and methods for guiding the administration of medication relating to the treatment of congestive heart failure at least in part by directly monitoring pressure in the left atrium, or other chamber or vessel for which pressure measurements are indicative of left atrial pressure, in order to reduce hospital readmissions, morbidity, and/or otherwise improve the health prospects of patient at risk of heart failure.

Cardiac Pressure Monitoring

Cardiac pressure monitoring in accordance with embodiments of the present disclosure may provide a proactive intervention mechanism for preventing or treating congestive heart failure. Generally, increases in ventricular filling pressures associated with diastolic and/or systolic heart failure can occur prior to the occurrence of symptoms that lead to hospitalization. For example, cardiac pressure indicators may present weeks prior to hospitalization for some patients. Therefore, pressure monitoring systems in accordance with embodiments of the present disclosure may advantageously be implemented to reduce instances of hospitalization by guiding the appropriate or desired titration and/or administration of medications before the onset of heart failure.

Dyspnea represents a cardiac pressure indicator characterized by shortness of breath or the feeling that one cannot breathe well enough. Dyspnea may result from elevated atrial pressure, which may cause fluid buildup in the lungs from pressure back-up. Pathological dyspnea can result from congestive heart failure. However, a significant amount of time may elapse between the time of initial pressure elevation and the onset of dyspnea, and therefore symptoms of dyspnea may not provide sufficiently-early signaling of elevated atrial pressure. By monitoring pressure directly according to embodiments of the present disclosure, normal ventricular filling pressures may advantageously be maintained, thereby preventing or reducing effects of heart failure, such as dyspnea.

Figure 3:
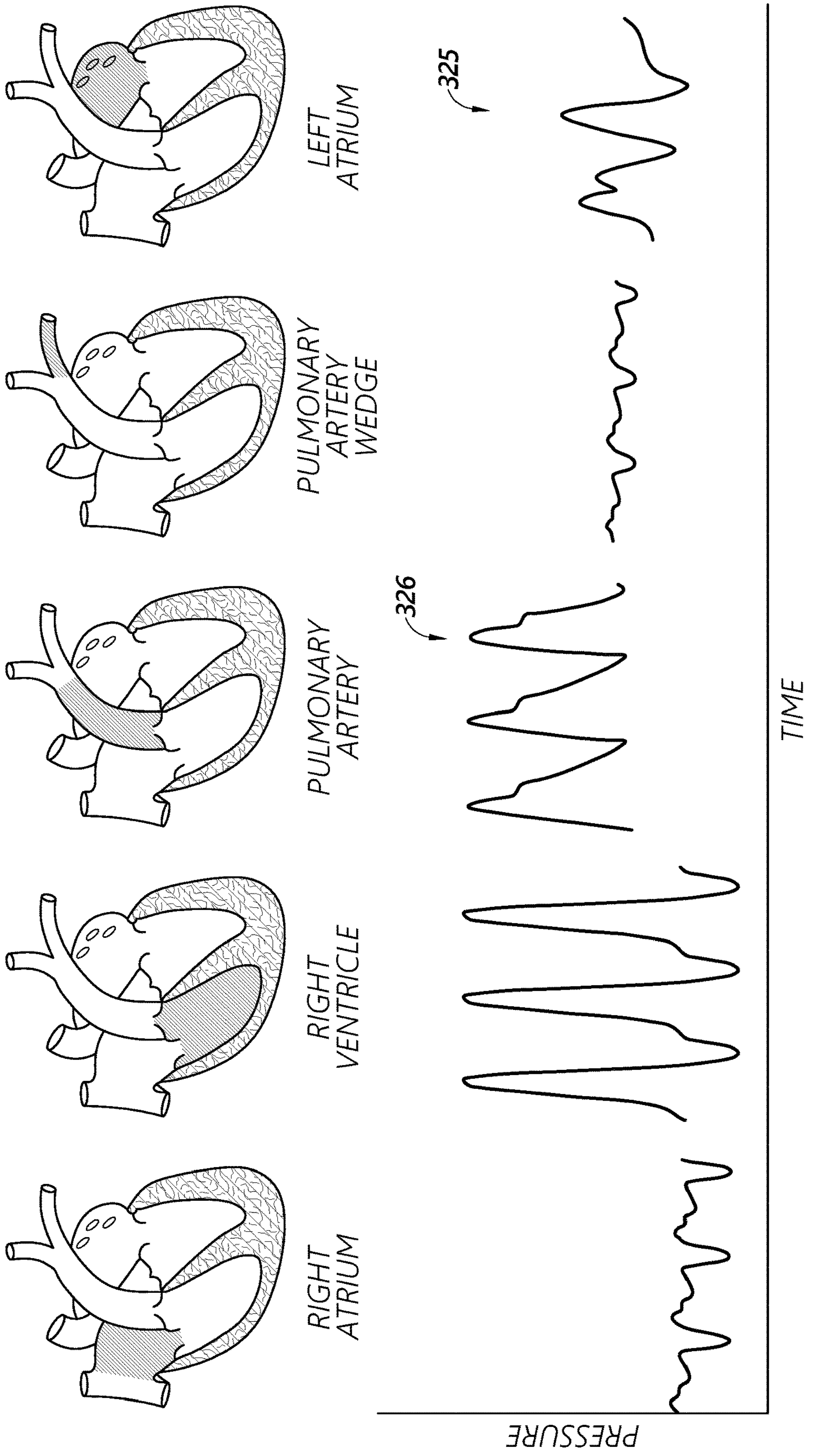
FIG. 3 illustrates example pressure waveforms associated with various chambers and vessels of the heart according to one or more embodiments.

As referenced above, with respect to cardiac pressures, pressure elevation in the left atrium may be particularly correlated with heart failure. FIG. 3 illustrates example pressure waveforms associated with various chambers and vessels of the heart according to one or more embodiments. The various waveforms illustrated in FIG. 3 may represent waveforms obtained using right heart catheterization to advance one or more pressure sensors to the respective illustrated and labeled chambers or vessels of the heart. As illustrated in FIG. 3, the waveform 325, which represents left atrial pressure, may be considered to provide the best feedback for early detection of congestive heart failure. Furthermore, there may generally be a relatively strong correlation between increases and left atrial pressure and pulmonary congestion.

Left atrial pressure may generally correlate well with left ventricular end-diastolic pressure. However, although left atrial pressure and end-diastolic pulmonary artery pressure can have a significant correlation, such correlation may be weakened when the pulmonary vascular resistance becomes elevated. That is, pulmonary artery pressure generally fails to correlate adequately with left ventricular end-diastolic pressure in the presence of a variety of acute conditions, which may include certain patients with congestive heart failure. For example, pulmonary hypertension, which affects approximately 35-83% of patients with heart failure, can affect the reliability of pulmonary artery pressure measurement for estimating left-sided filling pressure. Therefore, pulmonary artery pressure measurement alone, as represented by the waveform 326, may be an insufficient or inaccurate indicator of left ventricular end-diastolic pressure, particularly for patients with co-morbidities, such as lung disease and/or thromboembolism. Left atrial pressure may further be correlated at least partially with the presence and/or degree of mitral regurgitation.

Left atrial pressure readings may be relatively less likely to be distorted or affected by other conditions, such as respiratory conditions or the like, compared to the other pressure waveforms shown in FIG. 3. Generally, left atrial pressure may be significantly predictive of heart failure, such as up two weeks before manifestation of heart failure. For example, increases in left atrial pressure, and both diastolic and systolic heart failure, may occur weeks prior to hospitalization, and therefore knowledge of such increases may be used to predict the onset of congestive heart failure.

Cardiac pressure monitoring, such as left atrial pressure monitoring, can provide a mechanism to guide administration of medication to treat and/or prevent congestive heart failure. Such treatments may advantageously reduce hospital readmissions and morbidity, as well as provide other benefits. An implanted pressure sensor in accordance with embodiments of the present disclosure may be used to predict heart failure up two weeks or more before the manifestation of symptoms or markers of heart failure (e.g., dyspnea). When heart failure predictors are recognized using cardiac pressure sensor embodiments in accordance with the present disclosure, certain prophylactic measures may be implemented, including medication intervention, such as modification to a patient's medication regimen, which may help prevent or reduce the effects of cardiac dysfunction. Direct pressure measurement in the left atrium can advantageously provide an accurate indicator of pressure buildup that may lead to heart failure or other complications. For example, trends of atrial pressure elevation may be analyzed or used to determine or predict the onset of cardiac dysfunction, wherein drug or other therapy may be augmented to cause reduction in pressure and prevent or reduce further complications.

Figure 4:
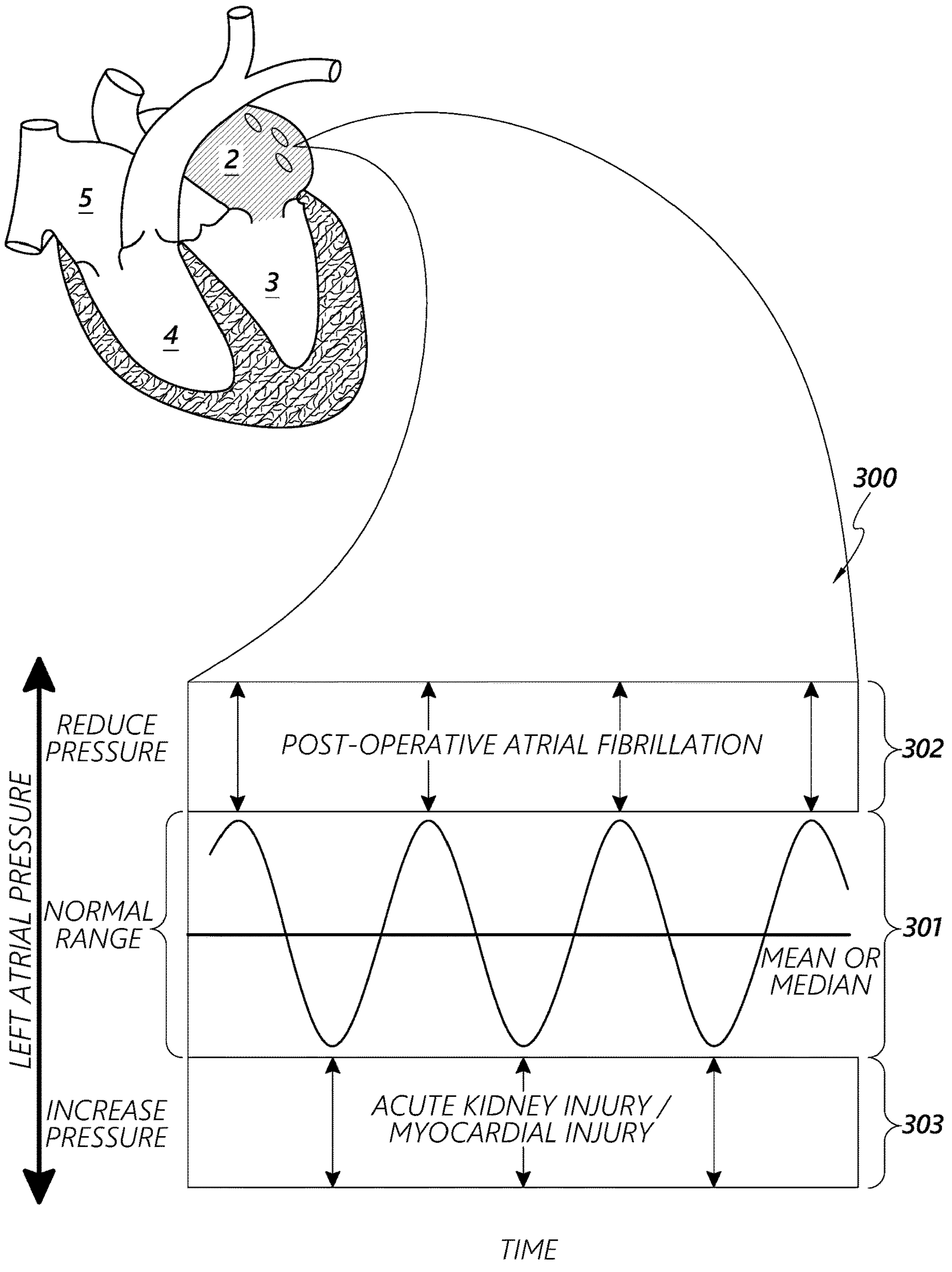
FIG. 4 illustrates a graph showing left atrial pressure ranges.

FIG. 4 illustrates a graph 300 showing left atrial pressure ranges including a normal range 301 of left atrial pressure that is not generally associated with substantial risk of postoperative atrial fibrillation, acute kidney injury, myocardial injury, heart failure and/or other health conditions. Embodiments of the present disclosure provide systems, devices, and methods for determining whether a patient's left atrial pressure is within the normal range 301, above the normal range 303, or below the normal range 302. For detected left atrial pressure above the normal range, which may be correlated with an increased risk of heart failure, embodiments of the present disclosure as described in detail below can inform efforts to reduce the left atrial pressure until it is brought within the normal range 301. Furthermore, for detected left atrial pressure that is below the normal range 301, which may be correlated with increased risks of acute kidney injury, myocardial injury, and/or other health complications, embodiments of the present disclosure as described in detail below can serve to facilitate efforts to increase the left atrial pressure to bring the pressure level within the normal range 301.

Cardiac Implant Sensor System

Embodiments of the present disclosure provide systems, devices, and methods for determining and/or monitoring fluid pressure and/or other physiological parameters or conditions in the left atrium using one or more implantable sensor devices, such as permanently implanted sensor devices. By placing a permanent sensor monitor device directly in the left atrium, embodiments of the present disclosure can advantageously allow physicians and/or technicians to gather real-time cardiac information, including left atrial pressure values and/or other valuable cardiac parameters.

Figure 5:
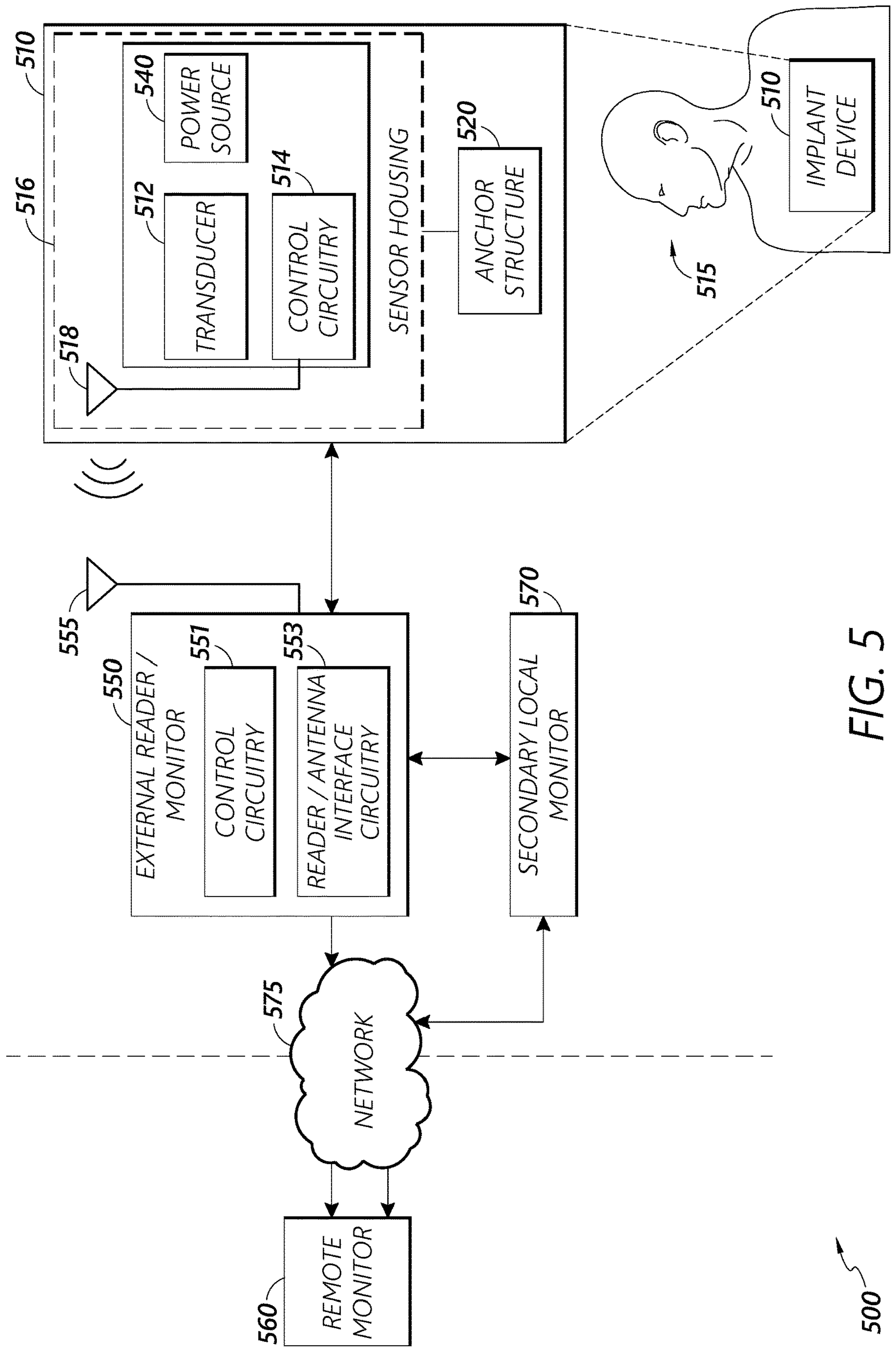
FIG. 5 shows a system for monitoring pressure and/or volume according to one or more embodiments.

Disclosed solutions for monitoring and/or controlling cardiac pressure and/or compliance in the atrial chamber(s) for the purpose of reducing the risk of heart failure and/or other health complications may be implemented in connection with a pressure-monitoring system. FIG. 5 illustrates a system 500 for monitoring pressure and/or other parameter(s) in accordance with embodiments of the present disclosure. Although the description of FIG. 5 and other embodiments herein is generally presented in the context of pressure monitoring, it should be understood that description of pressure monitoring herein is applicable to monitoring of other physiological parameters.

FIG. 5 shows a system 500 for monitoring pressure (e.g., left atrial pressure) in a patient 515 according to one or more embodiments. The patient 515 can have a pressure sensor implant device 510 implanted in, for example, the heart (not shown), or associated physiology, of the patient. For example, the sensor implant device 510 can be implanted at least partially within the left atrium of the patient's heart. The sensor implant device 510 can include one or more sensor transducers 512, such as one or more microelectromechanical system (MEMS) devices, such as MEMS pressure sensors, or the like.

In certain embodiments, the monitoring system 500 can comprise at least two subsystems, including an implantable internal subsystem or device 510 that includes the sensor transducer(s) 512 (e.g., MEMS pressure sensor(s)), as well as control circuitry 514 comprising one or more microcontroller(s), discrete electronic component(s), and one or more power and/or data transmitter(s) 518 (e.g., antennae coil). The monitoring system 500 can further include an external (e.g., non-implantable) subsystem that includes an external reader 550 (e.g., coil), which may include a wireless transceiver that is electrically and/or communicatively coupled to certain control circuitry. In certain embodiments, both the internal and external subsystems include a corresponding antenna for wireless communication and/or power delivery through patient tissue disposed therebetween. The sensor implant device 510 can be any type of implant device.

Certain details of the sensor implant device 510 are illustrated in the enlarged block 510 shown. The sensor implant device 510 can comprise anchor structure 520 as described herein. For example, the anchor structure 520 can include one or more stent-type anchors for anchoring in one or more pulmonary veins, as described in greater detail below. The anchor structure can further comprise one or more arm/bridge structures that physically couple the sensor housing 516 to one or more stents or other tissue and/or vessel anchors. Although certain components are illustrated in FIG. 5 as part of the sensor implant device 510, it should be understood that the sensor implant device 510 may only comprise a subset of the illustrated components/modules and can comprise additional components/modules not illustrated. The sensor implant device 510 includes one or more sensor transducers 512, which can be configured to provide a response indicative of one or more physiological parameters of the patient 515, such as atrial pressure and/or volume. Although pressure transducers are described, the sensor transducer(s) 512 can comprise any suitable or desirable types of sensor transducer(s) for providing signals relating to physiological parameters or conditions associated with the sensor implant device 510.

The sensor transducer(s) 512 can comprise one or more MEMS sensors, optical sensors, piezoelectric sensors, electromagnetic sensors, strain sensors/gauges, accelerometers, gyroscopes, and/or other types of sensors, which can be positioned in the patient 515 to sense one or more parameters relevant to the health of the patient. The transducer 512 may be a force-collector-type pressure sensor. In some embodiments, the transducer 512 comprises a diaphragm, piston, Bourdon tube, bellows, or other strain- or deflection-measuring component(s) to measure strain or deflection applied over an area/surface thereof. The transducer 512 may be associated with a sensor housing 516, such that at least a portion thereof is contained within, or attached to, the housing 516. The term "associated with" is used herein according to its broad and ordinary meaning. With respect to sensor devices/components being "associated with" an anchor or other implant structure, such terminology may refer to a sensor device or component being physically coupled, attached, or connected to, or integrated with, the anchor or other implant structure.

In some embodiments, the transducer 512 comprises or is a component of a piezoresistive strain gauge, which may be configured to use a bonded or formed strain gauge to detect strain due to applied pressure, wherein resistance increases as pressure deforms the component/material. The transducer 512 may incorporate any type of material, including but not limited to silicon (e.g., monocrystalline), polysilicon thin film, bonded metal foil, thick film, silicon-on-sapphire, sputtered thin film, and/or the like.

In some embodiments, the transducer 512 comprises or is a component of a capacitive pressure sensor including a diaphragm and pressure cavity configured to form a variable capacitor to detect strain due to pressure applied to the diaphragm. The capacitance of the capacitive pressure sensor may generally decrease as pressure deforms the diaphragm. The diaphragm may comprise any material(s), including but not limited to metal, ceramic, silicon or other semiconductor, and the like. In some embodiments, the transducer 512 comprises or is a component of an electromagnetic pressure sensor, which may be configured to measures the displacement of a diaphragm by means of changes in inductance, linear variable displacement transducer (LVDT) functionality, Hall Effect, or eddy current sensing. In some embodiments, the transducer 512 comprises or is a component of a piezoelectric strain sensor. For example, such a sensor may determine strain (e.g., pressure) on a sensing mechanism based on the piezoelectric effect in certain materials, such as quartz.

In some embodiments, the transducer 512 comprises or is a component of a strain gauge. For example, a strain gauge embodiment may comprise a pressure sensitive element on or associated with an exposed surface of the transducer 512. In some embodiments, a metal strain gauge is adhered to the sensor surface, or a thin-film gauge may be applied on the sensor by sputtering or other technique. The measuring element or mechanism may comprise a diaphragm or metal foil. The transducer 512 may comprise any other type of sensor or pressure sensor, such as optical, potentiometric, resonant, thermal, ionization, or other types of strain or pressure sensors.

In some embodiments, the transducer(s) 512 is/are electrically and/or communicatively coupled to the control circuitry 514, which may comprise one or more application-specific integrated circuit (ASIC) microcontrollers or chips. The control circuitry 514 can further include one or more discrete electronic components, such as tuning capacitors or the like.

In certain embodiments, the sensor transducer(s) 512 can be configured to generate electrical signals that can be wirelessly transmitted to a device outside the patient's body, such as the illustrated local external monitor system 550. In order to perform such wireless data transmission, the sensor implant device 510 can include radio frequency (RF) transmission circuitry, such as a signal processing circuitry and an antenna 518. The antenna 518 can comprise an internal antenna coil or other structure implanted within the patient. The control circuitry 514 may comprise any type of transducer circuitry configured to transmit an electromagnetic signal, wherein the signal can be radiated by the antenna 518, which may comprise one or more conductive wires, coils, plates, or the like. The control circuitry 514 of the sensor implant device 510 can comprise, for example, one or more chips or dies configured to perform some amount of processing on signals generated and/or transmitted using the device 510. However, due to size, cost, and/or other constraints, the sensor implant device 510 may not include independent processing capability in some embodiments.

The wireless signals generated by the sensor implant device 510 can be received by the local external monitor device or subsystem 550, which can include a transceiver module 553 configured to receive the wireless signal transmissions from the sensor implant device 510, which is disposed at least partially within the patient 515. The external local monitor 550 can receive the wireless signal transmissions and/or provide wireless power using an external antenna 555, such as a wand device. The transceiver 553 can include radio-frequency (RF) front-end circuitry configured to receive and amplify the signals from the sensor implant device 510, wherein such circuitry can include one or more filters (e.g., band-pass filters), amplifiers (e.g., low-noise amplifiers), analog-to-digital converters (ADC) and/or digital control interface circuitry, phase-locked loop (PLL) circuitry, signal mixers, or the like. The transceiver 553 can further be configured to transmit signals over a network 575 to a remote monitor subsystem or device 560. The RF circuitry of the transceiver 553 can further include one or more of digital-to-analog converter (DAC) circuitry, power amplifiers, low-pass filters, antenna switch modules, antennas or the like for treatment/processing of transmitted signals over the network 575 and/or for receiving signals from the sensor implant device 510. In certain embodiments, the local monitor 550 includes control circuitry 551 for performing processing of the signals received from the sensor implant device 510. The local monitor 550 can be configured to communicate with the network 575 according to a known network protocol, such as Ethernet, Wi-Fi, or the like. In certain embodiments, the local monitor 550 is a smartphone, laptop computer, or other mobile computing device, or any other type of computing device.

In certain embodiments, the sensor implant device 510 includes some amount of volatile and/or non-volatile data storage. For example, such data storage can comprise solid-state memory utilizing an array of floating-gate transistors, or the like. The control circuitry 514 may utilize data storage for storing sensed data collected over a period of time, wherein the stored data can be transmitted periodically to the local monitor 550 or another external subsystem. In certain embodiments, the sensor implant device 510 does not include any data storage. The control circuitry 514 is configured to facilitate wireless transmission of data generated by the sensor transducer(s) 512, or other data associated therewith. The control circuitry 514 may further be configured to receive input from one or more external subsystems, such as from the local monitor 550, or from a remote monitor 560 over, for example, the network 575. For example, the sensor implant device 510 may be configured to receive signals that at least partially control the operation of the sensor implant device 510, such as by activating/deactivating one or more components or sensors, or otherwise affecting operation or performance of the sensor implant device 510.

The one or more components of the sensor implant device 510 can be powered by one or more power sources 540. Due to size, cost and/or electrical complexity concerns, it may be desirable for the power source 540 to be relatively minimalistic in nature. For example, high-power driving voltages and/or currents in the sensor implant device 510 may adversely affect or interfere with operation of the heart or other anatomy associated with the implant device. In certain embodiments, the power source 540 is at least partially passive in nature, such that power can be received from an external source wirelessly by passive circuitry of the sensor implant device 510. Examples of wireless power transmission technologies that may be implemented include but are not limited to short-range or near-field wireless power transmission, or other electromagnetic coupling mechanism (s). For example, the local monitor 550 may serve as an initiator that actively generates an RF field that can provide power to the sensor implant device 510, thereby allowing the power circuitry of the implant device to take a relatively simple form factor. In certain embodiments, the power source 540 can be configured to harvest energy from environmental sources, such as fluid flow, motion, pressure, or the like. Additionally or alternatively, the power source 540 can comprise a battery, which can advantageously be configured to provide enough power as needed over the relevant monitoring period.

In some embodiments, the local monitor device 550 can serve as an intermediate communication device between the sensor implant device 510 and the remote monitor 560. The local monitor device 550 can be a dedicated external unit designed to communicate with the sensor implant device 510. For example, the local monitor device 550 can be a wearable communication device, or other device that can be readily disposed in proximity to the patient 515 and/or sensor implant device 510. The local monitor device 550 can be configured to continuously, periodically, or sporadically interrogate the sensor implant device 510 in order to extract or request sensor-based information therefrom. In certain embodiments, the local monitor 550 comprises a user interface, wherein a user can utilize the interface to view sensor data, request sensor data, or otherwise interact with the local monitor system. 550 and/or sensor implant device 510.

The system 500 can include a secondary local monitor 570, which can be, for example, a desktop computer or other computing device configured to provide a monitoring station or interface for viewing and/or interacting with the monitored cardiac data. In an embodiment, the local monitor 550 can be a wearable device or other device or system configured to be disposed in close physical proximity to the patient and/or sensor implant device 510, wherein the local monitor 550 is primarily designed to receive/transmit signals to and/or from the sensor implant device 510 and provide such signals to the secondary local monitor 570 for viewing, processing, and/or manipulation thereof. The external local monitor system 550 can be configured to receive and/or process certain metadata from or associated with the sensor implant device 510, such as device ID or the like, which can also be provided over the data coupling from the sensor implant device 510.

The remote monitor subsystem 560 can be any type of computing device or collection of computing devices configured to receive, process and/or present monitor data received over the network 575 from the local monitor device 550, secondary local monitor 570, and/or sensor implant device 510. For example, the remote monitor subsystem 560 can advantageously be operated and/or controlled by a healthcare entity—such as a hospital, doctor, or other care entity associated with the patient 515.

In certain embodiments, the antenna 555 of the external monitor system 550 comprises an external coil antenna that is matched and/or tuned to be inductively paired with the antenna 518 of the internal implant 510. In some embodiments, the sensor implant device 510 is configured to receive wireless ultrasound power charging and/or data communication between from the external monitor system 550. As referenced above, the local external monitor 550 can comprise a wand or other hand-held reader.

In some embodiments, at least a portion of the transducer 512, control circuitry 514, power source 540 and/or the antenna 518 is at least partially disposed or contained within the sensor housing 516, which may comprise any type of material, and may advantageously be at least partially hermetically sealed. For example, the housing 516 may comprise glass or other rigid material in some embodiments, which may provide mechanical stability and/or protection for the components housed therein. In some embodiments, the housing 516 is at least partially flexible. For example, the housing may comprise polymer or other flexible structure/material, which may advantageously allow for folding, bending, or collapsing of the sensor 510 to allow for transportation thereof through a catheter or other percutaneous introducing means.

The sensor implant device 510 may be implanted in any location in the body the patient 515. In some embodiments of the present disclosure, the sensor implant device 510 is advantageously implanted in the heart of the patient 515, such as in or near the left atrium of the heart, as described in detail herein. Placement of the sensor implant device 510 at least partially within the left atrium can advantageously provide a desirable location for measuring and/or monitoring left atrial pressure, blood viscosity, temperature, and/or other cardiac crammer(s). Sensor implant devices in accordance with one or more embodiments of the present disclosure may be implanted using transcatheter procedures, or any other percutaneous procedures. Alternatively, sensor implant devices in accordance with aspects of the present disclosure may be placed during open-heart surgery (e.g., sternotomy), mini-sternotomy, and/or other surgical operation.

The various embodiments shown in the accompanying figures and described herein include various features. It should be understood that a given embodiment may not include all of the features illustrated or described in connection with the embodiment and may include one or more additional features shown or described in connection with one or more other embodiments. That is, the features of the illustrated and/or described embodiments of the present disclosure may be combined in any desired combination in an embodiment within the scope of the present disclosure.

Figure 6:
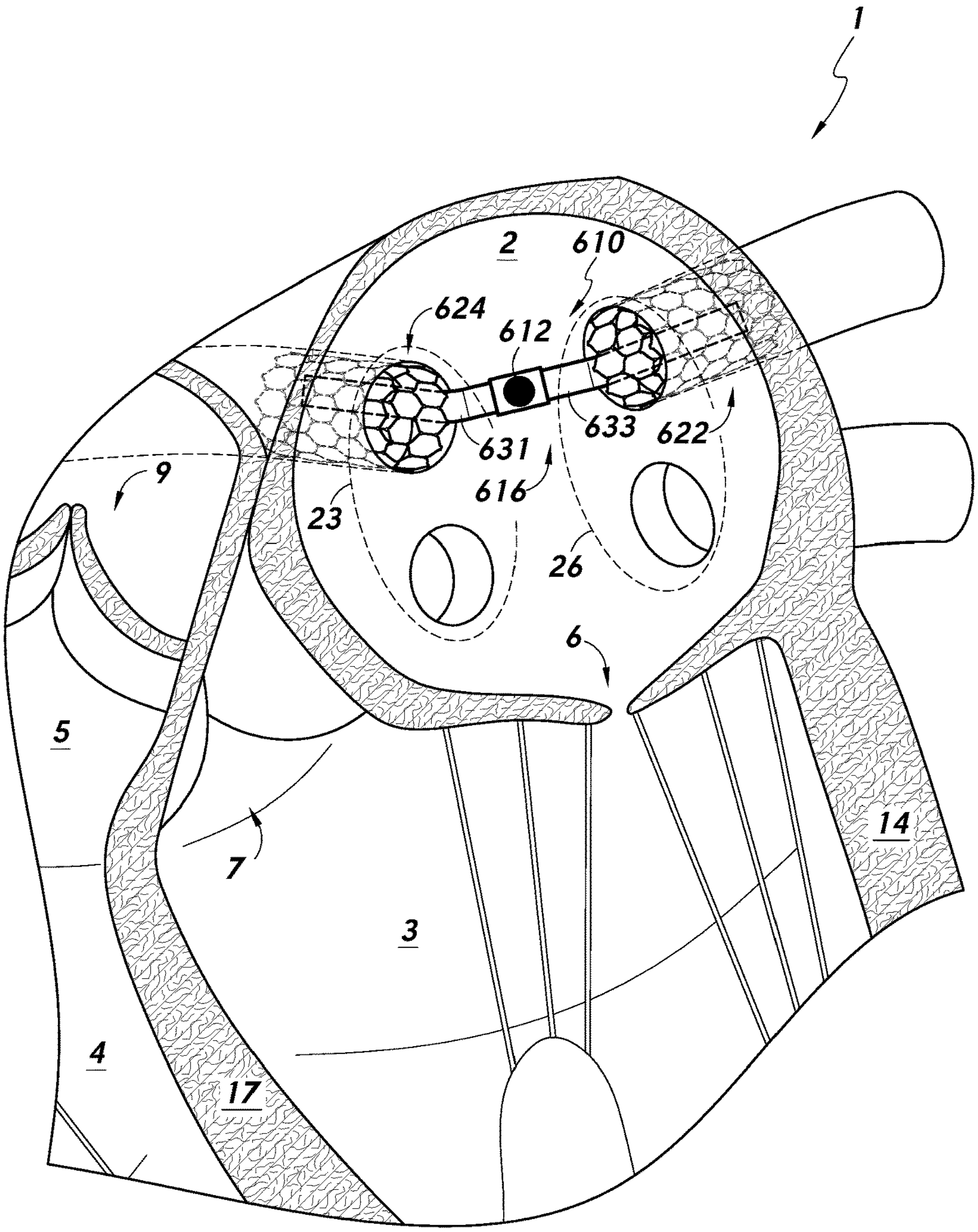
FIG. 6 illustrates a heart having a sensor implant device implanted therein in accordance with one or more embodiments.

In some of the figures accompanying the present disclosure, certain reference numbers may be re-used as a matter of convenience for devices and modules having features that are similar in one or more respects. However, re-use of common reference numbers in the drawings does not necessarily indicate that such features, devices, components, or modules are identical, Sensor Implant Devices and Methods The diagram of FIG. 6 shows the sensor implant device 610 implanted at least partially within the left atrium 2, such that a sensor component 616 thereof may advantageously be positioned and/or disposed to determine or acquire sensor signals indicative of one or more physiological parameters associated with the sensor device 610 and/or left atrium 2. In some implementations, the sensor implant device 610 may advantageously be anchored to one or more anatomical features/locations associated with the left atrium 2. For example, the sensor implant device 610 may comprise one or more anchors and/or other features configured to be anchored at, in, or near one or more of the left 26 and/or right 23 pulmonary veins. With the sensor component 616, which may advantageously comprise or be associated with a sensor transducer/element 612, at least partially exposed within the left atrium 2, the sensor component 616 may be able to measure various cardiac parameter(s), including but not limited to left atrial pressure, blood viscosity, temperature, and/or others.

In some implementations, the sensor implant device 610 comprises a first anchor 622, which may be a stent-type anchor configured to be expanded to provide a friction fit with in the ostium and/or vessel associated with a first pulmonary vein, as shown. The sensor implant device 610 can further comprise a second anchor 624, which may be configured and/or designed to be implanted to/in an ostium or vessel associated with a second pulmonary vein, as shown. For example, the anchor 624 may comprise a stent-type anchor, or a barb-type or other type of anchor configured to be embedded at least partially within biological tissue at or near a target implantation location.

The sensor implant device 610 further comprises one or more arms or support structures, which may be used to position the sensor component 616 in a desired implant position and/or secure the sensor component 616 to one or more anchor features of the sensor implant device 610. For example, as shown, the arm portion 633 can advantageously secure the sensor component 616 to the first anchor 622, whereas the arm portion 631 may support or secure the sensor component 616 to the second anchor feature 624.

Figure 7:
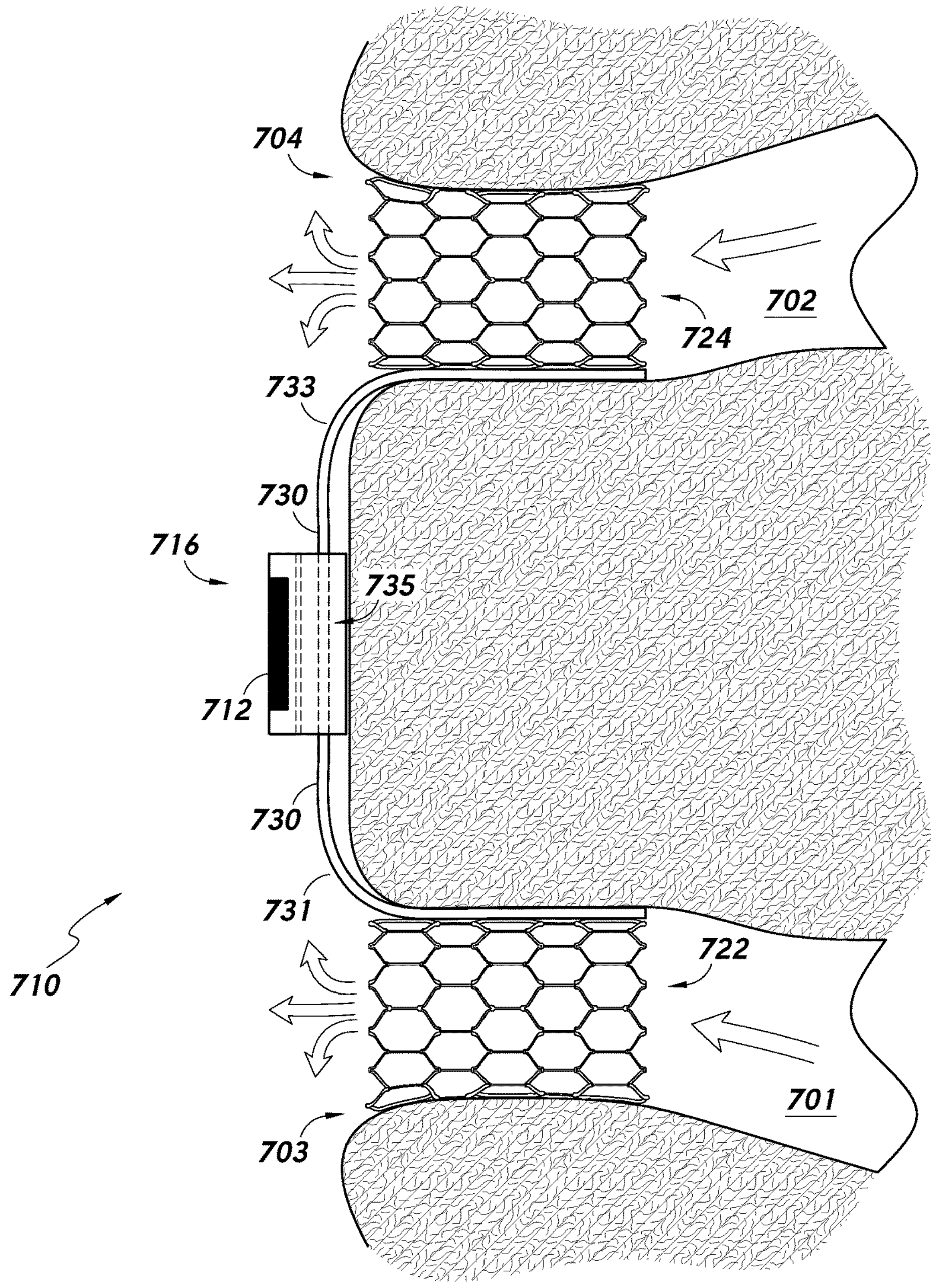
FIG. 7 shows a side view of a sensor implant device in accordance with one or more embodiments.

FIG. 7 shows a sensor implant device 710 implanted in one or more vessels 701, 702 of patient anatomy, such as cardiac anatomy, as described in detail herein. The sensor implant device 710 advantageously comprises a sensor element, unit, and/or module 716, which may have a sensor transducer element 712 associated therewith. For example, the sensor transducer element 712 may advantageously be disposed and/or attached at an outward-facing face or surface of the sensor module 716, such that physiological parameters associated with the environment to which the outward-facing surface of the sensor module 716 is exposed can be determined and/or translated by the sensor transducer 712 to a form that can be interpreted and/or indicative of one or more physiological parameters associated with the implantation site of the sensor implant device 710. The sensor module 716 may be anchored order implanted/secured in any suitable or desirable way or manner. For example, in some embodiments of the present disclosure, sensor elements are physically, and mechanically coupled to one or more anchor devices by one or more arm or bridge features 730. For example, the illustrated implant device 710 includes a first arm member portion 731, as well as a second arm or member portion 733, each of which may be coupled to a respective anchor device, as shown. In some embodiments, the arm member portions 731, 733 are part of a single unitary form or structure. That is, the sensor module 716 may advantageously be mechanically or physically coupled to a bridge structure 730, wherein portions of such bridge structure on respective sides of the sensor module 716 are called-out in FIG. 7 as arm member portions 731, 733, respectively.

The implant device 710, as referenced above, may advantageously comprise one or more anchor devices configured to be anchored in or to a vessel or conduit, such as a blood vessel and/or associated ostium, or the like. Certain embodiments of the present disclosure are described in the context of stent-type anchor devices, which are illustrated as example conduit anchors in FIG. 7 as well as other example Figures associated with the present disclosure. As described in detail herein, the sensor implant device 710 may be anchored to and/or within one or more pulmonary veins and/or other cardiac blood vessel(s) to advantageously secure the sensor module 716 in a position exposed at least partially within the left atrium and/or other chamber of the heart in some implementations. For example, the vessel 701 may represent a first pulmonary vein, whereas the vessel 702 may represent a second pulmonary vein. In some implementations, a first anchor device associated with a sensor implant device may be implanted or anchored to a pulmonary vein, whereas a second anchor device associated with the sensor implant device may be implanted or anchored in another manner/configuration, such as by embedding into tissue, or the like.

Although some embodiments disclosed herein describe stent-type anchor device(s), it should be understood that any types/configurations of anchor devices may be implemented in accordance with embodiments of the present disclosure. For example, in some embodiments, other expansive anchor forms or devices may be implemented, such as pre-shaped wireforms, struts, clips, and/or other anchor device(s). The use of stent-type anchors, as described in detail herein, can advantageously allow for blood flow to flow within the pulmonary vein(s) through the anchor(s) into the left atrium, such that the functionality/flow of the pulmonary vein(s) is not substantially impacted or obstructed. In some embodiments, opposing clips or arms configured to present outward and/or inward radial force with respect to one another may be utilized to secure a sensor implant device in accordance with embodiments of the present disclosure in a desired position/place. For example, the illustrated anchor devices 722, 724 may each provide outward radial force relative to a central axis of the respective anchor device to secure the respective implant device within the target vessel in which it is implanted. Furthermore, each of the arm portions 731, 733 may further be pre-shaped and/or otherwise configured to present an outward and/or inward radial force to further secure the implant device 710 in the desired position as secured to the vessel 701, 702.

One or both of the anchor devices 722, 724 may advantageously be at least partially self-expanding, which may provide a relatively simple deployment process for deploying respective anchors. Additionally or alternatively, one or both of the anchor devices 722, 724 may be balloon-expandable and/or expandable using another means or mechanism. Although two anchor devices are shown in FIG. 7 and in certain other Figures associated with the present disclosure, it should be understood that in some embodiments of the sensor implant device 710 is associated with one anchor device, or more than two anchor devices. For example, some important notations, the sensor implant device 710 has three or more anchor devices, each of which is associated with a separate arm/member portion secured indirectly or directly to the sensor module 716 in any suitable or desirable manner.

Figure 8:
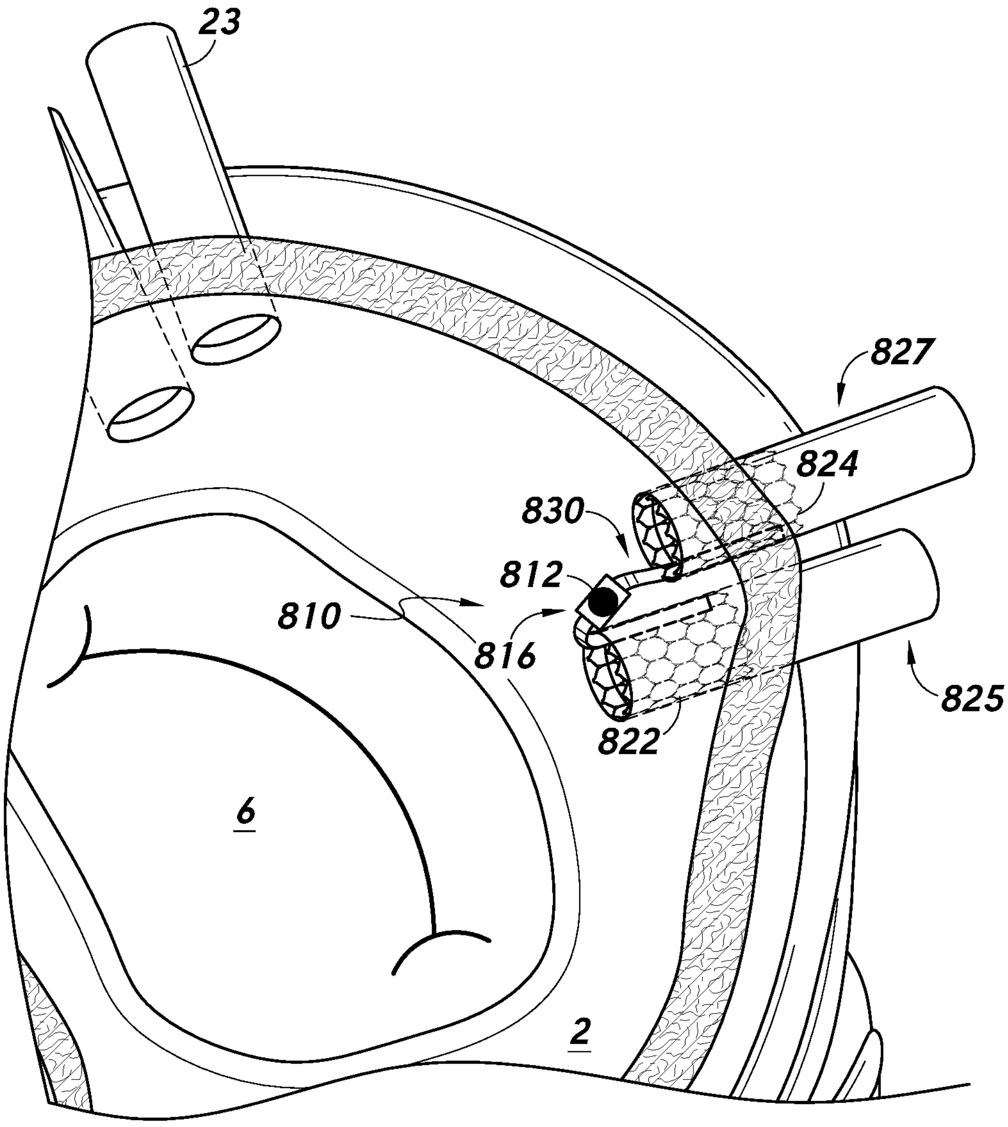
FIG. 8 shows a sensor implant device including anchor features engaged in a plurality of pulmonary veins in accordance with one or more embodiments.

FIG. 8 shows a top-down view of a left atrium 2 having implanted therein a sensor implant device 810 in accordance with one or more embodiments of the present disclosure. The sensor implant device 810 shown in FIG. 8 includes various features that may be incorporated in any of the disclosed embodiments. For example, the sensor implant device 810 can include a sensor component 816, arm member(s)/structure(s) 830, and/or anchors 822, 824, as described in detail herein.

As described in detail herein, tissue-anchoring components or portions of a sensor implant device in accordance with embodiments of the present disclosure may comprise any suitable or desirable form or mechanism, including any known tissue-anchoring devices or mechanisms. In the illustrated embodiment of FIG. 8, the sensor implant device 810 advantageously includes expandable anchors 822, 824 associated with proximal and distal end portions of the sensor implant device 810. One or both of the anchors 822, 824 may be tension-/resistance-type anchors, such as a stent or similar structure or device. For example, one or both of the anchors 822, 824 may be expanded within a respective pulmonary vein 825, 827, as shown.

In implementations in which the sensor implant device 810 is anchored to more than one pulmonary vein, as in FIG. 8, the bridge/arm member(s)/structure(s) 830 may be configured to be span the distance between pulmonary veins (e.g., adjacent pulmonary veins 822, 824) and/or ostia thereof, as shown. The bridge/arm member(s)/structure(s) 830 may be configured to provide inward radial force with respect to the axis of one or both of the anchors 822, 824 to thereby provide additional anchoring of the sensor implant device 810 to the pulmonary veins.

In FIG. 8, a first anchor stent 822 is deployed in a first pulmonary vein 827, wherein the stent 822 is associated with and/or coupled to an end portion of the bridge/arm structure 830 in accordance with embodiments of the present disclosure. The first anchor 822 is coupled to the secondary anchor 824, which is deployed within the adjacent pulmonary vein 824, wherein the first and second anchors 822, 82.4 are coupled to one another by the bridge or arm member(s) 830, which may be at least partially rigid and/or flexible. In some embodiments, the bridge/arm member(s) 830 has/have shape memory and/or resilience characteristics that introduce a force on the anchors 822, 824 towards one another. Either or both of the anchors 822, 824 may be self-expanding stents. Use of two anchors may serve to provide improved anchoring for a sensor implant device in accordance with embodiments of the present disclosure.

Figure 9A:
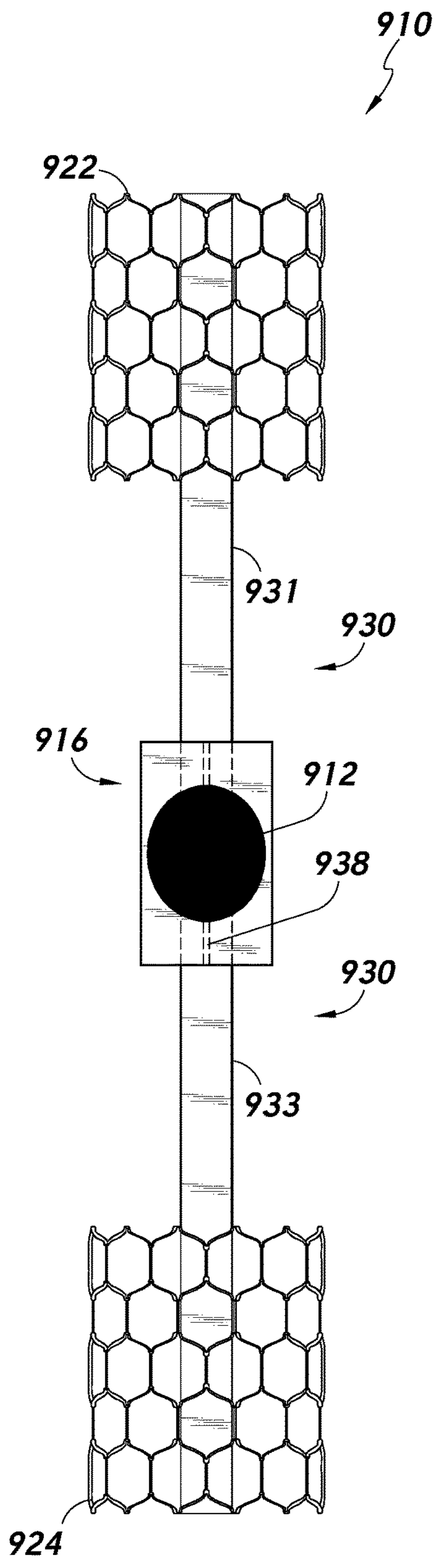
FIGS. 9A and 9B show front and side views, respectively, of a sensor implant device in an expanded configuration in accordance with one or more embodiments.
Figure 9B:
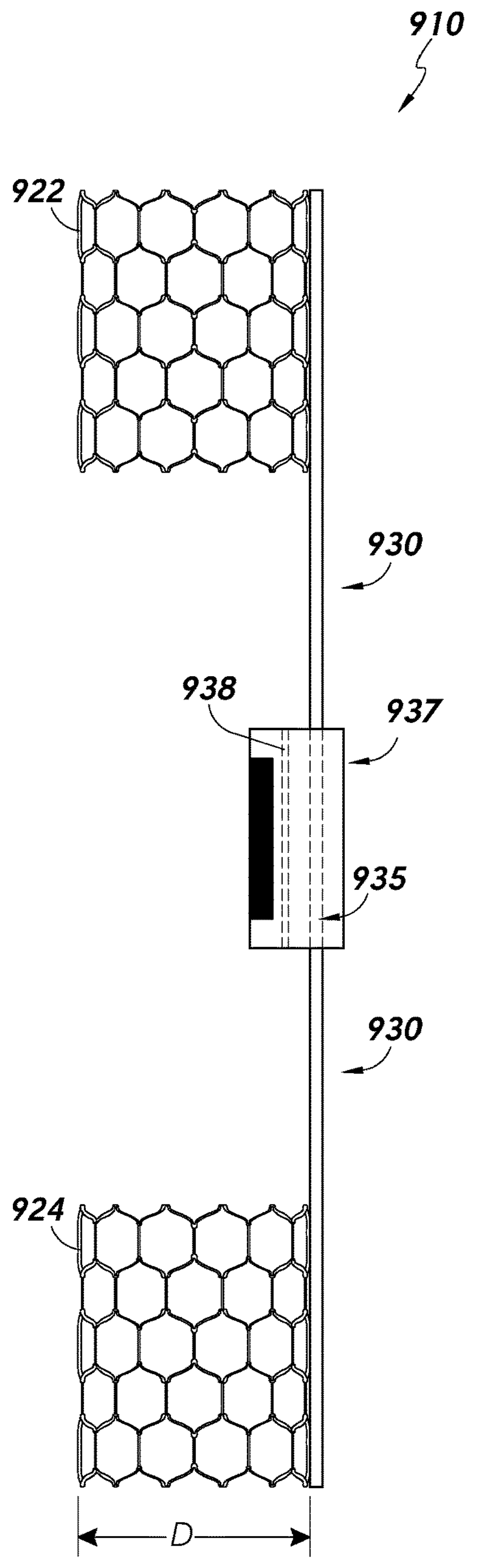

FIGS. 9A and 9B illustrate front and side views, respectively, of a sensor implant device 910 in accordance with one or more embodiments of the present disclosure. In the configuration illustrated in FIGS. 9A and 9B, anchor devices 922, 924 associated with the implant device 910 are in an expanded state or configuration, wherein the anchor devices may be configured to be secured within a target implantation vessel, such as a pulmonary vein, using force exerted by the respective anchor devices in the illustrated expanded configuration. For example, the anchors 922, 924 can advantageously have an expanded configuration with a diameter or other dimension D that is dimensioned to be approximately equal to, or slightly greater than, a diameter of a pulmonary vein lumen at one or more longitudinal portions thereof.

The anchor devices 922, 924 can advantageously be self-expanding, or may be balloon-expanding, or otherwise configurable or expanded for securing within a blood vessel, such as a pulmonary vein. Similarly to other embodiments illustrated and described herein, the anchor devices 922, 924 may each be physically/mechanically coupled to a sensor module 916 using any suitable or desirable direct and/or indirect attachment mechanism. In the illustrated embodiment of FIGS. 9A and 9B, the anchor devices are secured at least partially to the sensor module 916 (e.g., housing of the sensor transducer element 912) by one or more arm portions/members 931, 933, respectively. As with any of the other embodiments disclosed herein, the various illustrated and called-out arm portions 931, 933 may be part of a single bridge/arm structure, to which the sensor module 916 is directly and/or indirectly secured.

The sensor module 916 may comprise a housing for the sensor transducer element 912. For example, the sensor transducer element 912 may be nested in, secured to, and otherwise attached or coupled with one or more portions of the bridge structure 930. In some embodiments, the sensor module 916 has associated therewith a channel, groove, and/or path 938 configured and/or dimensioned for holding or otherwise coupling a guidewire or other delivery system component therein. For example, in some implementations, a guidewire may be extended or advanced through a channel or other pathway or feature associated with the module 916, such that the sensor implant device 910 can be advanced along a path defined by a pre-disposed guidewire in accordance with procedures associated with aspects of the present disclosure. Additionally or alternatively, the module 916 may comprise one or more features configured and/or designed to allow for coupling of the module 916 with one or more portions of the bridge structure 930. Although stent-type anchor devices 922, 924, are shown, which may be understood to represent self-expanding stent anchor devices in some implementations, the anchor devices 922, 924 may be any type of anchor device as described herein.

Figure 10A:
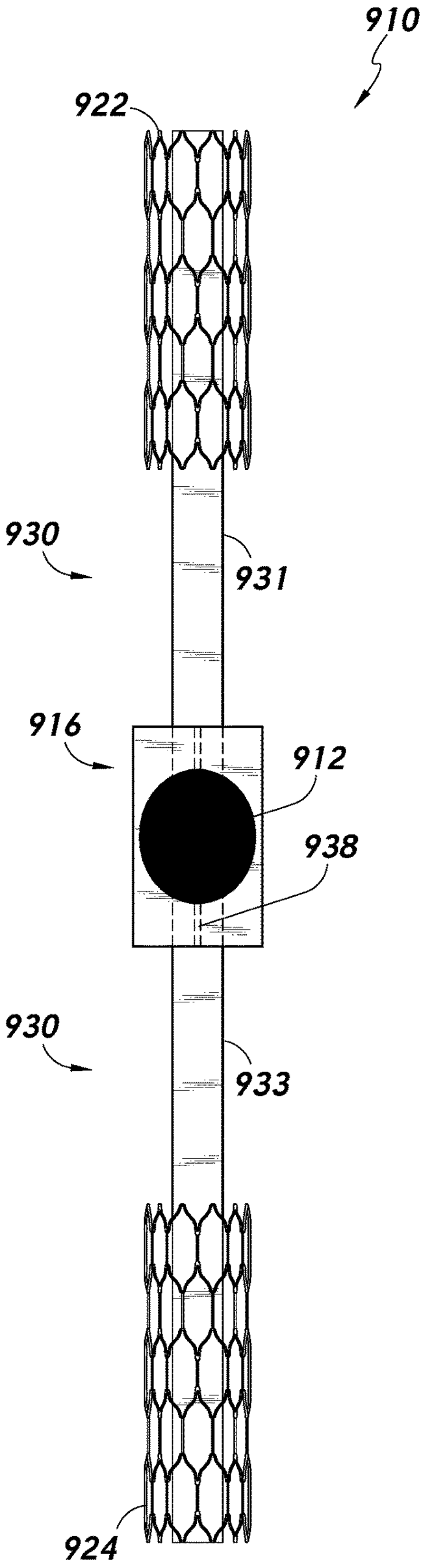
FIGS. 10A and 10B show front and side views, respectively, of a sensor implant device in a compressed configuration in accordance with one or more embodiments.
Figure 10B:
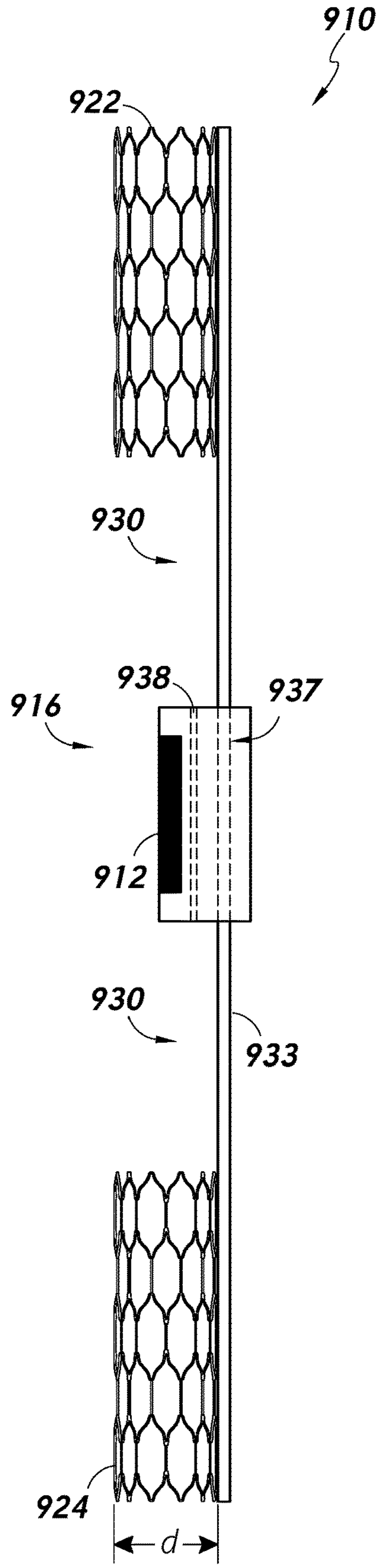

FIGS. 10A and 10B illustrate front and side views, respectively, of the sensor implant device 910 shown in FIGS. 9A and 9B, wherein one or more components of the sensor implant device 910 are configured in a collapsed or crimped state, which may be implemented in order to facilitate delivery of the implant device 910 using a catheter-based delivery system, as described in greater detail below. Specifically, the embodiments shown in FIGS. 10A and 10B show stent-type anchor devices 922, 924 in an at least partially collapsed/crimped state. For example, the stent anchor devices, or other types of anchor devices, may comprise a wireframe or other wire- and/or mesh-type structure that may assume a crimped and/or reduced-diameter state by compression thereof and/or elongation of the structure. For example, such compression may be achieved by compressing or expanding expandable strut features of the anchor(s) radially, axially, and/or circumferentially. In some embodiments, such compression/expansion of struts may result in an at least partial elongation of the stent structure with respect to a central axis thereof. The compressed anchors 922, 924 may have a compressed diameter d that is less the expanded diameter D.

Figure 11:
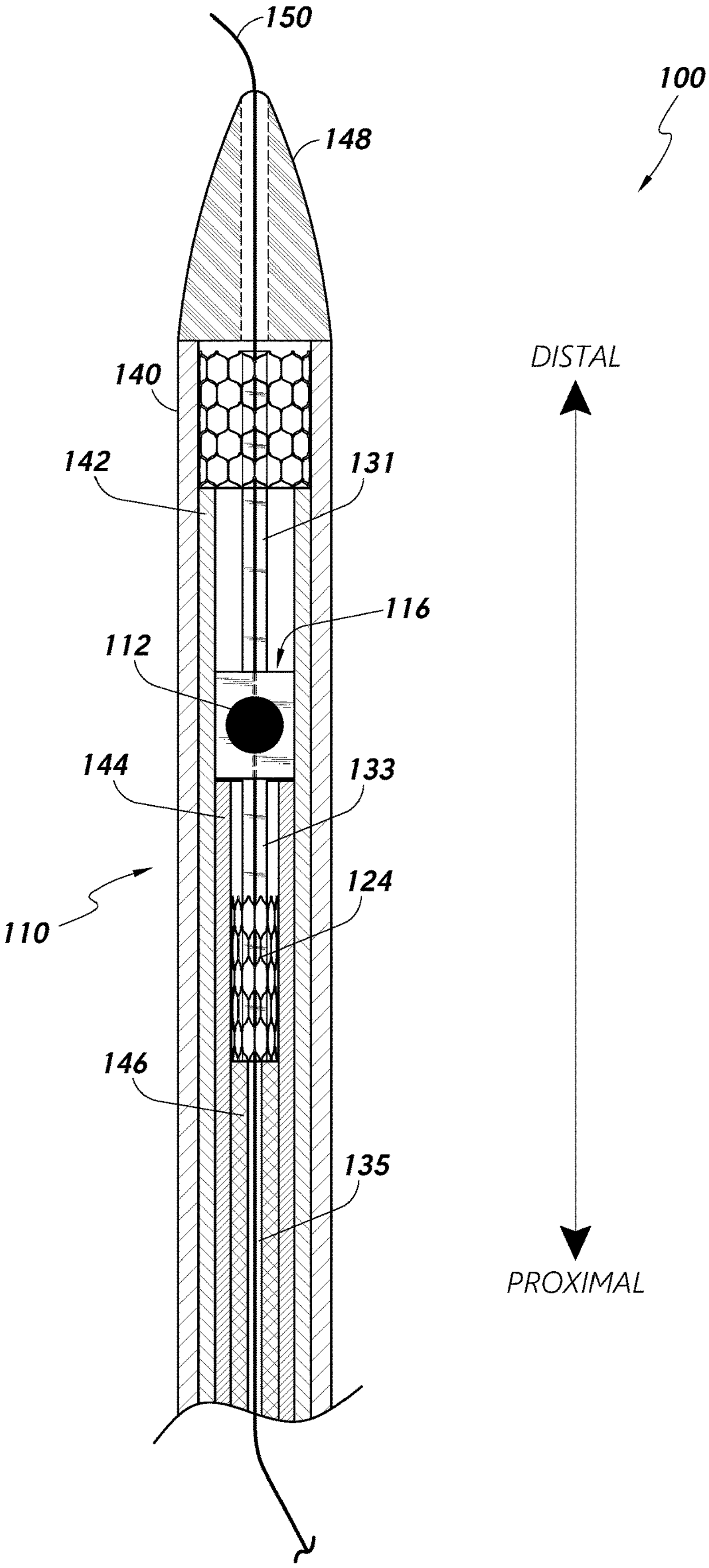
FIG. 11 shows a cross-sectional view of a delivery system for a sensor implant device in accordance with one or more embodiments.

FIG. 11 shows a partial cross-sectional view of a delivery system 100 for a sensor implant device 110 in accordance with one or more embodiments of the present disclosure. In some embodiments, the delivery system 100 comprises one or more catheters or sheaths used to advance and/or implant the sensor implant device 110, which may be disposed at least partially within the delivery system 100 during a delivery process associated therewith. The implant sensor device 110 can be positioned within the delivery system 100 with a first end thereof (i.e., distal anchor 122) disposed distally with respect to the sensor module 116, whereas a second/proximal anchor 124 is positioned at least partially proximately with respect to the sensor module 116. The distal 122 and proximal 124 anchor devices may be coupled to the sensor module 116 via one of the securing arm portions 131, 133, respectively.

In some embodiments, the delivery system 100 comprises an outer catheter or shaft 140, which may be used to transport the sensor implant device 110 to the target implantation site. That is, the sensor implant device 110 may be advanced to the target implantation site at least partially within a lumen of the outer shaft 140, such that the sensor implant device 110 is held and/or secured at least partially within a distal portion of the outer shaft 140. In some embodiments, the delivery system 100 comprises a tapered nosecone feature 148, which may facilitate advancement of the distal end of the delivery system 100 through the tortuous anatomy of the patient and/or with an outer delivery sheath or other conduit/path. The nosecone 148 may be a separate component from the outer shaft 140 or may be integrated with the outer shaft 140. In some embodiments, the nosecone 148 is adjacent to and/or integrated with a distal end of the outer shaft 140. In some embodiments, the nosecone is distally tapered into a generally-conical shape and may comprise and/or be formed of multiple flap-type forms that can be urged/spread apart when the sensor implant device 110 and/or any portions thereof, interior shafts, or devices are advanced therethrough.

The delivery system 100 may further be configured to have a guidewire 150 disposed at least partially within the delivery system 100 and/or coupled thereto in a manner to allow the delivery system 100 to follow a path defined by the guidewire 150. The distal anchor device 122 may be contained and/or secured by the outer shaft 140, as illustrated in FIG. 11.

The delivery system 100 may further comprise a distal inner shaft 142 disposed at least partially within the outer shaft 140 and proximal to the distal anchor device 122, such that the distal inner shaft 142 can provide support for the distal anchor 122. Furthermore, the distal inner shaft 142 can be configured to be used to push/advance the distal anchor device 122, along with the remaining components of the implant device 110 coupled thereto, relative to the outer shaft 140. Therefore, by distally advancing the distal inner shaft 142 relative to the outer shaft 140, the distal anchor 122 and sensor implant device 110 can be distally advanced and/or deployed through a distal opening in the outer shaft 140. While the distal anchor device 122 is disposed at least partially without the distal inner shaft 142 and/or distal thereto, one or more other components of the sensor implant device 110 may be maintained, contained, and/or disposed at least partially within the inner shaft 142 during one or more periods of a delivery process, as illustrated in FIG. 11. For example, the sensor module 116, which may have associated therewith a sensor transducer element 112 as described in detail herein, as well as one or more portions of the bridge/arm structure 131, 133 and/or proximal anchor 124 may be contained at least partially within the distal inner shaft 142.

The delivery system 100 may further comprise a proximal inner shaft 144 disposed at least partially within the distal inner shaft 142 and outer shaft 140 and proximal to the sensor module 116, such that the proximal inner shaft 144 can provide support for the sensor module 116. Furthermore, the proximal inner shaft 144 can be configured to be used to push/advance the sensor module 116 and/or other components of the sensor implant device 110 coupled thereto relative to the distal inner shaft 142 and/or outer shaft 140. While the sensor module 116 is disposed at least partially without the proximal inner shaft 144 and/or distal thereto, one or more other components of the sensor implant device 110 may be contained or disposed at least partially within the proximal inner shaft 144 during one or more periods of a delivery process, as illustrated in FIG. 11. For example, the proximal portion 133 of the bridge/arm structure 130 and the proximal anchor device 124 may be contained at least partially within the proximal inner shaft 144. In some implementations, the proximal portion 133 of the bridge/arm structure 130 may be configured to be positioned in the proximal inner shaft 144 and/or other component(s) of the delivery system 100 in an at least partially bent configuration, such that the proximal anchor device 124 is stored within the proximal inner shaft 144 in a cramped/collapsed state and/or in a position such that the end of the proximal anchor device 124 faces distally and a similar direction as the distal anchor device 122.

The delivery system 100 may further include a proximal anchor pusher device 146 configured to be disposed against and/or contact the proximal anchor 124 and/or associated structure (e.g., arm portion 133 directly or indirectly coupled to the proximal anchor device 124) to allow for pushing and/or controlling/manipulating the proximal anchor device 124. For example, the proximal anchor pusher device 146 may comprise a tubular-shaped form defining a lumen therein, as illustrated in FIG. 11. Alternatively, in some embodiments, the proximal anchor pusher support 124 may not include an internal axial lumen, and rather may provide a substantially solid form and/or other-shaped or configured form than that illustrated in FIG. 11.

The proximal anchor pusher support 146 may be disposed and/or contained at least partially within one or more of the outer shaft 140, distal inner shaft 142 and/or proximal inner shaft 144, and further may have disposed in a lumen thereof one or more components of the sensor implant device 110 and/or delivery system 100 during various periods of an associated implantation procedure. For example, in some implementations, the guidewire 150 may be disposed at least partially within the proximal anchor pusher support 146 during one or more portions of a medical procedure for implanting the sensor implant device 110. For example, the delivery system 100 may be configured to be advanced axially along the guidewire 150 during a medical procedure, wherein the guidewire 150 may be initially placed along a path to a target implantation site, such that the delivery system can be passed over the guidewire 150. During such process(es), the guidewire 150 may be disposed within the proximal anchor pusher support and/or proximal inner shaft 144, distal inner shaft 142, and/or outer shaft 140).

Figures 1, 12:
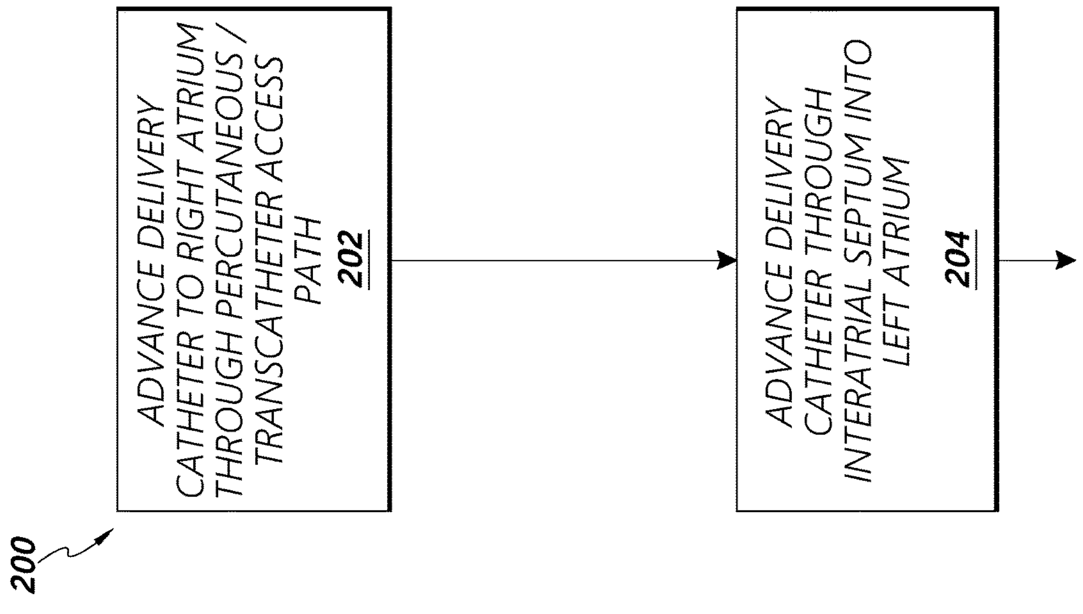
Figures 1, 13:
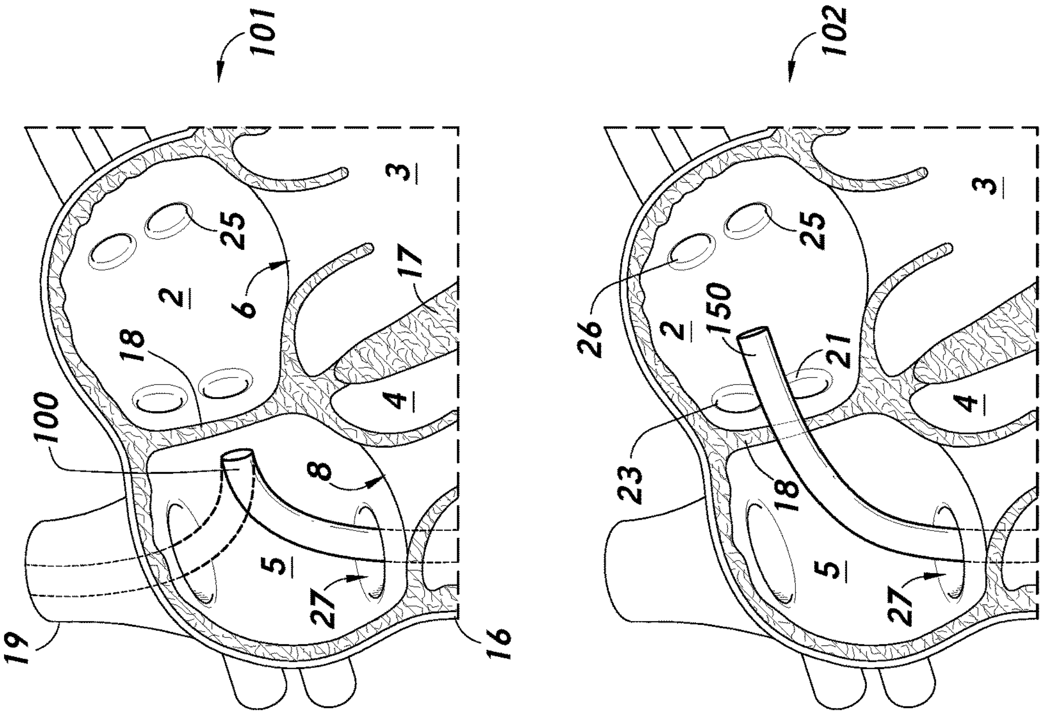
Figures 1, 14:
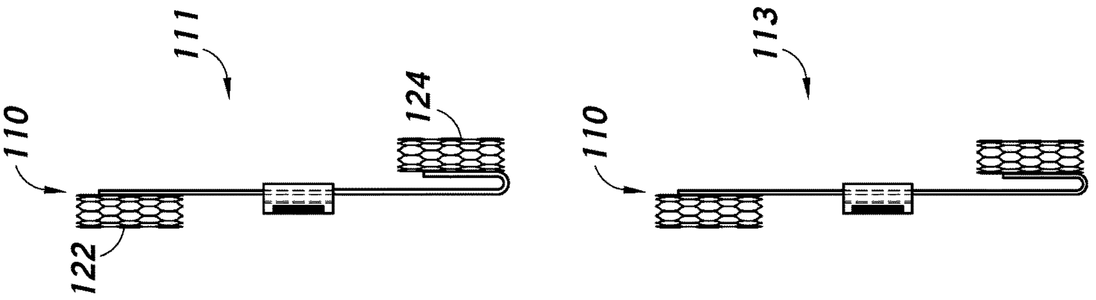
Figures 2, 12:
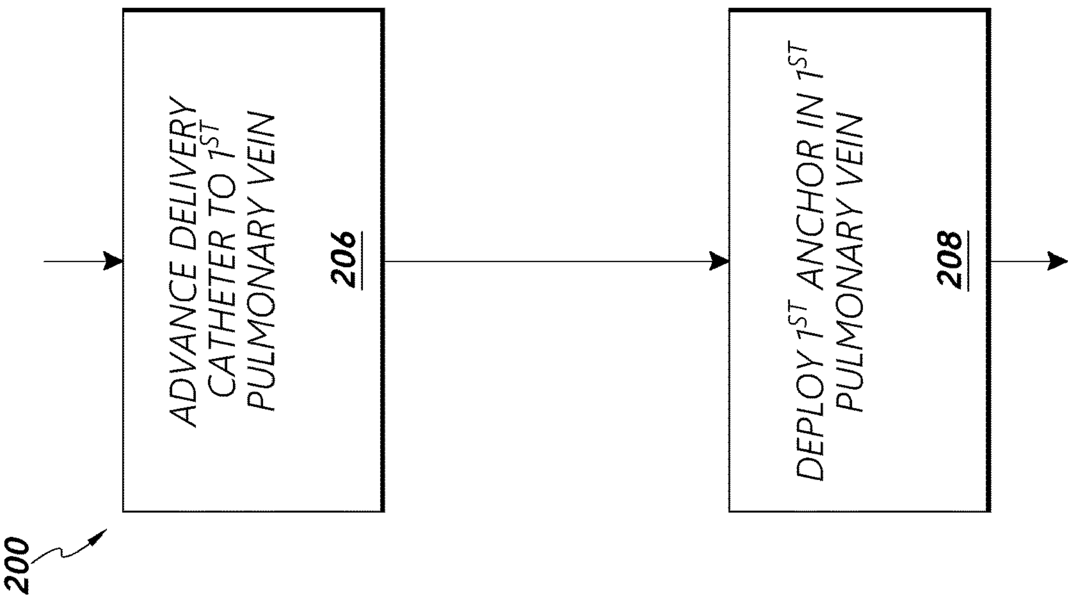
Figures 2, 13:
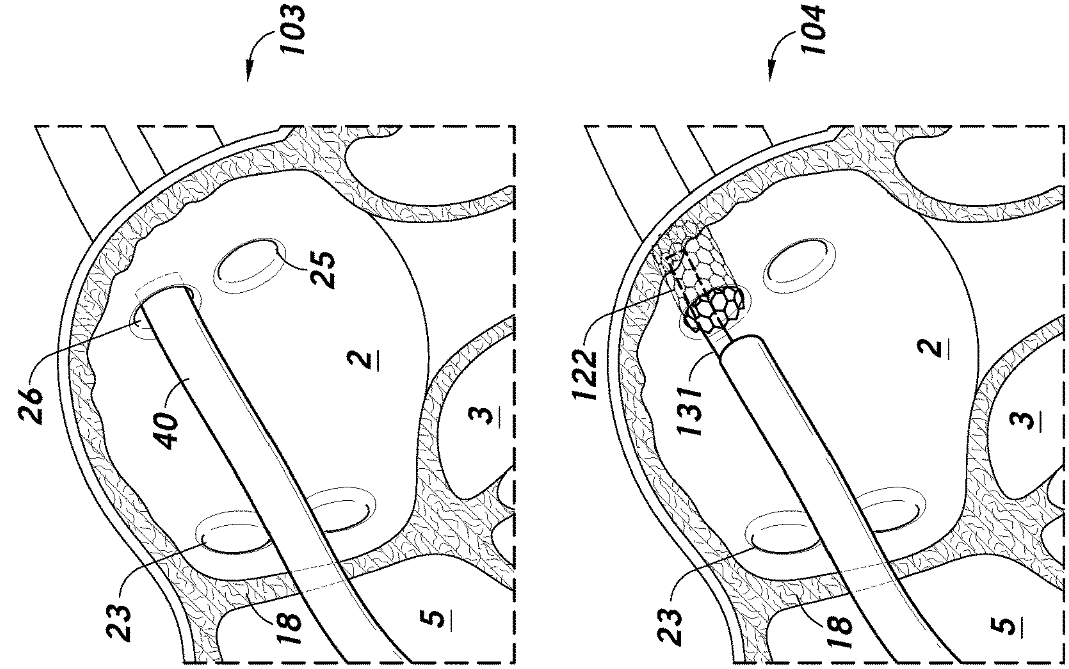
Figures 2, 14:
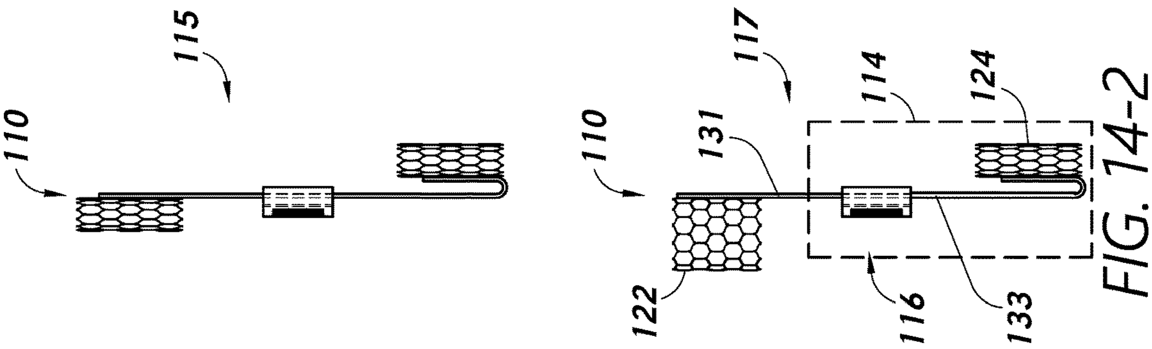
Figures 3, 14:
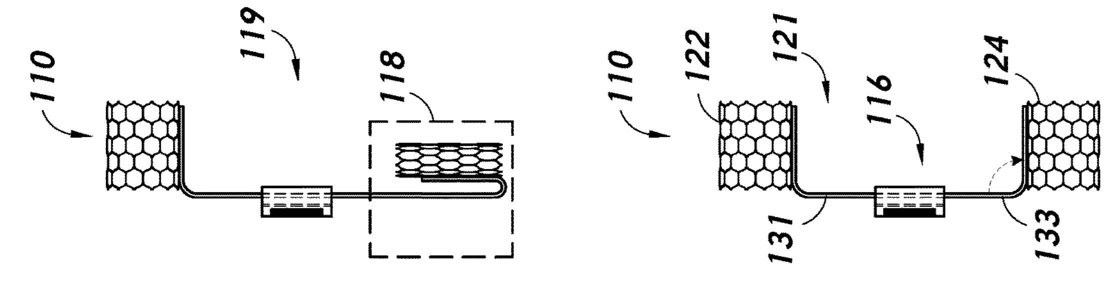
Figures 3, 13:
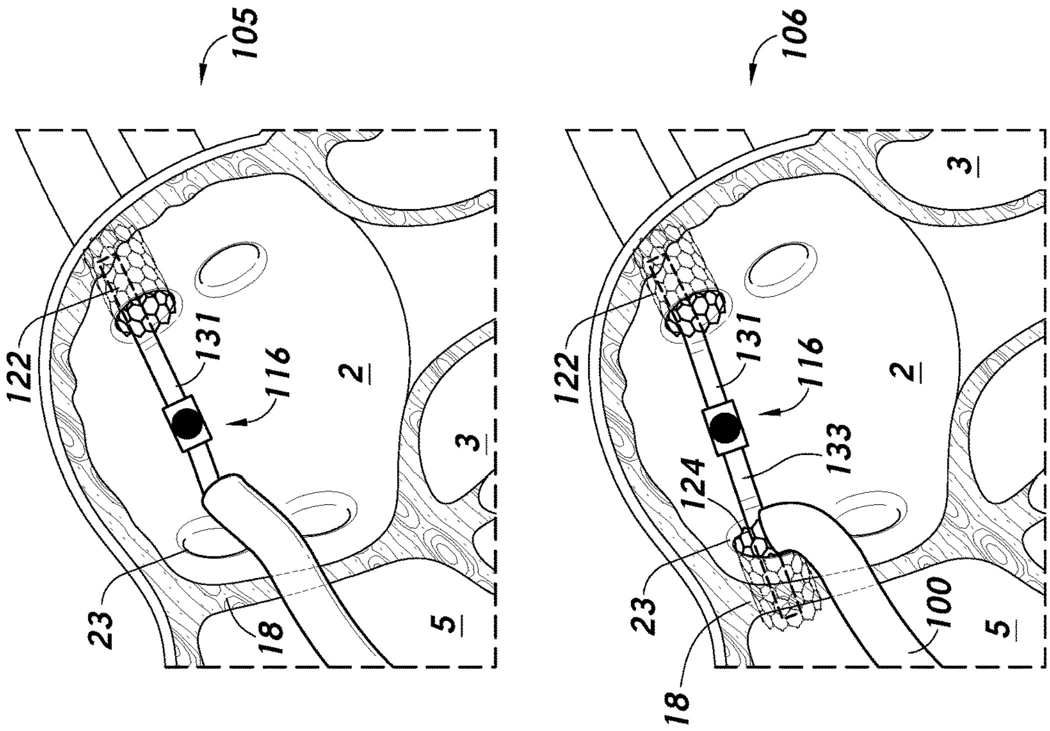
Figures 3, 12:
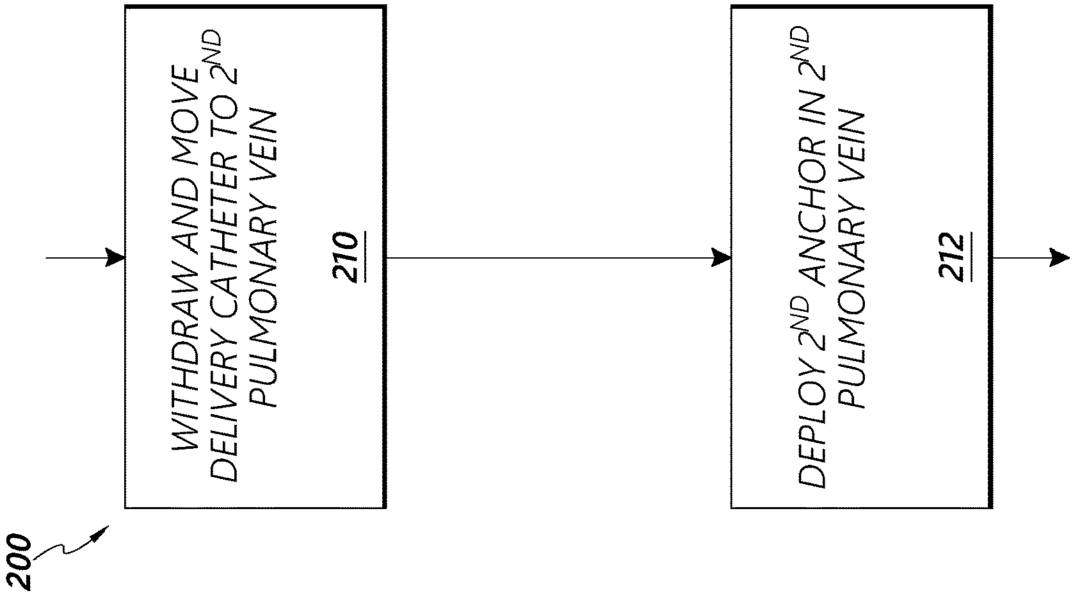
Figures 4, 12:
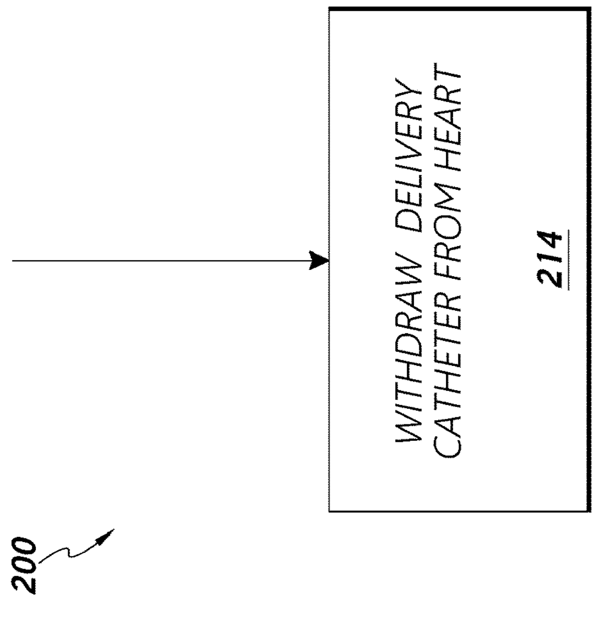
Figures 4, 13:
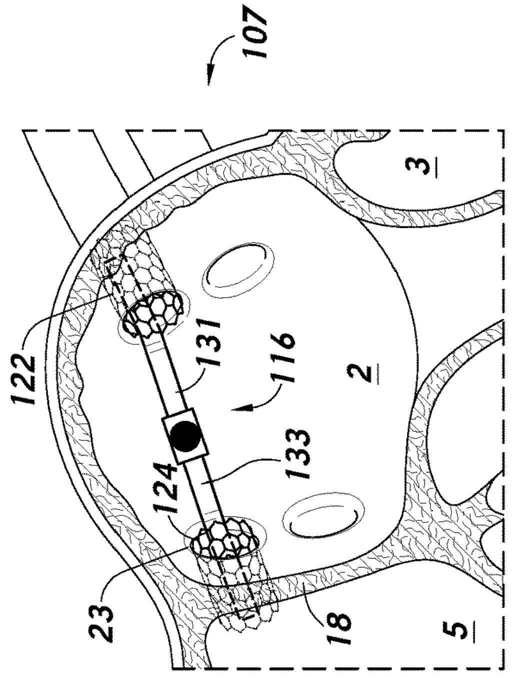
Figures 4, 14:
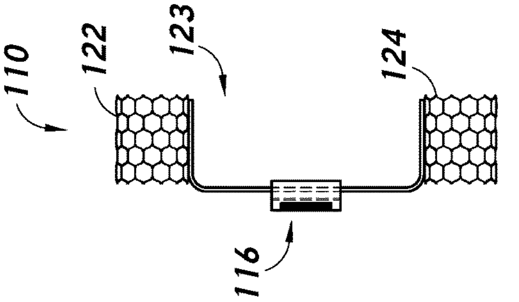

FIG. 12 is a flow diagram illustrating a process 200 for implanting a sensor implant device at or in target anatomy of a patient, such as within one or more cardiac chambers or vessels of a heart of the patient. FIG. 13 illustrates images of cardiac anatomy, as well as delivery system and sensor implant device components, corresponding to the various operations described in the flow diagram of FIG. 12, For example, FIG. 13 shows embodiments of a delivery system and sensor implant device that may represent example embodiments of the delivery system 100 and sensor implant device 110 shown in FIG. 11 and described in detail above, and therefore similar reference numbers are used for convenience. FIG. 14 illustrates front and side views, respectively, of the sensor implant device 110 in various configurations corresponding to the respective operations of the process 200 of FIG. 12.

The process 200 relates to one or more medical procedures for implanting the sensor implant device 110 at least partially within the left atrium 2 of the patient's heart using a suitable delivery system 100. In some implementations, the process 200 may be performed in connection with a mitral valve replacements or repair procedure, or another surgical or transcatheter medical procedure requiring access to the left atrium. Therefore, although certain procedure(s) are described for accessing the left atrium, it should be understood that left atrial access by a delivery system in accordance with embodiments of the present disclosure may be made in any suitable or desirable way. For example, such access may be made using a minimally invasive procedure or using a surgical procedure incorporating access to the heart through the chest wall, such as in accordance with an open-chest procedure.

At block 202, the process 200 involves advancing the delivery system/catheter 100 to the right atrium 5 of the patient's heart using a percutaneous/transcatheter access path or procedure. For example, as shown in image 302 of FIG. 13, access to the right atrium 5 may be made via the superior 19 or inferior 16 vena cavae, wherein access to the venous system may be made from the subclavian vein, femoral vein, or any other venous (or arterial) blood vessel. As shown in FIG. 14, the sensor implant device 110 may be in an at least partially collapsed/crimped configuration within the delivery system 100 when the delivery system 100 is advanced to the right atrium 5. In some embodiments, as described in detail herein, one or more of the distal 122 and/or proximal 124 anchor devices may be axially folded inward towards an axial center of the sensor implant device 110, as shown in image 111 with respect to the proximal anchor 124.

At block 204, the process 200 involves advancing the delivery system 100 through the inter-atrial septum 18 separating the right atrium 5 from the left atrium 2, such that the delivery system may pass into the left atrium 2, as shown in image 102 of FIG. 13. As referenced herein, such access to left atrium 2 may be made via other access routes, whereas image 102 shows a particular access route for purposes of explanation and simplicity. The operational block 204 may be performed with the sensor implant device 110 maintained in the at least partially compressed configuration shown in image 113.

At block 206, the process 200 involves advancing the delivery system 100 to, within, and/or in proximity to a pulmonary vein 26 that is fluidly coupled with the left atrium 2, as described in detail above. Although the image 103 shows the delivery system 100 advanced to the left superior pulmonary vein 26, it should be understood that such vein is represented in image 103 for descriptive purposes only, and any other pulmonary vein or other chamber or vessel may be engaged by the delivery system 100 in accordance with embodiments of the present disclosure.

At block 208, the process 200 involves deploying a distal anchor device 122 of the sensor implant device 110 in and/or to the target pulmonary vein 26 and/or tissue associated therewith. For example, with respect to stent-type, or other expandable tissue anchor devices, as shown in image 104, the operation associated with block 208 may involve expanding the tissue anchor device 122 within a conduit/lumen of the pulmonary vein 26. However, alternative anchoring mechanisms or techniques may be implemented, such as anchoring tissue-embedding anchor device(s) into the interior of the pulmonary vein conduit, or to left atrial tissue proximate to the pulmonary vein 26 and/or ostium thereof.

As described in detail herein, the distal anchor device 122 may be coupled or associated with an arm member/portion 131, which may be at least partially deployed from the delivery system 100 in connection with the operation associated with block 208 (and/or the operation associated with block 210, described below). In connection with the deployment of the distal anchor device 122 in the target pulmonary vein 26, the arm member/portion 131 may be at least partially bent or configured to accommodate the distal anchor device 122, such that the remainder of the sensor implant device 110 may be oriented at a generally-orthogonal/perpendicular orientation with respect to the axis of the distal anchor device 122, as shown in the accompanying image 117 of FIG. 14. For example, as shown in image 117, with the distal anchor device 122 deployed from the delivery system 100, at the stage of the process 200 associated with block 208 (and/or block 210), a portion 114 of the sensor implant device 110 may remain and/or be maintained within the delivery system 100 after deployment of the distal anchor device 122.

At block 210, the process 200 involves withdrawing the delivery system 100 an axial distance away from the pulmonary vein 26 in order to move the delivery system 100 and/or distal end thereof to, within, and/or into proximity with a second target pulmonary vein 23, which may thereby serve to deploy from the delivery system 100 one or more components or portions of the sensor implant device 110, such as one or more portions or components of the bridge/arm structure (e.g., portion 131) and/or sensor module 116, as shown in image 105, With the delivery catheter moved or approximated to the second target pulmonary vein 23, the portion 118 of the sensor implant device 110 that remains within the delivery system may include the proximal anchor device 124 and/or one or more portions 133 of the bridge/arm structure of the sensor implant device 110. That is, the sensor implant device 110 may be in a position/configuration in which the sensor module 116 is deployed from the delivery system 100 at a stage associated with the operation of block 210.

Figure 15:
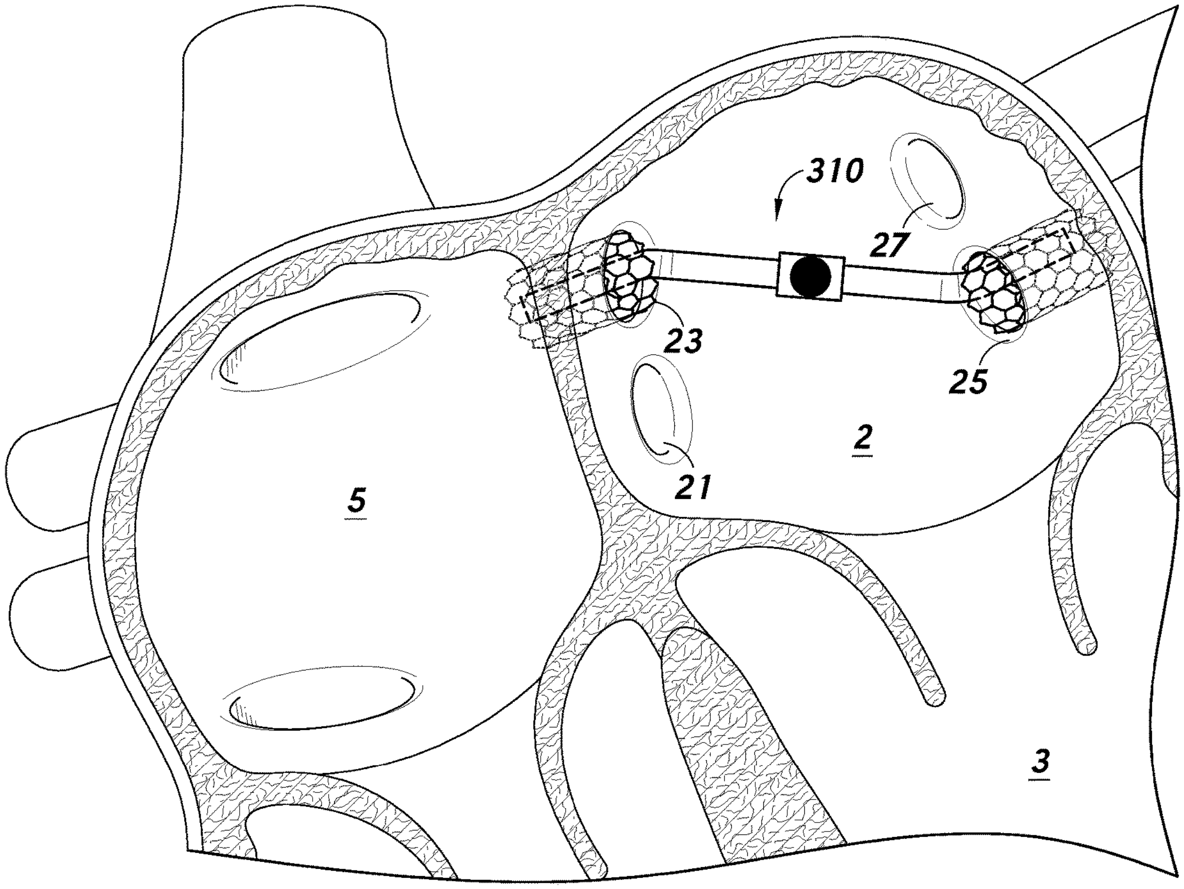
FIG. 15 shows a sensor implant device anchored in/to a left inferior pulmonary vein and a right superior pulmonary vein in accordance with one or more embodiments.

At block 212, the process 200 involves deploying the proximal anchor device 124 in the second target pulmonary vein 23. For example, the proximal anchor device 124 may be deployed and/or engaged in/with the second target pulmonary vein 23 in any suitable or desirable way, as described in detail herein. For example, the proximal anchor device 124 may comprise any suitable or desirable type of tissue anchor or securing device(s), whether expansion-type or tissue-embedding/suturing type anchor device(s), and whether anchored to the inside wall of the conduit of the pulmonary vein 23 and/or the left atrial tissue at or proximate to the ostium of the pulmonary vein 23. In deploying the proximal anchor device 124 and the pulmonary vein 23, the arm portion 133 coupling the proximal tissue anchor 124 to the remaining structure of the sensor implant device 110 may be unbent, or otherwise oriented or bent in order to allow for the anchor device 124 to be substantially coaxial with the pulmonary vein 23, while allowing the remainder of the bridge structure 130 of the sensor implant device 110 to bridge between the first target pulmonary vein 26 and the second target pulmonary vein 23. Although the second target pulmonary vein 23 is illustrated as corresponding to the right superior pulmonary vein, it should be understood that the second target pulmonary vein may be any suitable or desirable pulmonary vein, as described in detail below relative to FIGS. 15, 16, 17, and/or 18.

At block 214, the process 200 involves withdrawing the delivery catheter from the heart and/or body of the patient, thereby leaving or maintaining the sensor implant device 110 as implanted in and/or otherwise engaged with the target pulmonary veins 26, 23, as described above. Therefore, the sensor implant device 110 may be maintained in a shape or configuration similar to that shown in image 123 of FIG. 14 after implantation thereof.

FIGS. 6 and 13, described in detail above, illustrate for reference sensor implant devices implanted between a left superior pulmonary vein at a distal end of the sensor implant device and a right superior pulmonary vein at a proximal end of the sensor implant device. Furthermore, FIG. 8 illustrates a sensor implant device implanted between a left superior pulmonary vein and a left inferior pulmonary vein. However, it should be understood that such particular implementations are shown for illustrative purposes only, and implantation of sensor implant devices in accordance with embodiments of the present disclosure may be implanted between any two of the pulmonary veins (or other blood vessel), and/or may be implanted and/or secured to only a single pulmonary vein, or to three or more pulmonary veins.

FIG. 1.5 illustrates a left atrium 2 and associated anatomy, including pulmonary veins, wherein a sensor implant device 310 is implanted between a left inferior pulmonary vein 25 and a right superior pulmonary vein 23. Either the left inferior pulmonary vein 25 or the right superior pulmonary vein 23 may be considered the distal end or the proximal end of the sensor implant device 310 with respect to an implantation procedure implemented in connection with FIG. 1.5. The implantation orientation of the sensor implant device 310 as in FIG. 15 may be implemented in connection with any of the embodiments of the present disclosure, such as an alternative to any other illustrated and/or described orientations associated with the respective embodiments.

Figure 16:
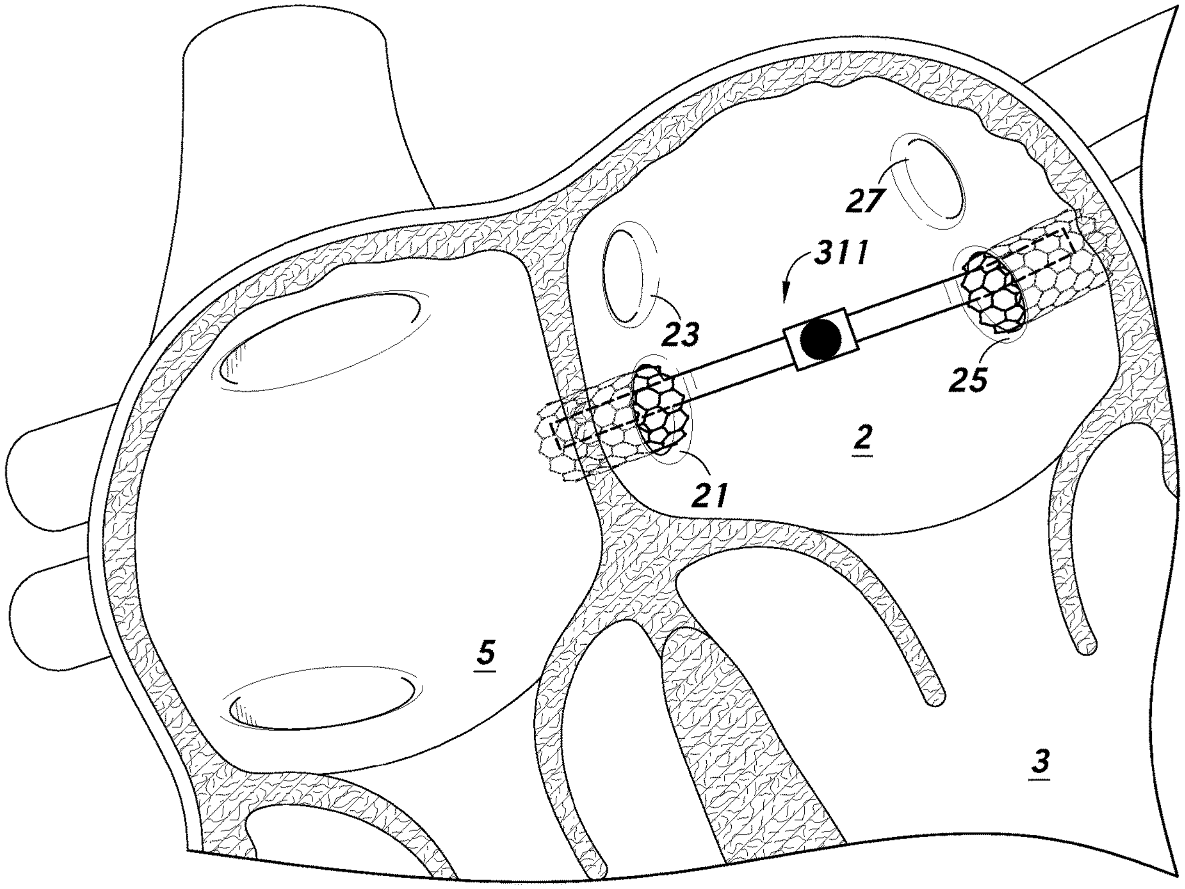
FIG. 16 shows a sensor implant device anchored in/to a left inferior pulmonary vein and a right inferior pulmonary vein in accordance with one or more embodiments.

FIG. 16 illustrates a left atrium 2 and associated anatomy, including pulmonary veins, wherein a sensor implant device 311 is implanted between a left inferior pulmonary vein 25 and a right inferior pulmonary vein 21. Either the left inferior pulmonary vein 25 or the right inferior pulmonary vein 21 may be considered the distal end for the proximal end of the sensor implant device 311 with respect to an implantation procedure implemented in connection with FIG. 16. The implantation orientation of the sensor implant device 311 as in FIG. 16 may be implemented in connection with any of the embodiments of the present disclosure, such as an alternative to any other illustrated and/or described orientations associated with the respective embodiments.

Figure 17:
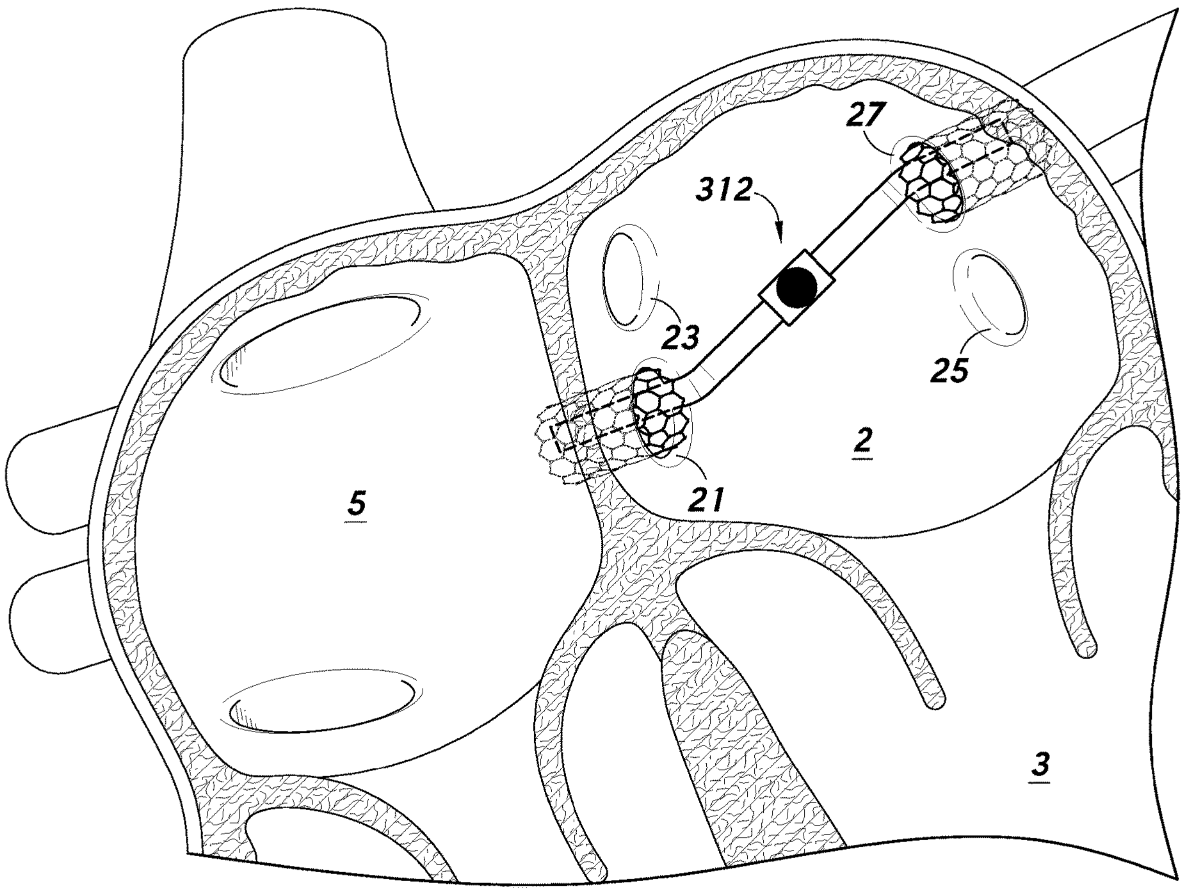
FIG. 17 shows a sensor implant device anchored in/to a left superior pulmonary vein and a right inferior pulmonary vein in accordance with one or more embodiments.

FIG. 17 illustrates a left atrium 2 and associated anatomy, including pulmonary veins, wherein a sensor implant device 312 is implanted between a left superior pulmonary vein 27 and a right inferior pulmonary vein 21. Either the left superior pulmonary vein 27 or the right inferior pulmonary vein 21 may be considered the distal end or the proximal end of the sensor implant device 312 with respect to an implantation procedure implemented in connection with FIG. 17. The implantation orientation of the sensor implant device 312 as in FIG. 17 may be implemented in connection with any of the embodiments of the present disclosure, such as an alternative to any other illustrated and/or described orientations associated with the respective embodiments.

Figure 18:
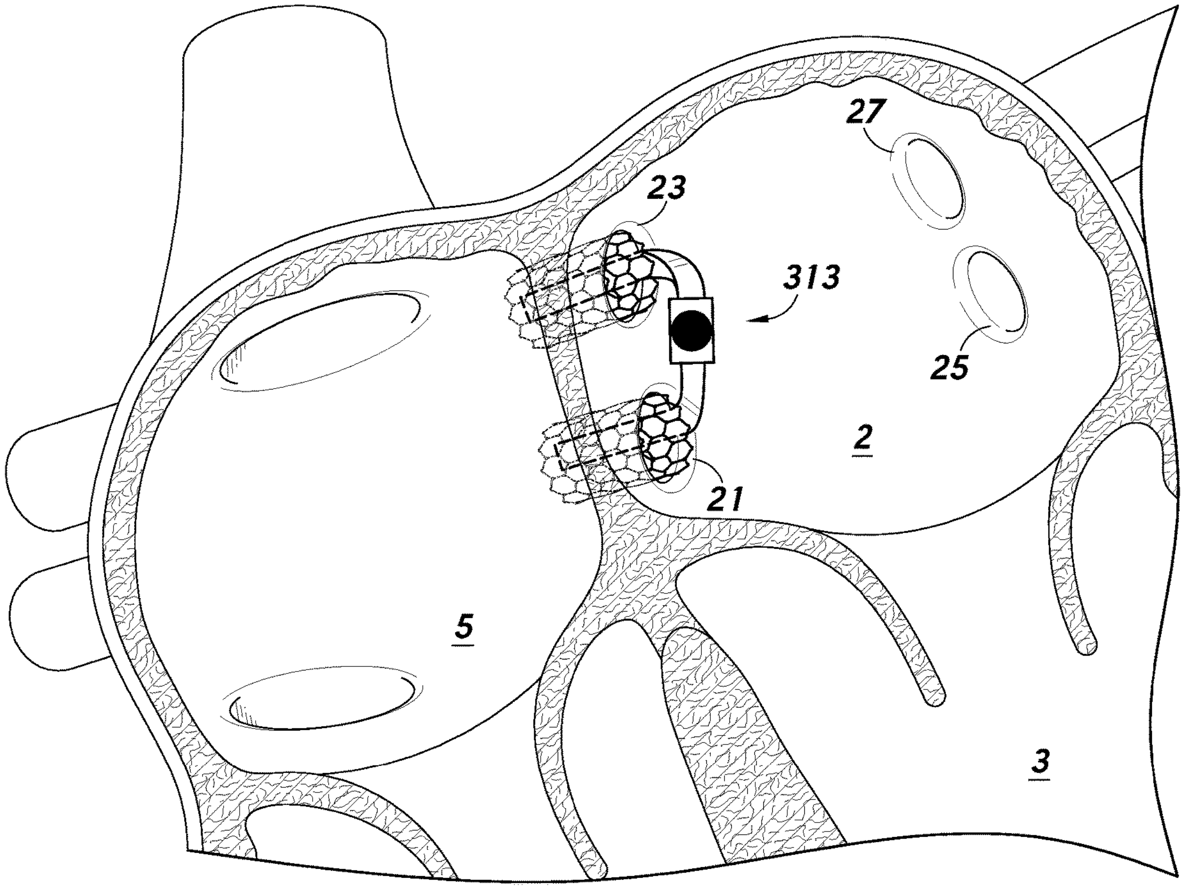
FIG. 18 shows a sensor implant device anchored in/to a right inferior pulmonary vein and a right superior pulmonary vein in accordance with one or more embodiments.

FIG. 18 illustrates a left atrium 2 and associated anatomy, including pulmonary veins, wherein a sensor implant device 313 is implanted between a right inferior pulmonary vein 21 and a right superior pulmonary vein 23. Either the right inferior pulmonary vein 21 or the right superior pulmonary vein 23 may be considered the distal end or the proximal end of the sensor implant device 313 with respect to an implantation procedure implemented in connection with FIG. 18. The implantation orientation of the sensor implant device 313 as in FIG. 18 may be implemented in connection with any of the embodiments of the present disclosure, such as an alternative to any other illustrated and/or described orientations associated with the respective embodiments.

Figure 19B:
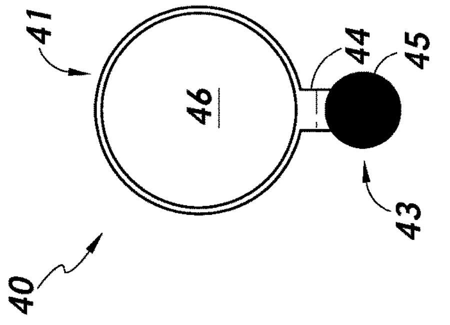
FIG. 19B shows an axial view of the sensor implant device of FIG. 19A in accordance with one or more embodiments.
Figure 19C:
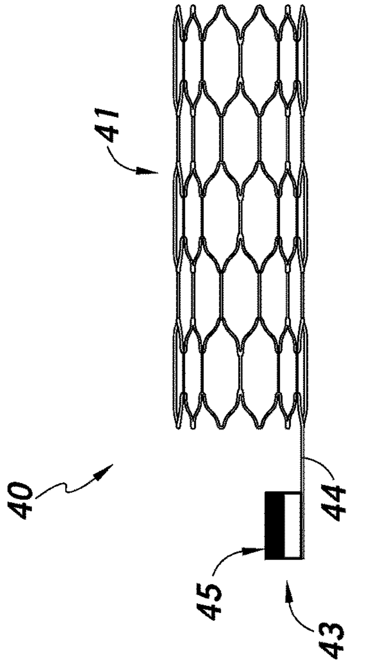
FIG. 19C shows a side view of the sensor implant device of FIG. 19A in a delivery configuration in accordance with one or more embodiments.
Figure 19A:
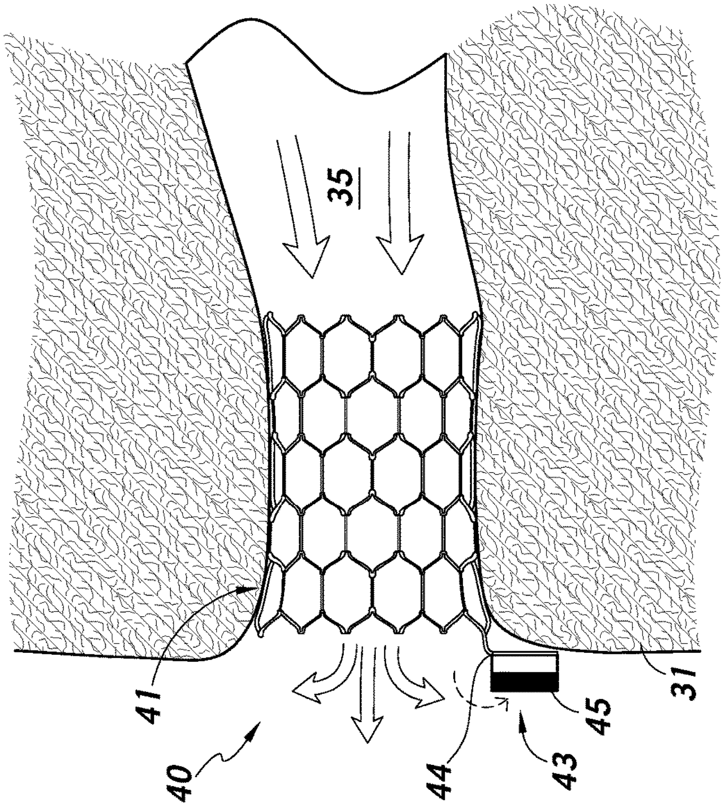
FIG. 19A shows a side deployed view of a sensor implant device anchored in a blood vessel in accordance with one or more embodiments.

Although various embodiments of the present disclosure are described in the context of sensor implant devices that are anchored using a plurality of stent-type anchors or other types of anchors, it should be understood that sensor devices in accordance with embodiments of the present disclosure may be supported and/or anchored by a single stent-type anchor or other type of anchor. FIG. 19A shows a side deployed view of a sensor implant device 40 anchored in a blood vessel 35 in accordance with one or more embodiments. FIG. 19B shows an axial view of the sensor implant device 40 of FIG. 19A in accordance with one or more embodiments. FIG. 19C shows a side view of the sensor implant device 40 of FIG. 19A in accordance with one or more embodiments.

The sensor implant device 40 shown in FIGS. 19A-19C includes a single stent anchor 41, wherein a sensor device 43 is physically coupled thereto in some manner. For example, in some embodiments, a support arm 44 may be attached to and/or integrated with the stent frame 41 and may mechanically couple the sensor device 43 to the anchor frame 41. In such a configuration, the sensor device 43 may extend axially from an end of the anchor frame 41, and possibly into a chamber or blood vessel into which the blood vessel 35 opens, wherein constituents of blood or other fluid present in such chamber/vessel are sensed by the sensor device 43, such as blood/fluid pressure or the like.

In some implementations, the anchor 41 may be anchored within a cardiac blood vessel such as within a pulmonary vein and/or ostium thereof, as described in detail herein. In such a configuration, the sensor device 43 may be exposed to blood/fluid within the left atrium, benefits of which are described above in detail.

With respect to any of the embodiments shown and described in connection with FIGS. 6-18, sensor support arm/strut features of such embodiments, as with any of the embodiments of FIGS. 19-31, may comprise separate bar-type features that are fixed to the respective stent anchors (or other types of anchors), or they may be integrated with the frames/forms of the respective anchors. It should be understood that any of the features of the sensor implant devices disclosed in connection with FIGS. 6-18 may be implemented in any of the sensor implant devices disclosed in connection with FIGS. 19-31, and any of the features of the sensor implant devices disclosed in connection with FIGS. 19-31 may be implemented in any of the sensor implant devices disclosed in connection with FIGS. 6-18.

As shown in FIG. 19A, the sensor device 43 and/or support arm 44 may be deflected radially outward with respect to the axis of the anchor frame 41, such that the sensor device 43 is substantially parallel to the tissue wall 31 (e.g., interior left atrium wall) outside of the anchoring vessel 35, or at an acute angle with respect to the tissue wall 31. Outward deflection of the sensor device 43 and/or support arm 44 may be achieved through manual bending of the support arm 44, or through autonomous movement/deflection of the sensor-support arm 44 caused by shape-memory characteristics/features of the arm 44. In some embodiments, the sensor-support arm 44 may be integrally formed with the anchor frame 41. For example, the support arm 44 may extend from one or more strut or extension features of the support frame 41. Such features may be laser-cut from a metal sheet/form to form an expandable stent frame and sensor-support arm/extension extending from the frame as an integral extension/feature thereof.

FIG. 19B shows an axial view of the sensor implant device 40, wherein the sensor device 43 and/or the sensor-support arm 44 are deflected radially outward. When implanted, the sensor transducer element/portion 45 of the sensor device 43 may be exposed outward (i.e., facing out of the page with respect to the illustrated orientation of FIG. 1913). With the sensor device 43 deflected away from the barrel/cylinder 46 of the anchor frame 41, readings of the sensor device 43 may be less directly tied to the flow through the barrel 46, and rather may be indicative of parameters of the blood in the chamber into which the vessel 35 opens.

FIG. 19C shows a side view of the sensor implant device 40 in a compressed state, in which the stent frame 41 is radially compressed to fit within, for example, a delivery catheter or other delivery system device/component. In the delivery configuration shown in FIG. 19C, the sensor-support arm 44 may be configured in a substantially straight configuration, such that the sensor device 43 is not deflected radially outward as in the deployed configuration of FIGS. 19A and 1913. Such straightened configuration may facilitate disposal in a cylindrical delivery catheter or other delivery component/device. As with any of the other embodiments disclosed herein relating to sensor devices that are supported by a sensor-support arm/strut associated with a vessel anchor, the sensor device 43 may be attached or coupled to the support arm/strut 44 in any suitable or desirable way. For example, the sensor device 43 may be secured to the support arm 44 using an adhesive, or other means. In some embodiments, a mechanical coupling is implemented between sensor device 43 and the arm 44. For example, the sensor device 43 may sit within a recess or other feature configured to engage the sensor housing around at least a portion of a circumference thereof. In some embodiments, the support arm 44 may include a hook, clasp, clip, or other locking/engagement feature configured to engage with an aperture or other opening feature of the sensor housing, or vice versa.

Figure 20B:
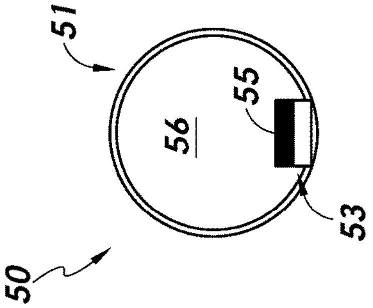
FIG. 20B shows an axial view of the sensor implant device of FIG. 20A in accordance with one or more embodiments.
Figure 20C:
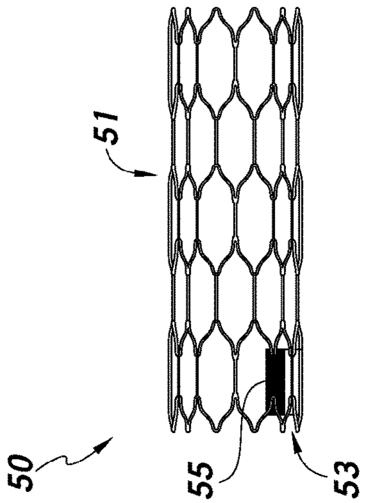
FIG. 20C shows a side view of the sensor implant device of FIG. 20A in a delivery configuration in accordance with one or more embodiments.
Figure 20A:
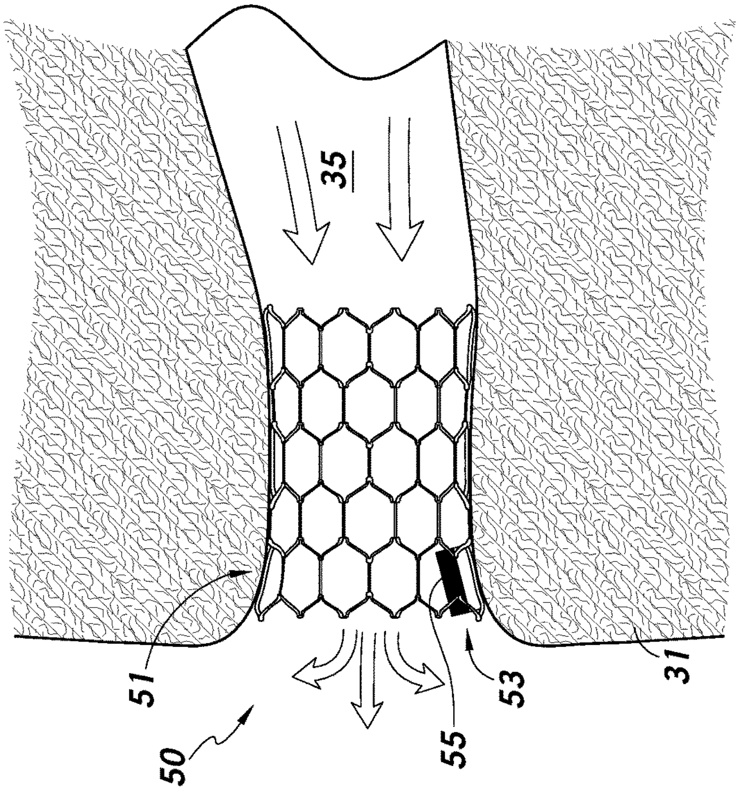
FIG. 20A shows a side deployed view of a sensor implant device anchored in a blood vessel in accordance with one or more embodiments.

FIG. 20A shows a side deployed view of a sensor implant device 50 anchored in a blood vessel 35, such as a pulmonary vein and/or pulmonary vein ostium, in accordance with one or more embodiments. FIG. 20B shows an axial view of the sensor implant device 50 of FIG. 20A in accordance with one or more embodiments. FIG. 20C shows a side view of the sensor implant device 50 of FIG. 20A in a delivery configuration in accordance with one or more embodiments. Unlike FIGS. 19A-19C, which illustrates a sensor implant device 40 including a sensor 43 supported by an arm/strut feature 44, which extends axially from an end of the stent anchor frame 41, the embodiments of the sensor implant device 50 shown in FIGS. 20A-20C include a sensor device 53 that is secured to the anchor frame 51 through direct attachment to the inner diameter thereof. That is, the sensor device 53 may be embedded and/or secured in some manner in/to the stent frame 51 without the need/use of an axially extending support arm/strut.

With the sensor device 53 secured to the inner diameter/surface of the anchor frame 51, the sensor transducer feature/element 55 may be generally exposed within the inner barrel 56 of the device 50. Therefore, with the anchor frame 51 anchored within a blood vessel 35, such as a pulmonary vein, the sensor transducer 55 may be configured to sense characteristics of blood flow through the blood vessel 35 and stent frame 51. In some cases, the fluid pressure within the pulmonary vein or other blood vessel 35 may be different than that in the chamber (e.g., left atrium) outside of the blood vessel 35. Therefore, this position of the sensor device 53 within the inner diameter of the stent frame 51 may allow for sensing of fluid characteristics that may be different from corresponding characteristics of fluid present outside of the blood vessel 35, such as flow, pressure, and/or other sensed characteristics.

As shown, the sensor device 53 may be attached to the frame 51 at or near a distal end of the frame 51 (i.e., on a left side of the frame 51 in the illustrated orientation of FIG. 20A). In some embodiments, the sensor device 53 may be secured to the inner diameter of the frame 51 through adhesive, welding, and/or other permanent or temporary fixation means. For example, in some embodiments, the housing of the sensor 53 may be configured to be snapped, hooked, clipped, clasped, and/or otherwise engaged with the frame 51, such as within one or more cells of the frame lattice, to provide a mechanical attachment/locking connection between the sensor 53 (and/or sensor housing) and the frame.

As shown in FIG. 20B, which shows an axial view of the sensor implant device 50, the sensor device 53 may be configured to fit within the barrel 56 of the device 50, wherein the sensor transducer element/feature 55 of the sensor device 53 generally faces radially inward. In some embodiments, the sensor transducer 55 may be generally axially oriented, such that the face thereof faces with or opposing the flow of fluid through the barrel 56.

FIG. 20C shows the sensor implant device 50 in a compressed delivery configuration. For example, the anchor frame 51 may be radially crimped/compressed to allow for a smaller diametrical profile for disposing within a delivery catheter or other delivery device. The sensor device 53 may advantageously be small enough such that radial crimping of the anchor frame 51 is not impeded by the presence of the sensor device 53 within the barrel 56 of the anchor frame 51.

Figure 21B:
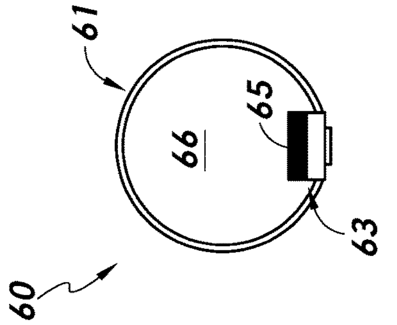
FIG. 21B shows an axial view of the sensor implant device of FIG. 21A in accordance with one or more embodiments.
Figure 21C:
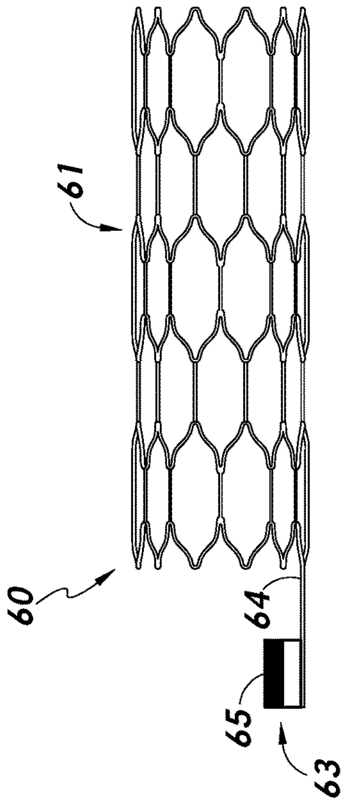
FIG. 21C shows a side view of the sensor implant device of FIG. 21A in a delivery configuration in accordance with one or more embodiments.
Figure 21A:
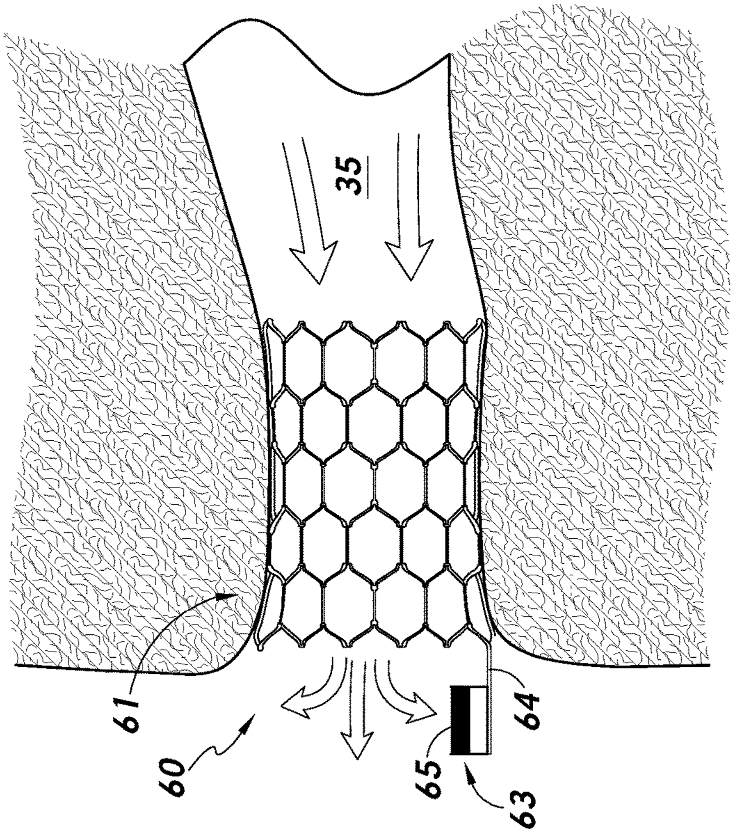
FIG. 21A shows a side deployed view of a sensor implant device anchored in a blood vessel in accordance with one or more embodiments.

FIG. 21A shows a side deployed view of a sensor implant device 60 anchored in a blood vessel 35 in accordance with one or more embodiments. FIG. 21B shows an axial view of the sensor implant device 60 of FIG. 21A in accordance with one or more embodiments. FIG. 21C shows a side view of the sensor implant device 60 of FIG. 21A in a delivery configuration in accordance with one or more embodiments.

The sensor implant device 60 illustrated in FIGS. 21A-21C is similar in various respects to the sensor implant device 40 shown in FIGS. 19A-19C and described above. However, unlike the sensor implant device 40 shown in FIG. 19A, the sensor implant device 60, shown in FIG. 21A in a deployed configuration, may not be radially deflected when deployed. For example, as shown, the sensor-support arm/strut 64 may extend axially from an end of the stent frame 61 (i.e., left-most end of the frame 61 in the illustrated orientation of FIG. 21A) in a generally straight configuration. Iii the straight configuration shown in FIG. 21A, the sensor transducer 65 may generally face radially inward with respect to the axis of the anchor frame 61. However, it should be understood that in some embodiments, the sensor transducer 65 may face radially outward and/or axially distally or proximally with respect to the orientation of the anchor frame 61.

With respect to the axial view of FIG. 21B, the radially-inward-facing orientation of the sensor device 63 and/or sensor transducer 65 is demonstrated, wherein the sensor transducer 65 lies within the radius of the barrel 56 of the frame 61, albeit in a position that is axially extended beyond the end of the frame 61. In the delivery configuration, as shown in FIG. 21C, the sensor device 63 may be supported by a generally straight support strut/arm 64 during delivery thereof.

Figure 22B:
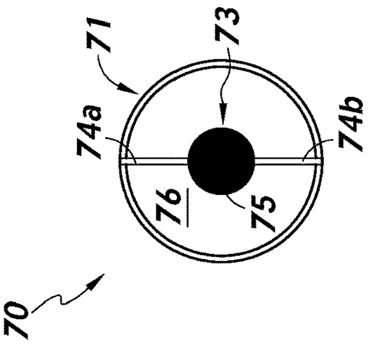
FIG. 22B shows an axial view of the sensor implant device of FIG. 22A in accordance with one or more embodiments.
Figure 22C:
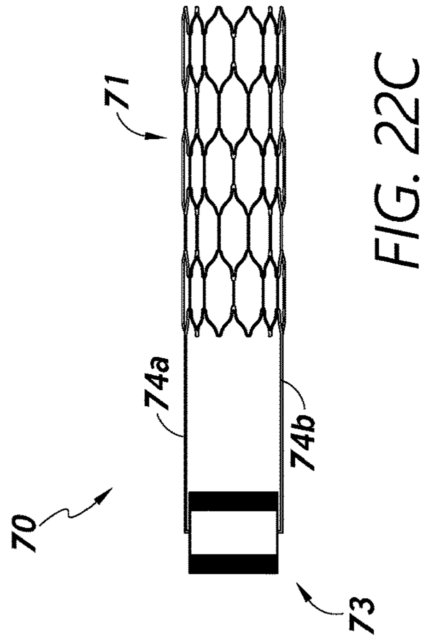
FIG. 22C shows a side view of the sensor implant device of FIG. 22A in a delivery configuration in accordance with one or more embodiments.
Figure 22A:
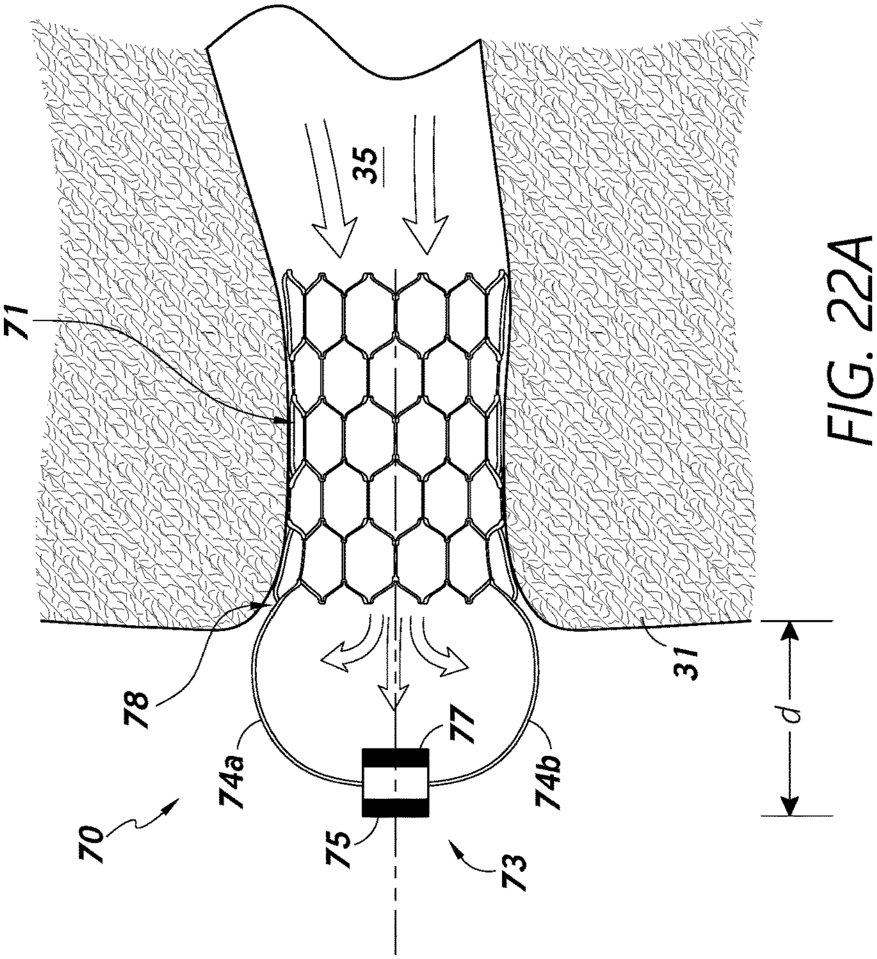
FIG. 22A shows a side deployed view of a sensor implant device anchored in a blood vessel in accordance with one or more embodiments.

FIG. 22A shows a side deployed view of a sensor implant device 70 anchored in a blood vessel 35 in accordance with one or more embodiments. FIG. 22B shows an axial view of the sensor implant device 70 of FIG. 22A in accordance with one or more embodiments. FIG. 22C shows a side view of the sensor implant device 70 of FIG. 2.2A in a delivery configuration in accordance with one or more embodiments.

In the embodiments of FIGS. 22A-22C, the sensor device 73 is supported by a plurality of support arms 74*a*, 74*b*. For example, the sensor device 73 may be held at or near an axial center of the barrel 76 of the anchor frame 71, which may be deployed/implanted within a blood vessel 35, such as a pulmonary vein. In some embodiments, the arms 74*a*, 74*b* may hold the sensor device 73 in a position axially beyond the end 78 of the anchor frame 71 (i.e., the leftmost end of the frame 71 with respect to the illustrated orientation of FIG. 22A), such that the sensor device 73 is disposed some distance the in front of i.e., to the left of with respect to FIG. 22A) the anchor frame 71 and/or ostium of the blood vessel 35. In some embodiments, the support arms/struts 74*a*, 74*b* hold the sensor device 73 within the axial bounds of the support frame 71. That is, unlike the illustrated implementation shown in FIG. 22A, in some embodiments, the sensor device 73 may be held axially within the anchor frame 71.

FIG. 22B shows the sensor device 73 held by the support arms 74*a*, 74*b* within the radius of the barrel 76 of the anchor frame 71, albeit axially beyond the end of the frame 71. The sensor device 73 may include one or more sensor transducer features/elements 75, 77. For example, the sensor transducer 77 is shown as facing against of the flow of fluid through the anchor frame 71, and therefore may be configured and/or disposed in a position to sense parameters associated with such fluid flow incident on the fate of the transducer 77. In some embodiments, the sensor device 73 includes a sensor transducer 75 facing axially outward with respect to the orientation of the anchor frame 71. With the outward-facing transducer 75, the sensor 73 may be configured to sense parameters of the fluid within the chamber (e.g., left atrium) outside of the blood vessel 35 that is less affected by the flow through the anchor frame 71 than with respect to sensor transducers facing axially inward, as with the illustrated transducer 77. Although two sensor transducers are shown in FIGS. 22A and 22C, it should be understood that any number of such transducers, including a single such transducer, may be implemented in connection with the embodiments of FIGS. 22A-22C.

The arms 74*a*, 74*b* may attached to the housing/structure of the sensor 73 in any suitable or desirable manner. In some embodiments, the arms are configured to hook or otherwise engage into/with eyelet/aperture features of the sensor housing to create a mechanical coupling therewith. In some embodiments, the arms 74*a*, 74*b* form or are associated/ integrated with a circumferential sensor-retention band or cup feature in which the sensor device 73 may be disposed/ secured. The sensor device 73 may be secured to the arms 74*a*, 74*b* and/or associated sensor-retention features thereof through tension fit or other mechanical attachment mechanism. In the delivery configuration shown in FIG. 22C, the support arms 74*a*, 74*b* may assume a bent configuration, wherein such bends are at sharper angles than the bends of the arms 74*a*, 74*b* in the deployed configuration shown in FIG. 22A. In the delivery configuration, the sensor device 73 may be already coupled to the support arms 74*a*, 74*b*, such that in deployment, no attachment of the sensor device 73 to the support arms 74*a*, 74*b* is necessary.

Figure 23:
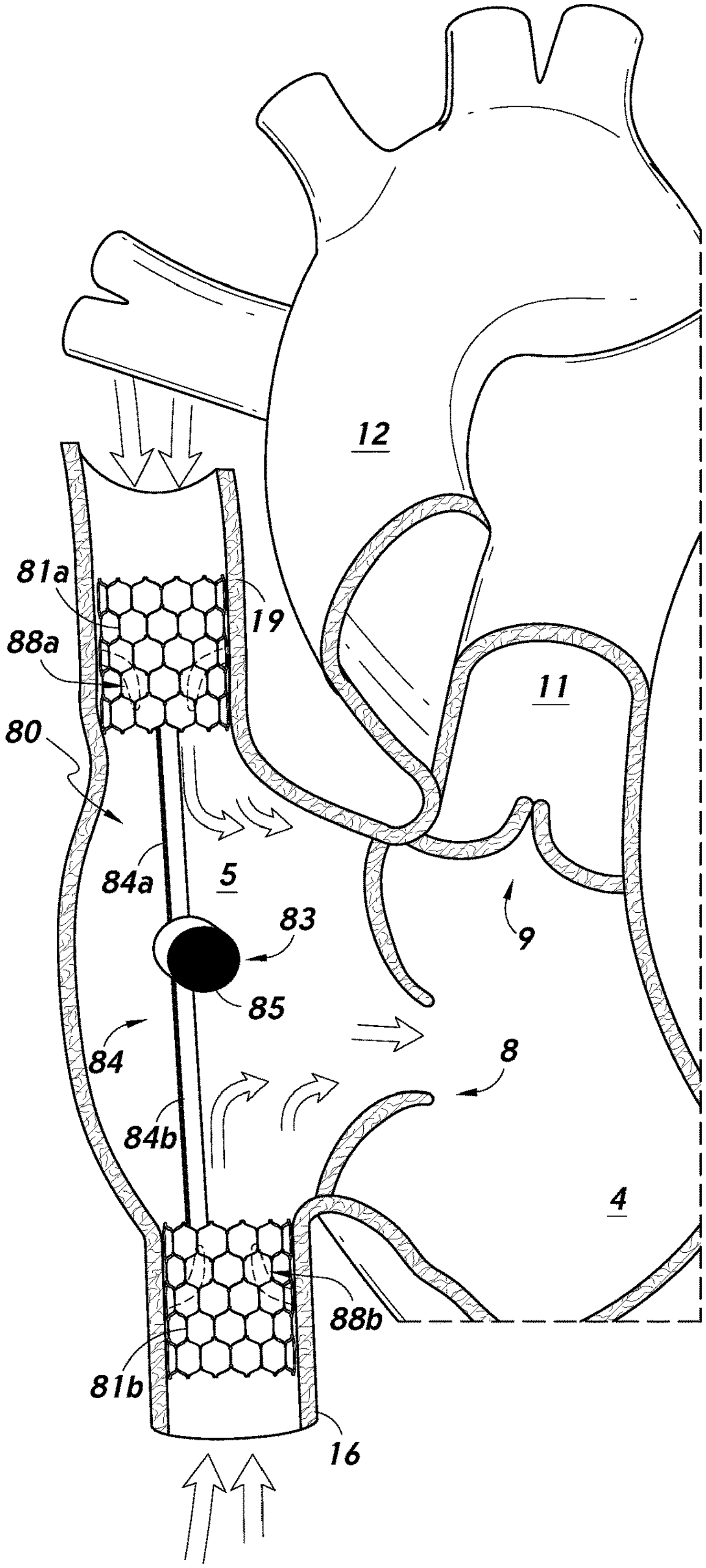
FIG. 23 shows a sensor implant device implanted in the superior and inferior vena cavae in accordance with one or more embodiments.

FIG. 23 shows a sensor implant device 80 implanted in the superior and inferior vena cavae in accordance with one or more embodiments. The sensor implant device 80 includes a sensor 83 coupled to one or more stent-like anchors 81*a*, Sib configured to be anchored within the superior 19 and inferior 16 vena cava, respectively. For example, the sensor 83 may be coupled to the stent anchors via one or more arms/connectors 84. For example, the first arm portion 84*a* may physically extend between the sensor 83 and the stent anchor 81*a*, whereas the arm portion 84*b* may extend between the sensor 83 and the stent anchor 81*b*. The arm(s) 84 may comprise a single bar extending between the stent anchor 81*a* and the stent anchor 81*b*, wherein the sensor 83 is secured in some manner to the bar 84. In some embodiments, the portions 84*a*, 84*b* represent physically separate arm segments extending from the sensor 83. The sensor 83 may be coupled to the arm(s) 84 in any suitable or desirable manner, such as through the use of one or more adhesives, clips, fittings, and/or other coupling features.

With the sensor 83 coupled to one or more stent anchors 81 as in FIG. 23, the sensor 83 may generally be disposed and exposed within the right atrium 5 of the heart. The use of a sensor, such as a pressure sensor, within the right atrium can provide readings indicating central venous pressure (CBP) or other parameter associated with central venous blood flow.

In some embodiments, one or more of the anchors 31 may include certain valve features 88. For example, such valve features may be one-way valves, which may allow fluid flow into the right atrium from the inferior and/or superior vena cavae, while impeding our preventing blood flow from the right atrium 5 into the superior 19 and/or inferior vena cavae. In embodiments in which one or more anchors 81 include one-way valves allowing outflow into the right atrium, such valve(s) can prevent or reduce backflow into the veins, thereby reducing the risk and/or occurrence of edema, swelling, and/or other medical conditions. Although embodiments of the present disclosure are described herein including one or more stent anchors with valve features anchored in one or more of the superior and inferior vena cavae, wherein such anchor(s) are coupled to a sensor that is exposed at least partially within the right atrium, in some embodiments, valved stent anchors may be implanted/disposed within the vena cava without an associated/coupled sensor device. That is, the anchors may be used for the purpose of preventing backflow of blood into the veins, with or without associated sensor functionality/feature(s).

In embodiments that do not include a sensor device, any physical coupling 84 between the anchors 81 that may be present may be used as a docking structure for any type of implant device. Furthermore, even in embodiments that include a sensor device, such as is shown in FIG. 23, the coupling arm 84 may be used for docking one or more additional implant devices or components, such as spacer devices, replacement valves, or the like. For example, in some embodiments, a replacement valve device, such as a replacement tricuspid valve, may be implanted within the annulus of the tricuspid valve 8 and further secured or docked to the arm structure 84 and/or one or more of the blood vessel anchors 81. In some embodiments, a tricuspid valve spacer device may be anchored to the coupling arm 84 and/or one or more of the stent anchors 81. The optional valve features 88 may comprise 2, 3, or other number of leaflets, which may be formed of biological and/or synthetic material(s).

The sensor implant device 80 may be implanted in any suitable or desirable manner. For example, implanting the sensor implant device 80 may involve advancing a delivery system, which may include one or more delivery catheters, into to a first vena cava of the patient, either the superior vena cava 19 or the inferior vena cava 16, via a transcatheter access path, as shown and described in connection with FIG. 32. The method may further involve advancing the delivery system through at least a portion of a right atrium 5 of the patient and into a second vena cava of the patient (i.e., the other of the superior vena cava 19 and the inferior vena cava 16), deploying a distal anchor (i.e., a first one of the anchors 81*a*, 81*b*, depending on which of the vena cavae the anchor is being deployed in) of a sensor implant device from the delivery system, anchoring the distal anchor of the sensor implant device within the second vena cava. The delivery system may then be withdrawn through the at least a portion of the right atrium 5, thereby exposing at least a portion of the sensor device 83 of the sensor implant device, as well as a first support arm portion (i.e., either 84*a* or 84*b*, or both) coupling the sensor device to the distal anchor, in the right atrium 5. The process may further involve deploying a proximal anchor of the sensor implant device (i.e., a second one of the anchors 81*a*, 81*b*, depending on which of the vena cavae the anchor is being deployed in) from the delivery system within the first vena cava, and anchoring the proximal anchor of the sensor implant device to within the first vena cava. The delivery system may then be withdrawn from the patient.

Figure 24A:
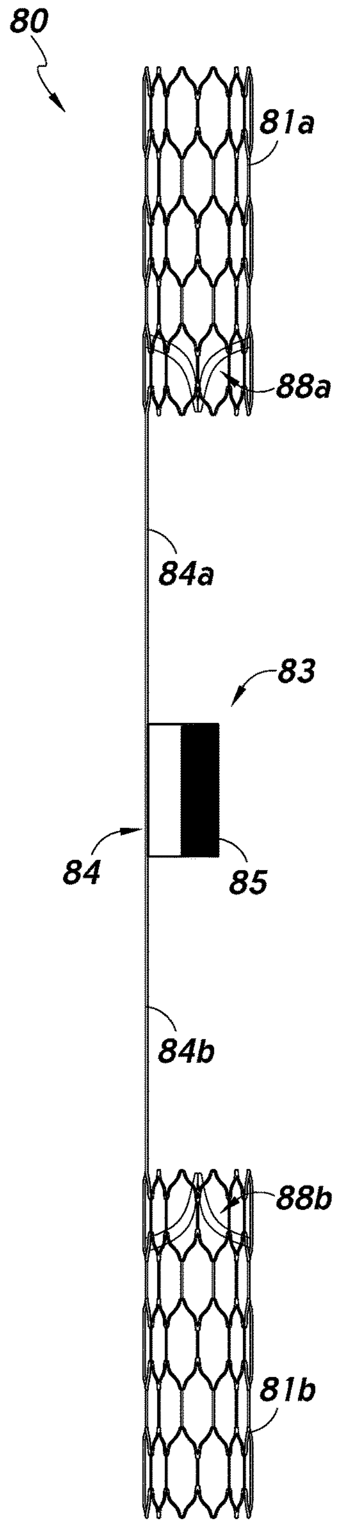
FIGS. 24A-C show crimped side, expanded front, and axial views, respectively, of a sensor implant device in accordance with one or more embodiments.
Figure 24B:
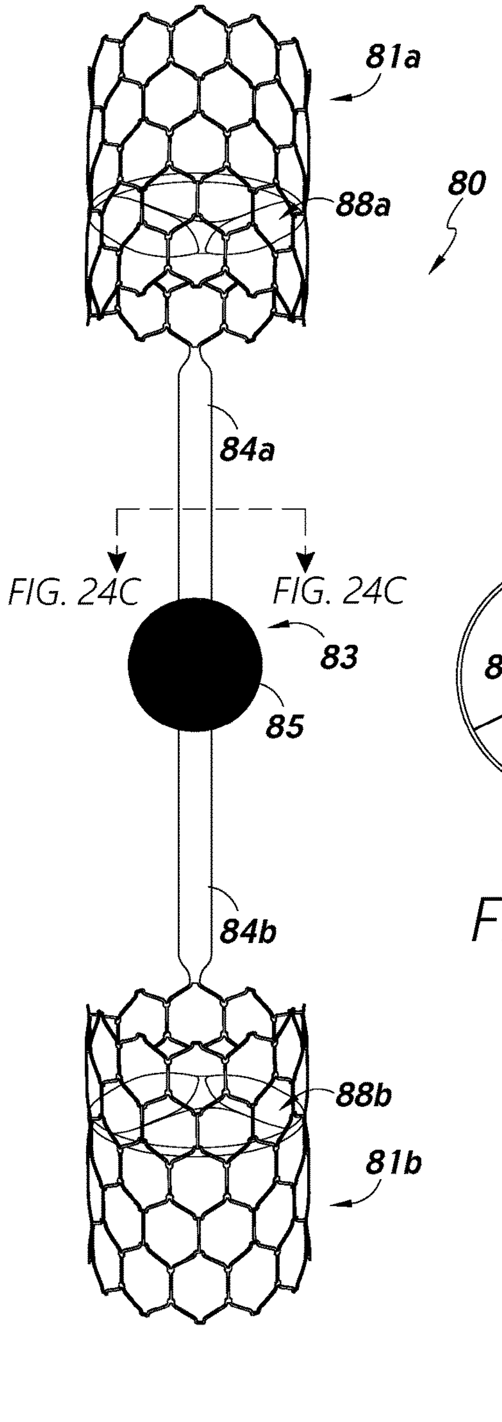
Figure 24C:
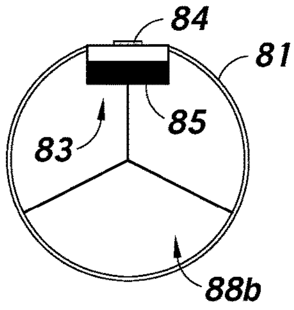

FIGS. 24A-C show crimped side, expanded front, and axial views, respectively, of a sensor implant device in accordance with one or more embodiments. In particular, FIG. 24A shows the cardiac implant device 80 of FIG. 23 in an at least partially crimped/compressed delivery configuration. In the delivery configuration shown in FIG. 24A, the one or more stent anchors 81 may be radially compressed such that a cross-sectional profile thereof is sufficiently small to fit within the delivery catheter or other delivery device or system component. It should be understood that the coupling arm segments 84 may have any suitable or desirable length.

FIG. 24B shows a front view of the device 80, wherein the sensor transducer 85 is shown. In the configuration of FIG. 24B, the sensor implant device 80 is in a deployment configuration, wherein the stent anchors 21 are at least partially expanded for contact with respective blood vessel walls of the superior and inferior vena cavae. The images of FIGS. 24A and 24B show the optional valve features 88*a* and 88*b* associated with the anchors 81*a* and 81*b*, respectively. The illustrated embodiment includes one or more 3-leaflet valves. However, it should be understood that valve features associated with anchors disclosed herein have any number of leaflets and/or other valve component or features.

FIG. 24C shows an axial view of the device 80 showing the sensor 83 and the valve feature 88*b*. As shown, the sensor transducer 85 may be disposed within and/or facing radially inward with respect to the radius/diameter of the anchor 81. Therefore, blood flow through the anchor valve 88 may be directed generally in the direction of the sensor device 53, some of which may pass over the sensor transducer 85.

Figure 25:
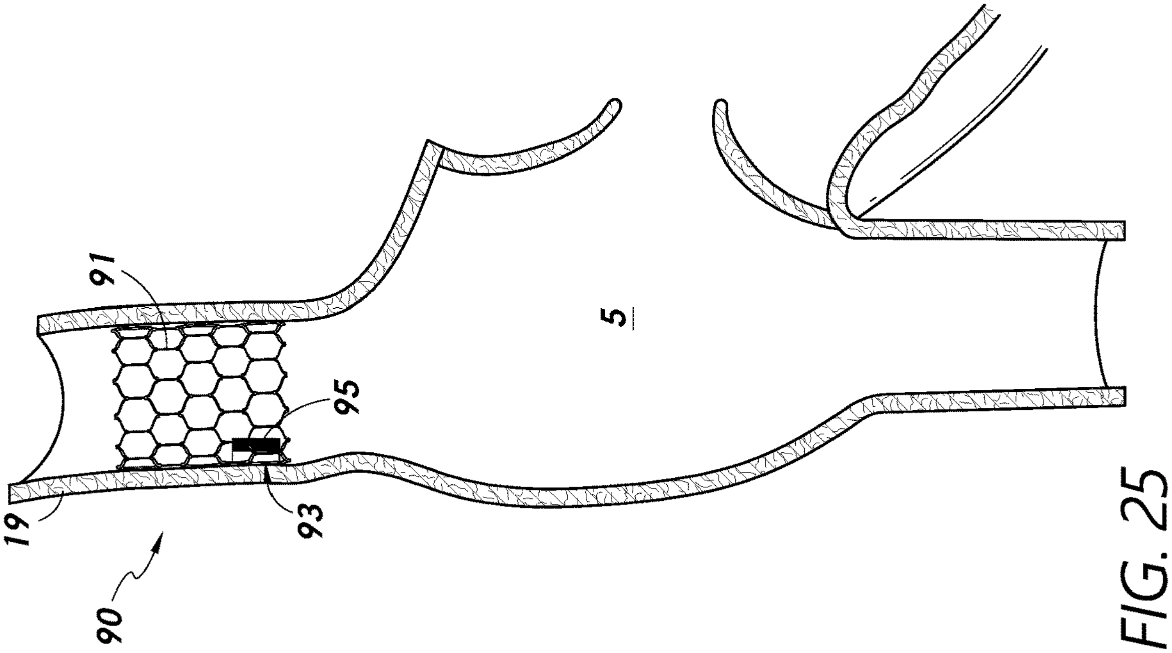
FIG. 25 shows a sensor implant device anchored in a superior vena cava in accordance with one or more embodiments.

FIG. 25 shows a sensor implant device 90 anchored in a superior vena cava 19 in accordance with one or more embodiments. The sensor implant device 90 includes a sensor device 93 mechanically coupled to and/or otherwise associated with the inner diameter of the stent anchor 91. That is, the sensor 93 may not be coupled to the anchor 91 by an extended arm feature, as in FIG. 23, but rather may be disposed at least partially within the inner diameter of the stem anchor 91. The stent anchor 91 is disposed in the superior vena cava 19 and therefore the sensor 93 may be configured to determine certain parameters associated with blood flow into the right atrium 5 from the superior vena cava 19.

Figure 26:
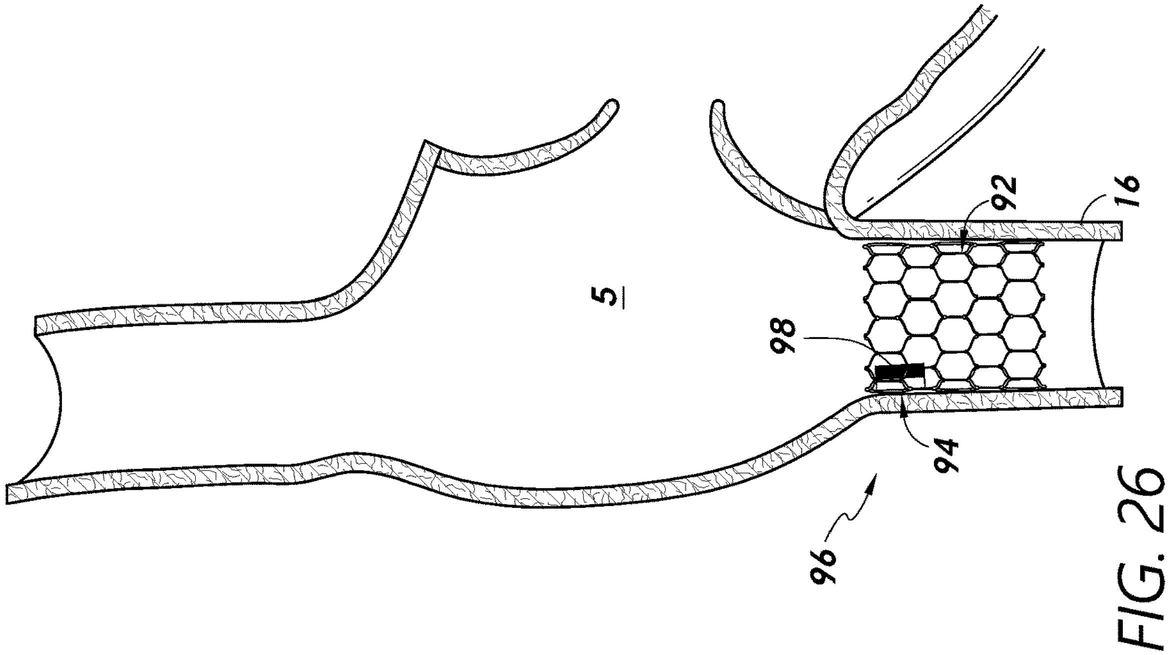
FIG. 26 shows a sensor implant device anchored in an inferior vena cava in accordance with one or more embodiments.

FIG. 26 shows a sensor implant device 96 anchored in an inferior vena cava 16 in accordance with one or more embodiments. The sensor implant device 96 includes a sensor device 94 mechanically coupled to and/or otherwise associated with the inner diameter of the stent anchor 92. That is, the sensor 94 may not be coupled to the anchor 92 by an extended arm feature, as in FIG. 23, but rather may be disposed at least partially within the inner diameter of the stent anchor 92. The stent anchor 92 is disposed in the inferior vena cava 16 and therefore the sensor 94 may be configured to determine certain parameters associated with blood flow into the right atrium 5 from the inferior vena cava 19.

Figure 27:
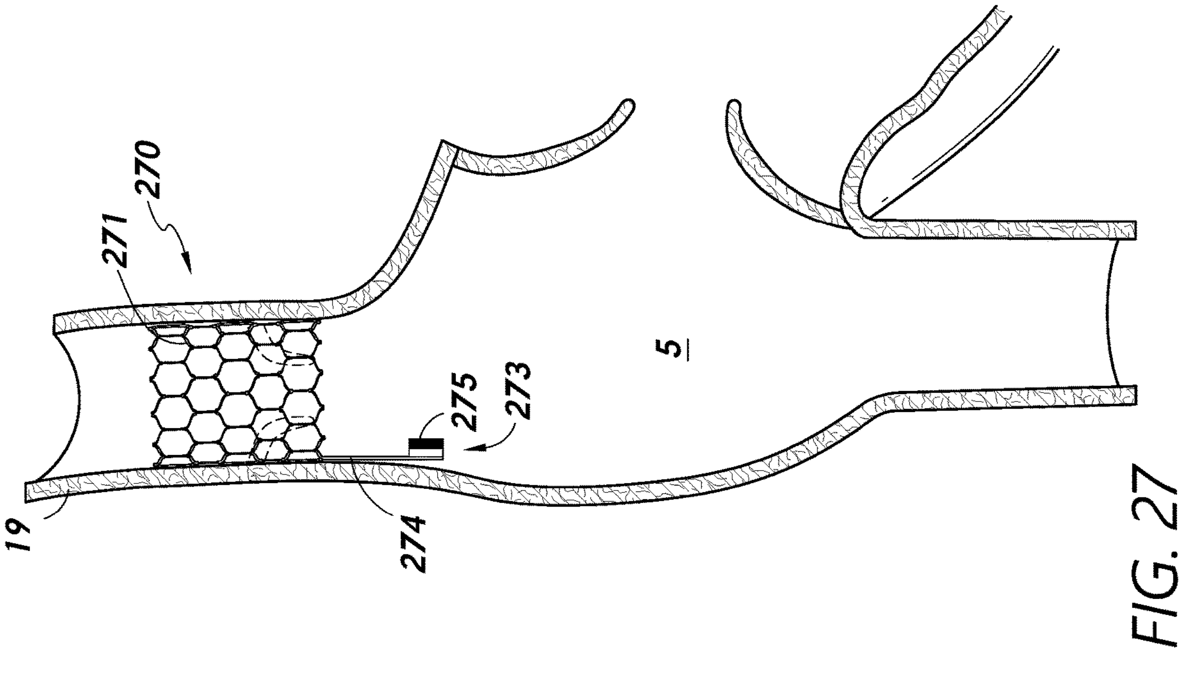
FIG. 27 shows a sensor implant device anchored in a superior vena cava in accordance with one or more embodiments.

FIG. 27 shows a sensor implant device 270 anchored in a superior vena cava 19 in accordance with one or more embodiments. The sensor implant device 270 includes a sensor device 275 mechanically coupled to a stent anchor 271 via a coupling arm 274, which may be similar in certain respects to any of the other coupling arm features disclosed in connection with various embodiments of the present disclosure. The coupling arm 274 may have any suitable or desirable length. For example, the length of the coupling arm 274 may be selected to project the sensor device 273 a desired distance into the right atrium 5, Although the sensor transducer 275 is illustrated as being oriented and/or facing inward with respect to an axis of the anchor 271, as with any other embodiment disclosed herein, it should be understood that the sensor device 273 may have sensor transducer(s) configured and/or oriented in any suitable or desirable way. Furthermore, although the coupling arm 274 is shown as a generally straight, it should be understood that the arm 274 may have any length, shape, and or configuration. For example, in some embodiments, the arm 274 may be deflected towards a center of the right atrium 5 to thereby provide a more central position for the sensor device 273 with respect to the right atrium 5.

Figure 28:
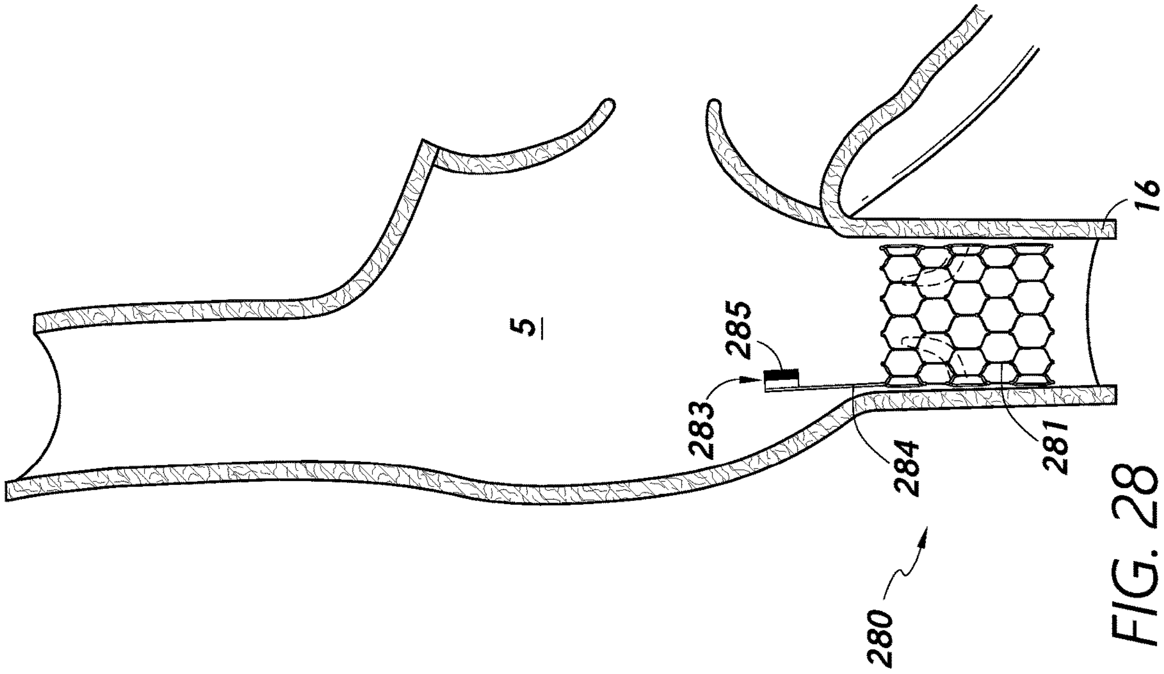
FIG. 28 shows a sensor implant device anchored in an inferior vena cava in accordance with one or more embodiments.

FIG. 28 shows a sensor implant device 280 anchored in an inferior vena cava 16 in accordance with one or more embodiments. The sensor implant device 280 includes a sensor 283 mechanically coupled to a stent anchor 281 via a coupling arm 284, which may be similar in certain respects to any of the other coupling arm features disclosed in connection with various embodiments of the present disclosure. The coupling arm 284 may have any suitable or desirable length. For example, the length of the coupling arm 284 may be selected to project the sensor device 283 a desired distance into the right atrium 5. Although the sensor transducer 285 is illustrated as being oriented and/or facing inward with respect to an axis of the anchor 281, as with any other embodiment disclosed herein, it should be understood that the sensor device 283 may have sensor transducer(s) configured and/or oriented in any suitable or desirable way. Furthermore, although the coupling arm 284 is shown as a generally straight, it should be understood that the arm may have any length, shape, and or configuration. For example, in some embodiments, the arm 284 may be deflected towards a center of the right atrium 5 to thereby provide a more central position for the sensor device 283 with respect to the right atrium 5.

Figure 29:
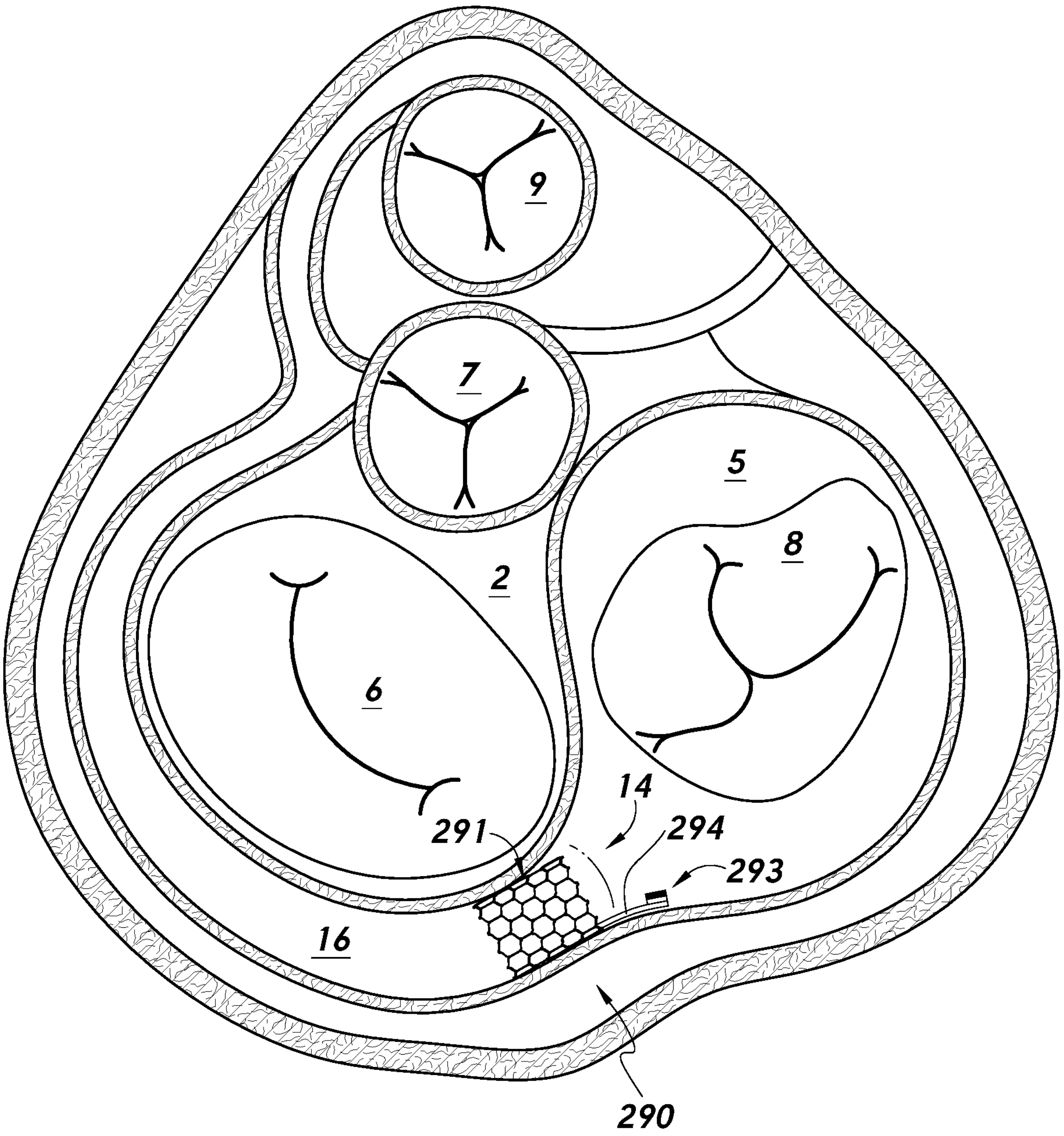
FIG. 29 shows a sensor implant device anchored in a coronary sinus in accordance with one or more embodiments.

FIG. 29 shows a sensor implant device 290 anchored at least partially within a coronary sinus 16 and/or ostium 14 thereof. The sensor implant device 290 includes a sensor device 293, which may be similar in certain respects to various other embodiments disclosed herein. The sensor device 293 is coupled to the anchor 291 via a coupling arm 294, as with other embodiments disclosed herein. In some embodiments, the implant device 290 does not include a sensor and/or sensor coupling arm, but rather includes a valve feature or other feature associated with the stent anchor 291.

Anchoring of a sensor implant device at least partially within the coronary sinus can allow for placement of an associated sensor within and/or near the right atrium, which may allow for measurement of central venous blood pressure and/or other parameter(s) associated with central venous flow and/or the right atrium. For example, sensors associated with implant devices anchored to/in the coronary sinus may be used to sense/determine various hemodynamic parameters, such as central venous pressure, blood viscosity, pulmonary artery pressure, and/or other parameter(s). As with any other stent-type anchor embodiment disclosed herein, such anchors may be self-expandable or balloon-expandable. For example, a delivery catheter may be used to deliver and/or implant the anchor device 291. The location of the sensor anchor 291 at or near the coronary sinus ostium 14 can be used for attaching biodegradable or drug-eluding devices and/or may be used as an anchor for various medical device implants, including replacement valve devices, valve spacer devices, and/or the like.

Although stent anchors are generally described and illustrated in connection with the present disclosure, it should be understood that such anchors may have any suitable form, shape, and/or configuration. For example, in some embodiments, other types of anchor features are implemented, including spiral wire anchors, barbs, and/or other types of tissue anchors.

Figure 30:
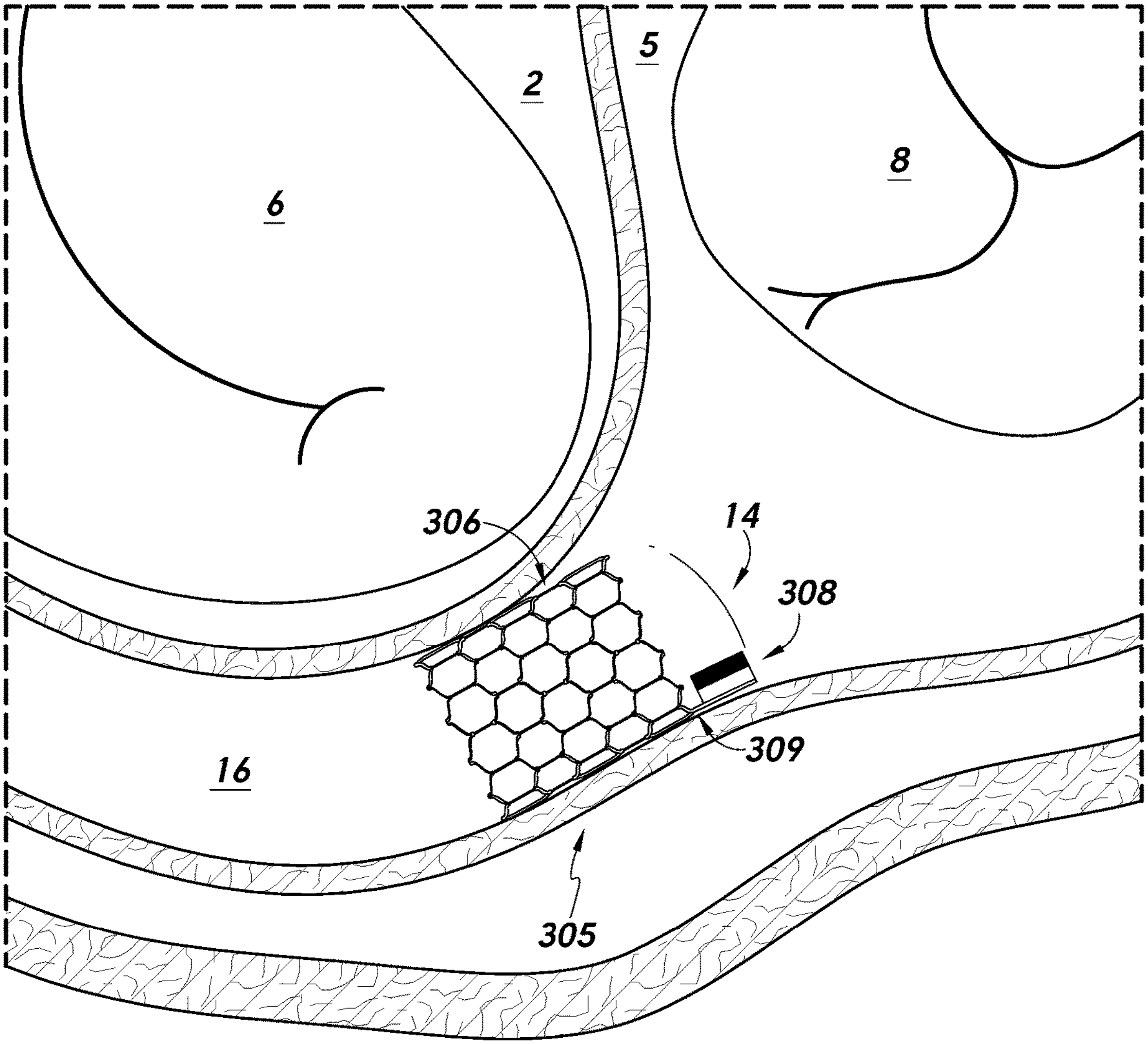
FIG. 30 shows a sensor implant device anchored in a coronary sinus in accordance with one or more embodiments.

The sensor coupling arm 294 may have any suitable or desirable length, wherein such length may be designed to project the sensor 293 a desired distance into the right atrium 5 and/or coronary sinus ostium 14. FIG. 30 shows an example implant device 305, wherein the sensor device 308 associated therewith is coupled to the associated stent anchor 306 via a relatively short coupling strut or arm 309, such that the sensor 308 projects only a short distance past the axial end of the anchor 306. For example, the sensor 308 may be merely clipped or secured to a strut feature of one or more cells of the stent 306 without utilizing an extended arm feature extending from the lattice of the stent.

Figure 31:
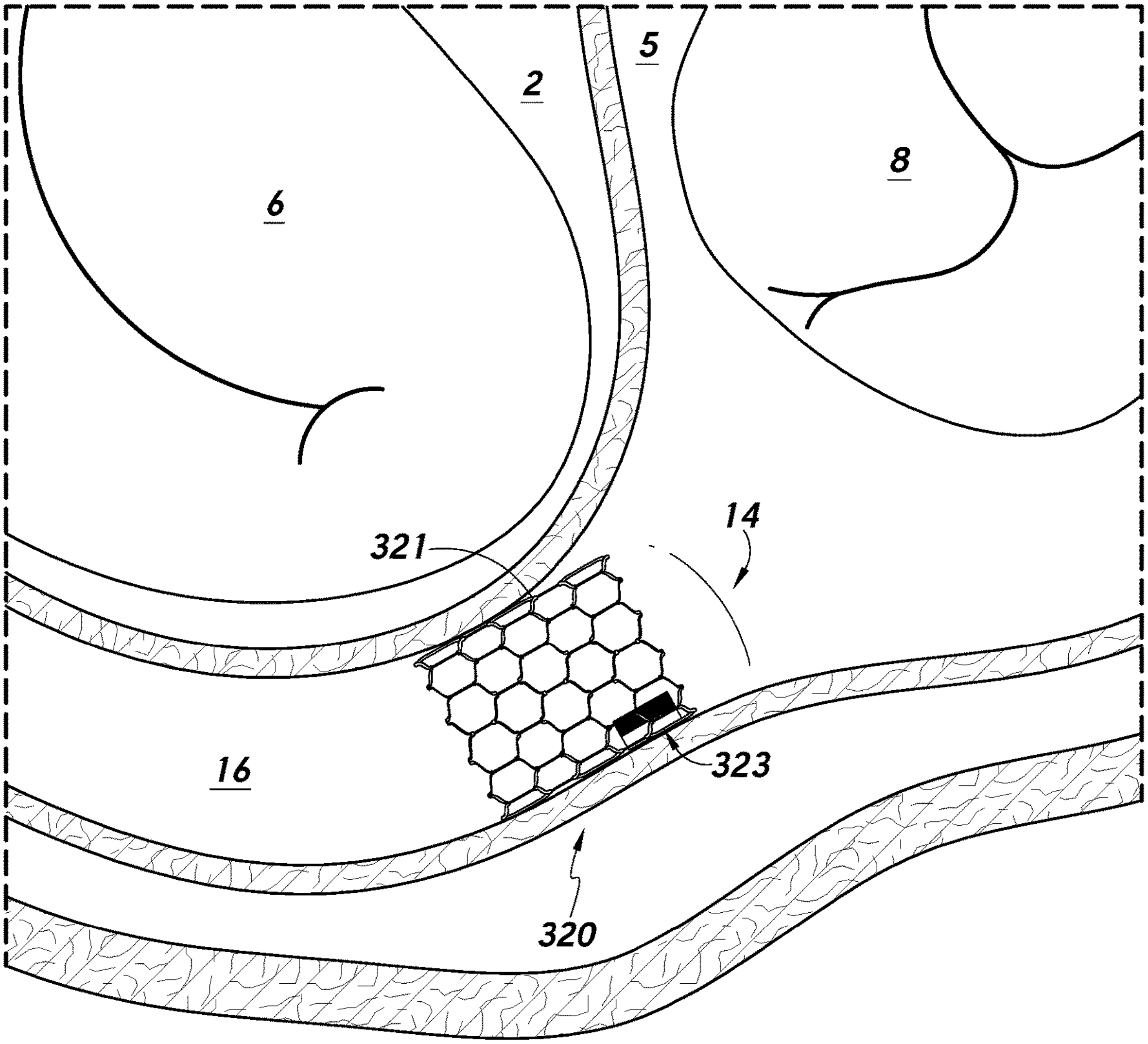
FIG. 31 shows a, sensor implant device anchored in a coronary sinus in accordance with one or more embodiments.

FIG. 31 shows a sensor implant device 320 disposed/deployed within the coronary sinus 16 and/or coronary sinus ostium 14, wherein the device 320 includes a sensor device 323 disposed at least partially within an inner diameter of an anchor 321 of the device 320. For example, the sensor device 323 may be secured or attached to one or more cells of a stent-type lattice of the anchor 321 through any type of attachment means, including one or more clips, books, straps, collars, and/or any other type of mechanical and/or tension fit.

Figure 32:
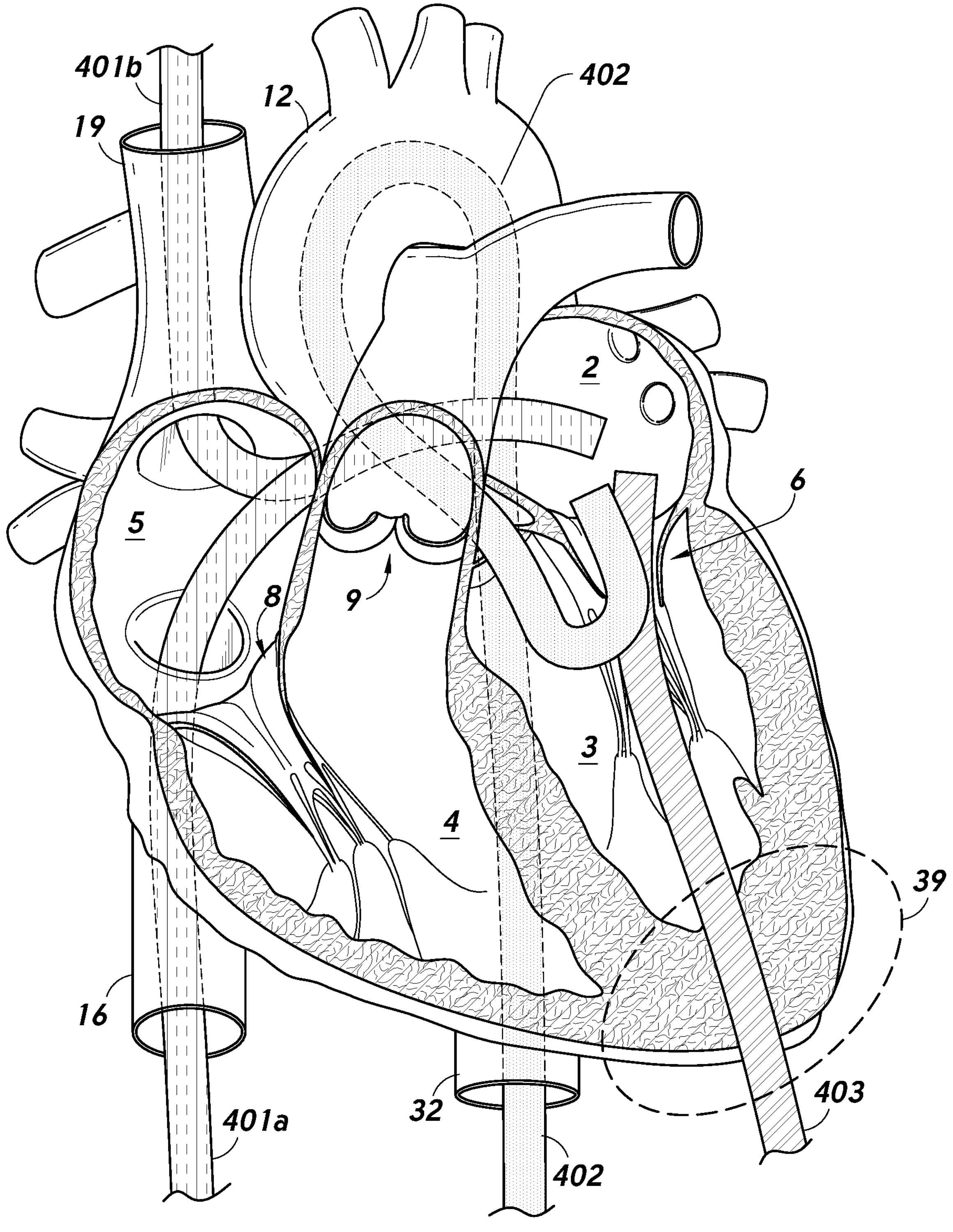
FIG. 32 illustrates various access paths through which access to a target cardiac anatomy may be achieved in accordance with one or more embodiments.

Sensor implant devices in accordance with one or more embodiments of the present disclosure may be advanced to the left atrium using any suitable or desirable procedure. For example, although access to the left atrium is illustrated and described in connection with certain embodiments as being via the right atrium and/or inferior vena cavae, such as through a transfemoral or other transcatheter procedure, other access paths/methods may be implemented in accordance with embodiments of the present disclosure, as described/shown in connection with FIG. 32. For example, FIG. 32 illustrates various access paths through which access to the left ventricle may be achieved, including transseptal access 401*a*, 401*b*, which may be made through the inferior vena cava 16 or superior vena cava 32, as respectively shown, and from the right atrium 5, through the septal wall (not shown) and into the left atrium 2. For transaortic access 402, a delivery catheter may be passed through the descending aorta, aortic arch 12, ascending aorta, and aortic valve 7, and into the left atrium 2 through the mitral valve 6. For transapical access 403, access may be made directly through the apex of the heart into the left ventricle 3, and into the left atrium 2 through the mitral valve 6. Other access paths are also possible beyond those shown in FIG. 32.

Additional Embodiments

Depending on the embodiment, certain acts, events, or functions of any of the processes described herein can be performed in a different sequence, may be added, merged, or left out altogether. Thus, in certain embodiments, not all described acts or events are necessary for the practice of the processes.

Certain standard anatomical terms of location are used herein with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. Spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present. As used herein, the term "and/or" used between the last two of a list of elements means any one or more of the listed elements. For example, the phrase "A, B, and/or C" means "A," "B," "C," "A and B," "A and C," "B and C," or "A, B, and C."

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

With respect to the various methods and processes disclosed herein, although certain orders of operations or steps are illustrated and/or described, it should be understood that the various steps and operations shown and described may be performed in any suitable or desirable temporal order. Furthermore, any of the illustrated and/or described operations or steps may be omitted from any Riven method or process, and the illustrated/described methods and processes may include additional Operations or steps not explicitly illustrated or described.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above but should be determined only by a fair reading of the claims that follow.

What is claimed is:

1. A method of sensing a physiological parameter, the method comprising:

- advancing a delivery system to a right atrium of a heart of a patient via a transcatheter access path;
- advancing the delivery system through an interatrial septum wall into a left atrium of the heart;
- deploying a distal anchor of a sensor implant device from the delivery system;
- anchoring the distal anchor of the sensor implant device to a first pulmonary vein;
- withdrawing the delivery system away from the first pulmonary vein, thereby exposing at least a portion of a sensor module of the sensor implant device in the left atrium, the sensor module being coupled to the distal anchor via a first arm segment;
- deploying a proximal anchor of the sensor implant device from the delivery system, the proximal anchor being coupled to the sensor module via a second arm segment;
- anchoring the proximal anchor of the sensor implant device to a second pulmonary vein, thereby securing the sensor module in a position adjacent to a left atrial wall portion of the left atrium between the first pulmonary vein and the second pulmonary vein; and
- withdrawing the delivery system from the heart.

2. The method of claim 1, further comprising sensing a physiological parameter associated with the left atrium using a sensor element of the sensor module.

3. The method of claim 2, wherein the physiological parameter is left atrial blood pressure.

4. The method of claim 1, wherein the first and second arm segments are part of a unitary arm structure coupled between the distal anchor and the proximal anchor.

5. The method of claim 4, wherein the sensor module includes an arm engagement feature configured to attach the sensor module to the unitary arm structure.

6. The method of claim 1, wherein the sensor module includes a guidewire lumen configured to have a guide wire disposed therein.

7. The method of claim 6, further comprising advancing the guidewire lumen of the sensor module along a pre-positioned guide wire.

8. The method of claim 1, wherein the sensor module comprises a housing and a sensor element disposed at least partially within the housing.

9. The method of claim 8, wherein the sensor element is disposed at least partially within the housing such that a transducer surface of the sensor element is at least partially exposed to blood in the left atrium when the sensor implant device is disposed within the left atrium.

10. The method of claim 9, wherein the transducer surface is a pressure transducer diaphragm.

11. The method of claim 1, wherein said anchoring the distal anchor of the sensor implant device to the first pulmonary vein involves expanding a stent anchor within a conduit of the first pulmonary vein.

12. A sensor implant device comprising:

- a sensor module including a housing and a sensor element;
- a first stent anchor;
- a second stent anchor; and
- an at least partially flat coupling arm extending from a distal portion of the first stent anchor to a proximal portion of the second stent anchor and running along entire lengths of the first stent anchor and the second stent anchor, the sensor module being attached to a medial portion of the coupling arm between the first and second stent anchors.

13. The sensor implant device of claim 12, wherein each of the first and second stent anchors is self-expanding.

14. The sensor implant device of claim 12, wherein the sensor element is configured to generate a signal indicative of a physiological parameter.

15. The sensor implant device of claim 14, wherein the physiological parameter is fluid pressure.

16. The sensor implant device of claim 12, wherein the coupling arm comprises first and second arm segments on opposite sides of the sensor module.

17. The sensor implant device of claim 12, wherein the sensor module includes an engagement feature configured to engage with the coupling arm.

18. The sensor implant device of claim 17, wherein the engagement feature is associated with an underside of the housing of the sensor module.

19. The sensor implant device of claim 12, wherein the sensor module includes a channel feature configured to receive therein a guide wire.

20. The sensor implant device of claim 12, wherein the sensor element comprises a transducer surface that is at least partially exposed external to the housing.

21. The sensor implant device of claim 20, wherein the transducer surface is associated with a pressure transducer diaphragm.

22. A delivery system comprising:

- an outer shaft;
- a sensor implant device disposed at least partially within the outer shaft, the sensor implant device comprising:

a first anchor device disposed within the outer shaft in a first pre-deployment configuration with a first diameter;

a second anchor device; and a sensor module physically coupled to the first anchor device and the second anchor device via respective connecting arm segments;

a distal inner shaft disposed at least partially within the outer shaft and configured to axially abut a proximal portion of the first anchor device within the outer shaft; and a proximal inner shaft disposed at least partially within the distal inner shaft and configured to axially abut a proximal portion of the sensor module within the distal inner shaft, the second anchor device being disposed within the proximal inner shaft in a second pre-deployment configuration with a second diameter that is less than the first diameter.

23. The delivery system of claim 22, wherein the first anchor device is disposed distal to a distal end of the distal inner shaft and the sensor module is disposed at least partially within the distal inner shaft.

24. The delivery system of claim 22, wherein the second anchor device is coupled to the sensor module via one of the respective connecting arm segments that is bent such that an end portion of the second anchor device is distally oriented within the proximal inner shaft.

25. The delivery system of claim 22, further comprising a pusher device disposed at least partially within the proximal inner shaft and configured to axially abut the second anchor device within the proximal inner shaft.

26. The delivery system of claim 25, wherein the pusher device includes a central lumen configured to receive a guidewire therein.

27. A sensor implant device comprising:

a first stent anchor;

a first arm structure connected to the first stent anchor and extending axially beyond an axial end of the first stent anchor; and a sensor device secured to the first arm structure;

wherein the first arm structure projects from an axial end of the first stent anchor and is bent outwardly at an approximately right angle relative to an axis of the first stent anchor, such that the sensor device is positioned entirely radially outside of an outer diameter of the first stent anchor.

28. The sensor implant device of claim 27, wherein the first stent anchor is dimensioned so as to be configured to anchor within a pulmonary vein in an expanded deployment configuration.

29. The sensor implant device of claim 27, wherein the first arm structure has shape memory characteristics that cause the first arm structure to deflect radially outward with respect to the axis of the first stent anchor when the sensor implant device is deployed.

30. The sensor implant device of claim 27, further comprising:

a second stent anchor; and a second arm structure connected to the second stent anchor and extending beyond an axial end of the second stent anchor;

wherein the sensor device is secured to the second arm structure.

31. The sensor implant device of claim 30, wherein the second arm structure has a U-shaped bend that orients an axial end of the second stent anchor towards the sensor device.

32. The sensor implant device of claim 30, wherein the first arm structure and the second arm structure are dimensioned to position the sensor device between a first pulmonary vein and a second pulmonary vein.

33. The sensor implant device of claim 32, wherein the first arm structure and the second arm structure are adapted to position the sensor device adjacent an atrial wall at a position between the first pulmonary vein and the second pulmonary vein.

34. The sensor implant device of claim 30, wherein the second arm structure has shape memory characteristics that cause the second arm structure to deflect radially outward with respect to an axis of the second stent anchor when the sensor implant device is deployed.

35. A method of sensing a physiological parameter, the method comprising:

advancing a delivery system to a left atrium of a heart of a patient via a transcatheter access path;

deploying a first anchor of a sensor implant device from the delivery system;

anchoring the first anchor of the sensor implant device within a first pulmonary vein;

withdrawing the delivery system away from the first pulmonary vein;

exposing at least a portion of a sensor module of the sensor implant device in the left atrium, the sensor module being coupled to the first anchor via a first support arm segment;

allowing the first support arm segment to bend radially away from an axis of the first anchor to position the sensor module in a position abutting against a wall portion of the left atrium between the first pulmonary vein and a second pulmonary vein; and withdrawing the delivery system from the heart.

36. The method of claim 35, further comprising sensing a physiological parameter associated with the left atrium using a sensor element of the sensor module.

37. The method of claim 36, wherein the physiological parameter is left atrial blood pressure.

38. The method of claim 35, further comprising:

deploying a second anchor of the sensor implant device from the delivery system; and anchoring the second anchor of the sensor implant device to a second pulmonary vein, the second anchor being coupled to the sensor module via a second support arm segment.

39. The method of claim 38, further comprising allowing the second support arm portion that physically couples the sensor module to the second anchor to bend to a perpendicular orientation relative to an axis of the second anchor.

* * * * *